US012533353B2

(12) United States Patent
Hassig et al.

(10) Patent No.: US 12,533,353 B2
(45) Date of Patent: Jan. 27, 2026

(54) METHODS OF TREATMENT OF CANCER COMPRISING CDC7 INHIBITORS

(71) Applicant: CARNA BIOSCIENCES, INC., Hyogo (JP)

(72) Inventors: Christian Andrew Hassig, San Diego, CA (US); Ryan James Hansen, San Diego, CA (US); Snezana Milutinovic, San Diego, CA (US); Bryan William Strouse, Ann Arbor, MI (US)

(73) Assignee: CARNA BIOSCIENCES, INC., Hyogo (JP)

( * ) Notice: Subject to any disclaimer, the term of this patent is extended or adjusted under 35 U.S.C. 154(b) by 539 days.

(21) Appl. No.: 17/275,732

(22) PCT Filed: Aug. 28, 2019

(86) PCT No.: PCT/US2019/048657

§ 371 (c)(1),
(2) Date: Mar. 12, 2021

(87) PCT Pub. No.: WO2020/068347

PCT Pub. Date: Apr. 2, 2020

(65) Prior Publication Data

US 2021/0393620 A1 Dec. 23, 2021

Related U.S. Application Data

(60) Provisional application No. 62/760,638, filed on Nov. 13, 2018, provisional application No. 62/735,778, filed on Sep. 24, 2018.

(30) Foreign Application Priority Data

Feb. 26, 2019 (WO) ................ PCT/US2019/019676

(51) Int. Cl.

| | |
|---|---|
| ***A61K 31/496*** | (2006.01) |
| ***A61K 9/00*** | (2006.01) |
| ***A61K 31/519*** | (2006.01) |
| ***A61K 31/5377*** | (2006.01) |
| ***A61K 31/675*** | (2006.01) |
| ***A61K 45/06*** | (2006.01) |
| ***A61P 35/00*** | (2006.01) |
| ***A61P 35/02*** | (2006.01) |
| ***A61P 35/04*** | (2006.01) |
| ***C07D 471/04*** | (2006.01) |

(52) U.S. Cl.

CPC .......... *A61K 31/496* (2013.01); *A61K 31/519* (2013.01); *A61K 31/5377* (2013.01); *A61K 31/675* (2013.01); *A61K 45/06* (2013.01); *A61P 35/00* (2018.01); *A61P 35/02* (2018.01); *A61P 35/04* (2018.01); *C07D 471/04* (2013.01); *A61K 9/0019* (2013.01)

(58) Field of Classification Search

CPC ...... C07D 471/04; A61K 31/496; A61P 35/00
See application file for complete search history.

(56) References Cited

U.S. PATENT DOCUMENTS

| | | | | |
|---|---|---|---|---|
| 4,107,288 | A | 8/1978 | Oppenheim et al. | |
| 5,145,684 | A | 9/1992 | Liversidge et al. | |
| 8,552,048 | B2 | 10/2013 | Ammons et al. | |
| 8,742,113 | B2 * | 6/2014 | Irie .................... | A61K 31/4709 546/113 |
| 2011/0118298 | A1 | 5/2011 | Fritz et al. | |
| 2012/0276093 | A1 | 11/2012 | Ballinari et al. | |
| 2014/0018533 | A1 | 1/2014 | Irie et al. | |
| 2015/0218138 | A1 | 8/2015 | Vanotti et al. | |
| 2017/0065609 | A1 * | 3/2017 | Funakoshi ............. | A61K 45/06 |
| 2021/0393620 | A1 | 12/2021 | Hassig et al. | |

FOREIGN PATENT DOCUMENTS

| | | |
|---|---|---|
| CA | 3 042 849 | 5/2018 |
| JP | 2007501825 | 2/2007 |
| JP | 2007501827 | 2/2007 |
| JP | 2009515849 | 4/2009 |
| JP | 2009519919 | 5/2009 |
| JP | 2009534400 | 9/2009 |
| JP | 2010505922 | 2/2010 |
| JP | 2010519324 | 6/2010 |
| JP | 2010527324 | 8/2010 |
| JP | 2011507908 | 3/2011 |
| JP | 2012519653 | 8/2012 |
| JP | 2012533551 | 12/2012 |
| JP | 2012533553 | 12/2012 |
| JP | 2013511487 | 4/2013 |
| JP | 2013522212 | 6/2013 |
| JP | 2013525303 | 6/2013 |
| JP | 2013525304 | 6/2013 |
| JP | 2013525354 | 6/2013 |

(Continued)

OTHER PUBLICATIONS

Kent, "Absolute Dose", The Oxford Dictionary of Sports Science and Medicine, 2006, 3 ed. (Year: 2006).*
Shimizu et al., "First-in-human phase 1 study of TAK-931, an oral cell division cycle 7 (CDC7) inhibitor, in patients with advanced solid tumors", 2018, Journal of Clinical Oncology, Meeting Abstract (Year: 2018).*
Takeda, "An Open-Label, Phase 2, Parallel Arm Study to Evaluate the Safety, Tolerability, and Activity of TAK-931 Single Agent in Patients With Metastatic Pancreatic Cancer, Metastatic Colorectal Cancer, and Other Advanced Solid Tumors", 2018, Takeda, pp. 1-99 (Year: 2018).*

(Continued)

*Primary Examiner* — Brenda L Coleman
*Assistant Examiner* — Madeline E Braun
(74) *Attorney, Agent, or Firm* — Wenderoth, Lind & Ponack, L.L.P.

(57) ABSTRACT

Herein disclosed are methods of treatment administering SRA141 as a monotherapy or in a combination therapy useful for inhibiting the growth of tumors such as those in patients with cancer.

20 Claims, 44 Drawing Sheets

Specification includes a Sequence Listing.

(56) References Cited

FOREIGN PATENT DOCUMENTS

| | | |
|---|---|---|
| WO | WO 2007110344 | 10/2007 |
| WO | WO 2010122979 | 10/2010 |
| WO | WO 2011102399 | 8/2011 |
| WO | WO 2012002568 | 1/2012 |
| WO | WO 2012133802 | 10/2012 |
| WO | WO 2015/115355 | 8/2015 |
| WO | 2019/165473 | 8/2019 |

OTHER PUBLICATIONS

Nowak et al., "The role of chromosomal instability in tumor initiation", 2002, PNAS, 99, pp. 16226-16231 (Year: 2002).*
Zhang et al., "Multiple roles of APC and its therapeutic implications in colorectal cancer", 2017, Journal of the National Cancer Institute, 109, pp. 1-10 (Year: 2017).*
Zhao et al., "Inhibition of CHK1 enhances cell death induced by the Bcl-2-selective inhibitor ABT-199 in acute myeloid leukemia cells", 2016, Oncotarget, 7, pp. 34785-34799 (Year: 2016).*
Sawa et al., "Drug design with Cdc7 kinase: a potential novel cancer therapy target", 2008, Drug Design, Development and Therapy , 2, pp. 255-264 (Year: 2008).*
Krawczyk et al., "Increased Activity of the S Phase Kinase Cdc7 is Associated with Poor Outcome in Diffuse Large B Cell Lymphoma (DLBCL)", 2009, Blood, 114, 2 pgs. (Year: 2009).*
Altschul et al., "Basic local alignment search tool," Oct. 1990, J. Mol.Biol. 215:403-410.
Eisenhauer, et al., "New response evaluation criteria in solid tumours: revised RECIST guideline (version 1.1)," Jan. 2009, Eur J Cancer, 45(2):228-47.
Extended European Search Report in European Application No. 19866944.2, dated May 27, 2022, 8 pages.
Foucquier et al., "Analysis of drug combinations: current methodological landscape," Jun. 2015, Pharmacol. Res. Perspect. 3(3):e00149.
Howlader et al., (eds), "SEER Cancer Statistics Review, 1975-2014," Apr. 2018, National Cancer Institute, retrieved from URL< http://seer.cancer.gov/csr/1975_2014/>, based on Nov. 2016 SEER data submission, posted to the SEER web site, Apr. 2017.
Irie et al., "Discovery of AS-0141, a Potent and Selective Inhibitor of CDC7 Kinase for the Treatment of Solid Cancers," Oct. 2021, J Med Chem., 64(19):14153-14164.
Masai et al., "Cdc7 kinase complex: a key regulator in the initiation of DNA replication," Mar. 2002, Journal of Cellular Physiology, 190(3):287-296.
Nair et al., "A simple practice guide for dose conversion between animals and human," Mar. 2016, J. Basic Clin. Pharm, 7(2): 27-31.
Needleman et al., "A general method applicable to the search for similarities in the amino acid sequence of two proteins," Mar. 1970, J Mol Biol. 48:443-53.
PCT International Preliminary Report on Patentability in PCT Application No. PCT/US2019/048657, dated Mar. 23, 2021.
Pearson et al., "Improved tools for biological sequence comparison," Apr. 1988, Proc. Nat'l. Acad. Sci. USA 85:2444-8.
Smith et al., "Comparison of biosequences," Dec. 1981, Adv. Appl. Math. 2:482-489.
Wang et al., Screening for Microsatellite Instability in Colorectal Cancer and Lynch Syndrome—A Mini Review, Jan. 2016, NA J Med Sci. 2016;9(1);5-11.
Zehir et al., "Mutational landscape of metastatic cancer revealed from prospective clinical sequencing of 10,000 patients," Jun. 2017, Nat Med [Internet]. 2017;23(6).
Monga, S. P., et al. "Intratumoral Therapy of Cisplatin/Epinephrine Injectable Gel for Palliation in Patients with Obstructive Esophageal Cancer", Am. J . Clin. Oncol., 2000, vol. 23, No. 4, pp. 386-392.
Tomayko et al., "Determination of subcutaneous tumor size in athymic (nude) mice", Cancer Chemotherapy and Pharmacology, vol. 24, Issue 3, 1989, pp. 148-154.
Richtig et al., "Calculated tumour volume as a prognostic parameter for survival in choroidal melanomas", Eye, 2004, vol. 18, pp. 619-623.
Jensen et al., "Tumor volume in subcutaneous mouse xenografts measured by microCT is more accurate and reproducible than determined by 18F-FDG-microPET or external caliper", BMC Medical Imaging, 2008, vol. 8, No. 16, 99. 1-9.
Faustino-Rocha et al., "Estimation of rat mammary tumor volume using caliper and ultrasonography measurements", Lab Animal, Jun. 2013, vol. 42, No. 6, pp. 2017-2224.
Bonte et al., "Cdc7-Dbf4 Kinase Overexpression in Multiple Cancers and Tumor Cell Lines is Correlated with p53 Inactivation", Neoplasia, Sep. 2008, vol. 10, No. 9, pp. 920-931.
Cadigan et al., "Wnt signaling: complexity at the surface", Journal of Cell Science, 2006, vol. 19, No. 3, pp. 395-402.
Cheng et al., "Increased Cdc7 expression is a marker of oral squamous cell carcinoma and overexpression of Cdc7 contributes to the resistance to DNA-damaging agents", Cancer Letters, 2013, vol. 337, No. 2, pp. 218-225.
Cremolini et al., "First-line chemotherapy for mCRC—a review and evidence-based algorithm", Nat Rev Clin Oncol, 2015, vol. 12, No. 10, pp. 607-619.
Dienstmann et al., "Consensus molecular subtypes and the evolution of precision medicine in colorectal cancer", Nat Rev Cancer, 2017, vol. 17, pp. 79-92.
Ferlay et al., "Cancer incidence and mortality worldwide: Sources, methods and major patterns in GLOBOCAN 2012", International Journal of Cancer, 2015, vol. 136, pp. E359-E386.
Fodde et al., Mutations in the APC tumour suppressor gene cause chromosomal instability, Nature Cell Biology, Apr. 2001, vol. 3, pp. 433-438.
Gregory et al., "CDK9 inhibition by dinaciclib potently suppresses Mcl-1 to induce durable apoptotic responses in aggressive MYC-driven B-cell lymphoma in vivo", Leukemia, 2015, vol. 29, pp. 1437-1441.
Guinney et al., The Consensus Molecular Subtypes of Colorectal Cancer, Nat Med., 2016, vol. 21, No. 11, pp. 1350-1356.
Hailey et al., "Biliary Proliferative Lesions in the Sprague-Dawley Rat: Adverse/Non-adverse", 2014, vol. 42, pp. 844-854.
Hou et al., "High expression of cell division cycle 7 protein correlates with poor prognosis in patients with diffuse large B-cell lymphoma", Med Oncol, 2012, vol. 29, pp. 3498-3503.
Huggett et al., "Cdc7 is a potent anti-cancer target in pancreatic cancer due to abrogation of the DNA origin activation checkpoint", Oncotarget, 2016, vol. 7, No. 14, pp. 18495-18507.
"ICH Harmonised Tripartite Guideline: Nonclinical Evaluation for Anticancer Pharmaceuticals S9", International Conference on Harmonisation of Technical Requirements for Registration of Pharmaceuticals for Human Use, 2009, pp. 1-9.
Iwai et al., "Phospho-proteomics analysis to determine the signaling pathways affected by a novel CDC7-selective inhibitor TAK-931", AACR Annual Meeting, 2018, Abstract 2312.
Larasati et al., "Mechanisms Governing DDK Regulation of the Initiation of DNA Replication", Genes, 2017, vol. 8 (1), 3, pp. 1-12.
Montagnoli et al., "Cdc7 Inhibition Reveals a p53-Dependent Replication Checkpoint That is Defective in Cancer Cells.", Cancer Research, 2004, vol. 64, pp. 7110-7116.
Rodriguez-Acebes et al., "Targeting DNA Replication before it Starts: Cdc7 as a Therapeutic Target in p53-Mutant Breast Cancers", The American Journal of Pathology, Oct. 2010, vol. 177, No. 4, pp. 2034-2045.
Schukken et al., "CIN and Aneuploidy: Different Concepts, Different Consequences", BioEssays, 2018, vol. 40, No. 1, pp. 1-9.
Swords et al., "Cdc7 kinase—A new target for drug development", European Journal of Cancer, 2010, vol. 46, pp. 33-40.
Therkildsen et al., "The predictive value of KRAS, NRAS, BRAF, PIK3CA and PTEN for anti-EGFR treatment in metastatic colorectal cancer: A systematic review and meta-analysis", Acta Oncologica, 2014, vol. 53, No. 7, pp. 852-864.
Xiang et al., "A selective CDC7 inhibitor (LY3177833) impacts chromosome dynamics and has robust and durable activity in PDX tumor models", AACR Annual Meeting, 2016, Late breaking abstract.
Zehir et al., "Mutational landscape of metastatic cancer revealed from prospective clinical sequencing of 10,000 patients", Nature Medicine, Jun. 2017, vol. 23, No. 6, pp. 706-713.
International Search Report issued Nov. 15, 2019 in International (PCT) Application No. PCT/US2019/048657.
Chava, S. et al., "Co-targeting of specific epigenetic regulators in combination with CDC7 potently inhibit melanoma growth." 2022, iScience 25, 104752, 43 pages.

* cited by examiner

* $p < 0.05$ vs vehicle; ** $p < 0.01$ vs vehicle

MV-4-11
Group mean +/- SEM
Tumor Volume (mm³)
Day
D41
Mean TGI
86%
87%
Vehicle
SRA141 (75 mg/kg) BID, 5 on, 2 off, p.o.
SRA141 (150 mg/kg) 5 on, 2 off, p.o.

Treatment well tolerated
MV-4-11
Group mean +/- SEM
Body Wt Change (%) from Baseline
Day Vehicle
SRA141 (75 mg/kg) BID, 5 on, 2 off
SRA141 (150 mg/kg) QD, 5 on, 2 off
Tumor Volume (mm³)
Day

* *One mouse from vehicle and one mouse from SRA141 (120 mg/kg) were euthanized on D7 due to weight loss*

SRA141 @500nM

Summary of Hits

| % of Control | SRA141 | TAK-931 |
|---|---|---|
| Less < 35% | 38 | 52 |
| Less < 20% | 26 | 39 |
| Less < 10% | 21 | 29 |
| Less < 5% | 14 | 20 |
| Less < 1% | 1 | 11 |

TAK-931 @500nM

| | 50 mg/kg | 100 mg/kg | 150 mg/kg |
|---|---|---|---|
| | *Mean (SD)* | *Mean (SD)* | *Mean (SD)* |
| $T_{max}$ (h) | 1 | 1 | 1 |
| $C_{max}$ (ng/mL) | 690 (174) | 1074 (289) | 1463 (368) |
| $AUC_{last}$ (ng•h/mL) | 5801 | 11920 | 16479 |

METHODS OF TREATMENT OF CANCER COMPRISING CDC7 INHIBITORS

CROSS REFERENCE TO RELATED APPLICATIONS

This application is a national phase entry pursuant to 35 U.S.C. § 371 of International Application No. PCT/US2019/048657, filed Aug. 28, 2019, which claims the benefit of and priority to U.S. Provisional Application No. 62/735,778, filed Sep. 24, 2018; U.S. Provisional Application No. 62/760,638, filed Nov. 13, 2018; and PCT Application No. PCT/US2019/019676, filed Feb. 26, 2019. The content of each of the above referenced applications is incorporated by reference in its entirety.

SEQUENCE LISTING

A sequence listing in electronic (ASCII text file) format is filed with this application and incorporated herein by reference. The name of the ASCII text file is "2021_0442_ST25.txt"; the file was created on Jul. 3, 2025; the size of the file is 542 bytes.

BACKGROUND

Cancer is a group of diseases caused by uncontrolled, unlimited growth of cells within a living body. Since cancer cells usually grow faster than normal cells, cancers are capable of being treated by controlling the replication of DNA during cell division, particularly during the division of chromosomes.

Cdc7 is a serine-threonine protein kinase enzyme which is essential for the initiation of DNA replication in the cell cycle. Specifically, Cdc7 forms a complex with cofactors such as Dbf4 (ASK), and phosphorylates its substrate, MCM (mini-chromosome maintenance) proteins. It is purported that this phosphorylation results in assembly of Cdc45 and a DNA polymerase on the DNA to form an MCM complex, thereby initiating the DNA replication.

Significant interest has arisen in Cdc7 as an anticancer target since the expression level of Cdc7 is frequently elevated in various cancer cell lines and human tumor tissues. It has been found that Cdc7 is overexpressed not only in commonly established cell lines derived from human tumors, but also in cells taken from live tissues.

Certain Cdc7 inhibitors have been demonstrated to effect the growth of human tumor cells, such as HeLa and HCT116 cells, while exhibiting only limited effects on normal cells.

Currently, there are no effective therapeutic compositions and methods useful for the treatment of cancer using Cdc7 inhibitors.

SUMMARY

Described herein is a method of treating a cancer, the method comprising:

administering to a subject with the cancer a therapeutically effective amount of a SRA141 compound represented by the formula (I-D):

(I-D)

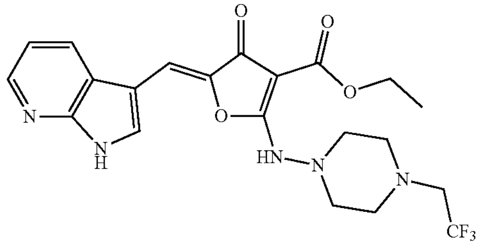

wherein the therapeutically effective amount is between an absolute dose of 10-400 mg/day or between 10-1000 mg/day.

In some embodiments, the subject is a human.

In some embodiments, the therapeutically effective amount is at least 10 mg/day, at least 20 mg/day, at least 40 mg/day, at least 80 mg/day, at least 160 mg/day, or at least 320 mg/day. In some embodiments, the therapeutically effective amount is at least 15 mg/day, at least 25 mg/day, at least 50 mg/day, at least 100 mg/day, at least 150 mg/day, at least 200 mg/day, at least 250 mg/day, at least 300 mg/day, or at least 350 mg/day.

In some embodiments, the SRA141 compound is administered orally.

In some embodiments, the SRA141 compound is administered daily. In some embodiments, the SRA141 compound is administered for at least 5 consecutive days, at least 7 consecutive days, or at least 14 consecutive days. In some embodiments, the SRA141 compound is administered following a dosing schedule selected from the group consisting of: 5 days of dosing followed by 2 days of non-dosing each week; 1 week of daily dosing followed by 1, 2, or 3 weeks of non-dosing; 2 or 3 weeks of daily dosing followed by 1, or 2 weeks of non-dosing; and dosing on days 2 and 3 of a weekly cycle. In some embodiments, the therapeutically effective amount is administered in a single dose once a day. In some embodiments, half of the therapeutically effective amount is administered twice a day.

In some embodiments, the cancer is selected from the group consisting of: melanoma, uterine cancer, thyroid cancer, blood cancer, bladder cancer, breast cancer, cervical cancer, colorectal cancer (CRC), gastric cancer, endometrial cancer, hepatocellular cancer, leukemia, lymphoma, myeloma, non-small cell lung cancer, ovarian cancer, prostate cancer, pancreatic cancer, brain cancer, sarcoma, small cell lung cancer, neuroblastoma, and head and neck cancer. In some embodiments, the cancer is a blood cancer selected from the group consisting of: acute myeloid leukemia (AML), chronic myelogenous leukemia (CML), chronic eosinophilic leukemia, and diffuse large B-cell lymphoma (DLBCL). In some embodiments, the cancer is AML.

In some embodiments, the cancer is metastatic colorectal cancer (mCRC). In some embodiments, the mCRC is not categorized as having a high microsatellite instability (MSI-H) status. In some embodiments, the MSI-H status is determined by detection of repetitive DNA sequences selected from the group consisting of: mononucleotide repeat markers, dinucleotide repeat markers, quasimonomorphic markers, and combinations thereof. In some embodiments, the detection if performed by a method selected from the group consisting of: PCR analysis, multiplexed PCR analysis, capillary electrophoresis, DNA sequencing, and combinations thereof.

In some embodiments, a tumor associated with the cancer comprises a phenotype selected from the group consisting of: chromosome instability (CIN), a spindle checkpoint assembly defect, a mitosis defect, a G1/S checkpoint defect, and combinations thereof. In some embodiments, a tumor associated with the cancer comprises a Wnt signaling pathway mutation. In some embodiments, the Wnt signaling pathway mutation is selected from the group consisting of: an Adenomatous polyposis coli (APC) gene mutation, a FAT1 mutation, a FAT4 mutation, and combinations thereof.

In some embodiments, the method further comprises screening the tumor associated using either archival or fresh tumor biopsy. In some embodiments, the screening comprises examining a pattern of chromosome separation by histochemical staining, examining pharmacodynamic markers by histochemical staining, or a combination thereof. In some embodiments, the screening further comprises determining whether the tumor exhibits aberrant mitosis. In some embodiments, the screening is performed before the administering of the SRA141 compound. In some embodiments, the screening is performed after the administering of the SRA141 compound.

In some embodiments, the method results in a plasma $C_{max}$ greater than 600, greater than 1000, or greater than 1400 ng/mL of the SRA141 compound in the subject after administration. In some embodiments, the method results in an $AUC_{last}$ greater than 5800, greater than 11900, or greater than 16400 ng-h/mL of the SRA141 compound in the subject after administration. In some embodiments, the method results in an intra-tumoral concentration of greater than 500 ng/mL, greater than 600 ng/mL, greater than 900 ng/mL, or greater than 1300 ng/mL of the SRA141 compound in the subject after administration. In some embodiments, the intra-tumoral concentration is reached after multiple doses of the SRA141 compound. In some embodiments, the intra-tumoral concentration is reached after a single dose of the SRA141 compound.

In some embodiments, the method results in in vivo inhibition of MCM2 phosphorylation. In some embodiments, the in vivo inhibition of MCM2 phosphorylation is at amino acid residues Ser40 or Ser53. In some embodiments, the in vivo inhibition of MCM2 phosphorylation is in a tumor associated with the cancer. In some embodiments, the in vivo inhibition of MCM2 phosphorylation in the tumor associated with the cancer is at least 50% relative to an untreated tumor sample. In some embodiments, the untreated tumor sample is a biopsy obtained prior to administration of the SRA141 compound to the subject. In some embodiments, the in vivo inhibition of MCM2 phosphorylation is after a single dose of the SRA141 compound. In some embodiments, the in vivo inhibition of MCM2 phosphorylation is in skin of the subject. In some embodiments, the in vivo inhibition of MCM2 phosphorylation is measured by Western blot analysis, immunohistochemistry (IHC), or liquid chromatography-mass spectrometry (LC/MS). In some embodiments, the in vivo inhibition of MCM2 phosphorylation is measured in a biopsy of the subject. In some embodiments, the in vivo inhibition of MCM2 phosphorylation is measured after multiple doses of the SRA141 compound. In some embodiments, the in vivo inhibition of MCM2 phosphorylation is measured after the SRA141 compound reaches a steady state plasma concentration.

In some embodiments, the method results in growth inhibition of a tumor associated with the cancer. In some embodiments, the growth inhibition of the tumor is a minimum growth inhibition of at least 10%, at least 20%, at least 30%, at least 40%, at least 50%, at least 60%, at least 70%, at least 80%, or at least 90% relative to an untreated tumor. In some embodiments, the growth inhibition of the tumor is a minimum growth inhibition of at least 47% relative to an untreated tumor. In some embodiments, the growth inhibition of the tumor is a minimum growth inhibition of at least 93% relative to an untreated tumor. In some embodiments, the method results in a regression of a tumor associated with the cancer. In some embodiments, the regression is a complete regression. In some embodiments, the method results in cytotoxicity of a tumor associated with the cancer. In some embodiments, the method results in at least a 30% decrease in the sum of diameters of tumors associated with the cancer. In some embodiments, the method results in a partial response, a complete response, or stable disease in the subject.

In some embodiments, the method further includes determining level of growth inhibition of a tumor or lesion associated with the cancer. In some embodiments, the method includes comparing a second diameter of a target lesion following administration of SRA141 with a first diameter of the target lesion prior to administration of SRA141 to determine whether target lesion growth is inhibited. In some instances, the tumor or lesion growth is determined to be inhibited by at least 10%, at least 20%, at least 30%, at least 40%, at least 50%, at least 60%, at least 70%, at least 80%, or at least 90% relative to an untreated tumor or lesion.

In some embodiments, the method further comprises administering to the subject a second therapeutically effective amount of one or more additional treatments. In some embodiments, the one or more additional treatments comprises an anti-neoplastic agent. In some embodiments, the anti-neoplastic agent is selected from the group consisting of: a DNA polymerase inhibitor, a receptor tyrosine kinase inhibitor, a mammalian target of rapamycin (mTOR) pathway inhibitor. In some embodiments, the anti-neoplastic agent comprises a mitogen activated protein kinase (MAPK) pathway inhibitor. In some embodiments, the MAPK inhibitor is Trametinib. In some embodiments, the anti-neoplastic agent comprises a retinoid pathway regulator. In some embodiments, the retinoid pathway regulator is the RXR agonist Bexarotene or the RAR agonist Tretinoin (all-trans retinoic acid, ATRA). In some embodiments, the wherein the anti-neoplastic agent comprises an apoptosis regulator. In some embodiments, the apoptosis regulator comprises an apoptosis inducer. In some embodiments, the apoptosis inducer comprises a BCL-2 inhibitor. In some embodiments, the BCL-2 inhibitor is ABT-199. In some embodiments, the anti-neoplastic agent comprises a phosphatidylinositol-4,5-bisphosphate 3 kinase (PI3K) pathway inhibitor. In some embodiments, the PI3K pathway inhibitor is Copanlisib. In some embodiments, the anti-neoplastic agent comprises a PARP inhibitor. In some embodiments, the PARP inhibitor is BMN673. In some embodiments, the anti-neoplastic agent comprises an Aurora B kinase inhibitor. In some embodiments, the Aurora B kinase inhibitor is Barasertib. In some embodiments, the one or more additional treatments is administered daily. In some embodiments, the SRA141 compound and the one or more additional treatments demonstrate synergistic effects.

BRIEF DESCRIPTION OF THE DRAWINGS

These and other features, aspects, and advantages of the present invention will become better understood with regard to the following description, and accompanying drawings, where.

DETAILED DESCRIPTION

Figure 1A:
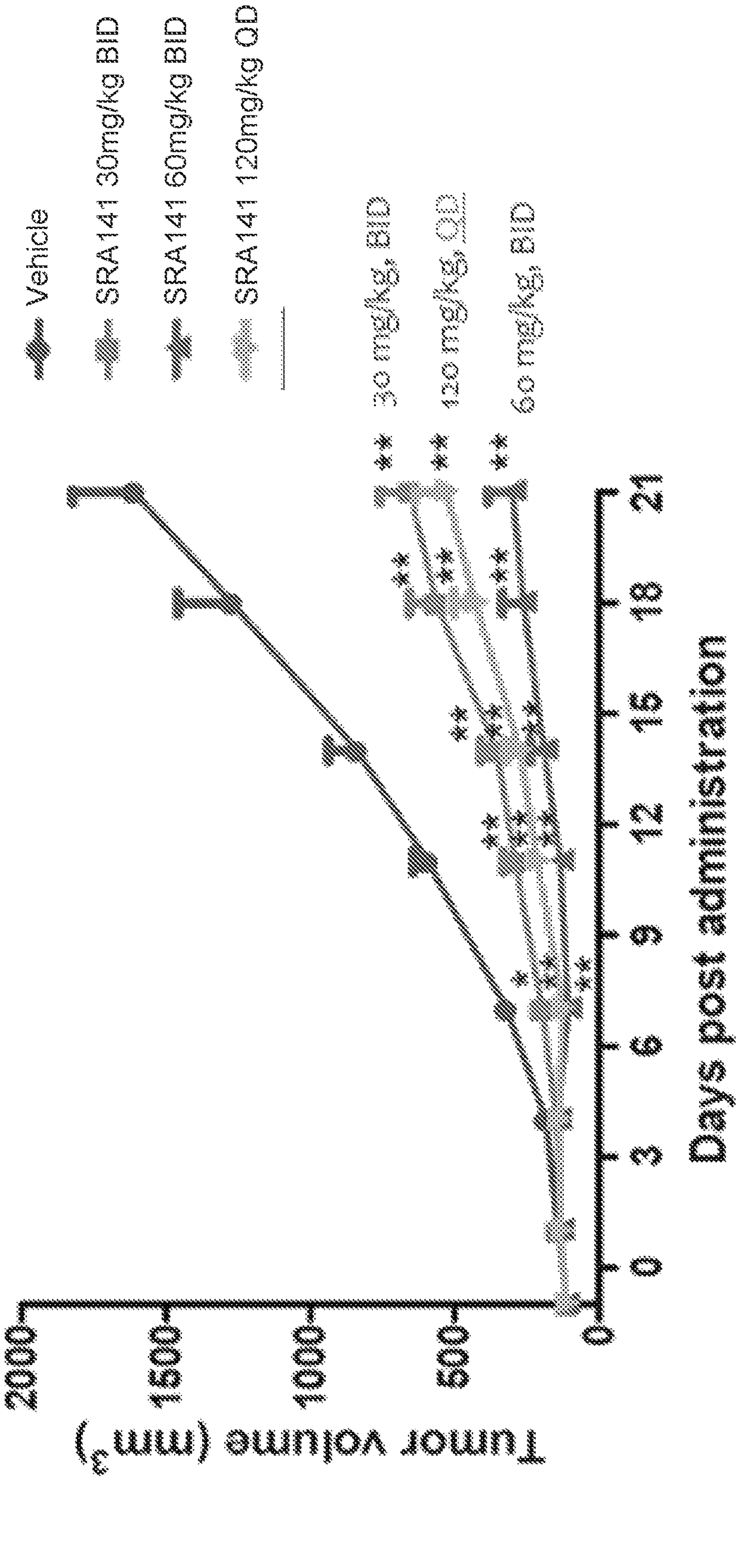
FIG. 1A is a graph showing tumor volumes of animals treated with SRA141 monotherapy in a mouse xenograft model of acute myeloid leukemia.

Disclosed herein are methods of inhibiting tumor growth in a subject, e.g., a human, by administration of an effective amount of the Cdc7 inhibitor SRA141. Also disclosed herein are methods of inhibiting tumor growth in a subject, e.g., a human, by administration of an effective amount of the Cdc7 inhibitor SRA141. Also disclosed herein are methods of inhibiting tumor growth in a subject, e.g., a human, by administration of an effective amount of the Cdc7 inhibitor SRA141 in a combination therapy.

Definitions

Terms used in the claims and specification are defined as set forth below unless otherwise specified.

The practice of the present invention includes the use of conventional techniques of organic chemistry, molecular biology (including recombinant techniques), microbiology, cell biology, biochemistry and immunology, which are within the skill of the art.

In this application, reference will be made to a number of technical designations. All numerical designations, e.g., pH, temperature, time, concentration, and weight, including ranges of each thereof, are approximations that typically may be varied (+) or (−) by increments of, e.g., 0.01, 0.05, 0.1, 0.5, 1.0, 5.0, or 10.0, as appropriate. All numerical designations may be understood as preceded by the term "about." Reagents described herein are exemplary and equivalents of such may be known in the art.

Compounds utilized in the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention. The compounds of the present invention may also contain unnatural proportions of atomic isotopes at one or more of the atoms that constitute such compounds. For example, the compounds may be radiolabeled with radioactive isotopes, such as for example, and without limitation, tritium (3H), iodine-125 ($^{125}I$), or carbon-14 ($^{14}C$). All isotopic variations of the compounds of the present invention, whether radioactive or not, are intended to be encompassed within the scope of the present invention.

The term "subject" refers to any mammal including humans, and mammals such as those animals of veterinary and research interest that are including, but not limited to: simians, cattle, horses, dogs, cats, and rodents.

The term "administering" or "administration of" a drug and/or therapy to a subject (and grammatical equivalents of this phrase) refers to both direct or indirect administration, which may be administration to a subject by a medical professional, may be self-administration, and/or indirect administration, which may be the act of prescribing or inducing one to prescribe a drug and/or therapy to a subject.

The term "coadministration" refers to two or more compounds administered in a manner to exert their pharmacological effect during the same period of time. Such coadministration can be achieved by either simultaneous, contemporaneous, or sequential administration of the two or more compounds.

The term "treating" or "treatment of" a disorder or disease refers to taking steps to alleviate the symptoms of the disorder or disease, e.g., tumor growth or cancer, or otherwise obtain some beneficial or desired results for a subject, including clinical results. Any beneficial or desired clinical results may include, but are not limited to, alleviation or amelioration of one or more symptoms of cancer or conditional survival and reduction of tumor load or tumor volume; diminishment of the extent of the disease; delay or slowing of the tumor progression or disease progression; amelioration, palliation, or stabilization of the tumor and/or the disease state; or other beneficial results.

The term "in situ" or "in vitro" refers to processes that occur in a living cell growing separate from a living organism, e.g., growing in tissue culture.

The term "in vivo" refers to processes that occur in a living organism.

The term "Cdc7" refers to a cell division cycle 7 serine/threonine-protein kinase that is encoded by a CDC7 gene.

The term "reduction" of a symptom or symptoms (and grammatical equivalents of this phrase) refers to decreasing the severity or frequency of the symptom(s), or elimination of the symptom(s).

It must be noted that, as used in the specification and the appended claims, the singular forms "a," "an" and "the" include plural referents unless the context clearly dictates otherwise.

Methods of the Invention

Disclosed herein are methods of inhibiting tumor growth in a subject, e.g., a human, by administration of the Cdc7 inhibitor SRA141. A detailed description of the compounds, kits comprising the compounds, and methods of use thereof are found below.

Administration

As disclosed herein, the methods of the invention include administration of an effective amount of SRA141. The present disclosure provides for a method of treatment wherein the effective amount of SRA141 is administered to a subject. The term "effective amount" or "therapeutically effective amount" refers to an amount that is effective to ameliorate a symptom of a disease, e.g. an amount that is effective to inhibit the growth of a tumor. In some aspects, the effective amount of SRA141 is less than maximum tolerated dose (MTD). In some aspects, the effective amount of SRA141 is less than 1000 mg/day, less than 500 mg/day, or less than 400 mg/day. In some aspects, the effective amount of SRA141 is less than 300 mg/day, less than 200 mg/day, less than 150 mg/day, less than 100 mg/day, or less than 75 mg/day. In some aspects, the effective amount of SRA141 is less than 324 mg/day. In some aspects, the effective amount of SRA141 is 324 mg/day. In some aspects, the effective amount of SRA141 is at least 10 mg/day. In some aspects, the effective amount of SRA141 is between 10-400 mg/day. In some aspects, the effective amount of SRA141 is between 10-324 mg/day. In some aspects, the effective amount of SRA141 is between 40-400 mg/day. In some aspects, the effective amount of SRA141 is at least 10 mg/day, at least 20 mg/day, at least 40 mg/day, at least 80 mg/day, at least 160 mg/day, or at least 320 mg/day. In some aspects, the effective amount of SRA141 is at least 15 mg/day, at least 25 mg/day, at least 50 mg/day, at least 75 mg/day, at least 100 mg/day, at least 150 mg/day, at least 200 mg/day, at least 250 mg/day, at least 300 mg/day, or at least 350 mg/day. In some aspects, the effective amount of SRA141 is 10 mg/day, 20 mg/day, 40 mg/day, 80 mg/day, 160 mg/day, 320 mg/day, 325 mg/day, 350 mg/day, or 400 mg/day. In some aspects, the effective amount of SRA141 is 15 mg/day, 25 mg/day, 50 mg/day, 75 mg/day, 100 mg/day, 150 mg/day, 200 mg/day, 250 mg/day, 300 mg/day, or 350 mg/day.

Monotherapy

In an embodiment, the effective amount of a Cdc7 inhibitor is administered as a monotherapy.

In some aspects, the effective amount of the Cdc7 inhibitor monotherapy is less than a maximum tolerated dose (MTD). In some aspects, the effective amount of the Cdc7 inhibitor monotherapy is less than 1000 mg/day, less than 500 mg/day, or less than 400 mg/day. In some aspects, the effective amount of the Cdc7 inhibitor monotherapy is less than 300 mg/day, less than 200 mg/day, less than 150 mg/day, less than 100 mg/day, or less than 75 mg/day. In some aspects, the effective amount of the Cdc7 inhibitor monotherapy is less than 324 mg/day. In some aspects, the effective amount of the SRA141 monotherapy is 324 mg/day. In some aspects, the effective amount of the Cdc7 inhibitor monotherapy is at least 10 mg/day. In some aspects, the effective amount of the Cdc7 inhibitor monotherapy is between 10-400 mg/day. In some aspects, the effective amount of the Cdc7 inhibitor monotherapy is between 10-324 mg/day. In some aspects, the effective amount of the Cdc7 inhibitor monotherapy is between 40-400 mg/day. In some aspects, the effective amount of the Cdc7 inhibitor monotherapy is at least 10 mg/day, at least 20 mg/day, at least 40 mg/day, at least 80 mg/day, at least 160 mg/day, or at least 320 mg/day. In some aspects, the effective amount of the Cdc7 inhibitor monotherapy is at least 15 mg/day, at least 25 mg/day, at least 50 mg/day, at least 75 mg/day, at least 100 mg/day, at least 150 mg/day, at least 200 mg/day, at least 250 mg/day, at least 300 mg/day, or at least 350 mg/day. In some aspects, the effective amount of the SRA141 monotherapy is 10 mg/day, 20 mg/day, 40 mg/day, 80 mg/day, 160 mg/day, 320 mg/day, 325 mg/day, 350 mg/day, or 400 mg/day. In some aspects, the effective amount of the SRA141 monotherapy is 15 mg/day, 25 mg/day, 50 mg/day, 75 mg/day, 100 mg/day, 150 mg/day, 200 mg/day, 250 mg/day, 300 mg/day, or 350 mg/day.

Combination Therapy

Also disclosed herein, the methods of the invention include a combination therapy administering an effective amount of SRA141 and coadministering a second effective amount of one or more additional treatments.

Additional treatments include, but are not limited to, administering a chemotherapeutic agent, administering an antibody or antibody fragment (such as an immune checkpoint inhibitors), administering a radiation treatment, and administering a combination thereof. Additional treatments also include, but are not limited to, administering an anti-neoplastic agent, such as a DNA polymerase inhibitor, a receptor tyrosine kinase inhibitor, a mammalian target of rapamycin (mTOR) pathway inhibitor. Anti-neoplastic agents can also include a mitogen activated protein kinase (MAPK) pathway inhibitor, such as Trametinib. Anti-neoplastic agents can also include a retinoid pathway regulator, such as is the RXR agonist Bexarotene, and the RAR agonist Tretinoin. Anti-neoplastic agents can also include an apoptosis regulator, such as comprises an apoptosis inducer, including, but not limited, to an anti-Bcl-2 agent (e.g., ABT-199). Anti-neoplastic agents can also include phosphatidylinositol-4,5-bisphosphate 3 kinase (PI3K) pathway inhibitors, such as Copanlisib. Anti-neoplastic agents can also include PARP inhibitors, such as BMN673. Anti-neoplastic agents can also include ATM kinase inhibitors, such as KU-60019. Anti-neoplastic agents can also include Aurora B kinase inhibitors, such as Barasertib. Anti-neoplastic agents can also include tyrosine threonine kinase (TTK) inhibitors, such as an inhibitor of monopolar spindle 1 kinase (Mpsl) (e.g., CFI-402257). Anti-neoplastic agents can also include inhibitors of epidermal growth factor (EGF), such as Erlotinib. In some embodiments the anti-neoplastic agent is gemcitabine. In some embodiments that anti-neoplastic agent is not gemcitabine.

Additional treatments can also include a combination of additional treatments, such as a combination of anti-neoplastic agents.

In specific embodiments of the invention, the effective amount of SRA141 is administered to a subject as a combination therapy with a second effective amount of a additional treatment. In some aspects, the second effective amount is an amount from about 0.001 mg/kg to about 15 mg/kg. In some embodiments the second effective amount of the additional treatment is 0.001, 0.005, 0.010, 0.020, 0.050, 0.1, 0.2, 0.5, 1.0, 2.0, 5.0, 10.0 or 15.0 mg/kg. In some embodiments the second effective amount of the additional treatment is between 10-2000 $mg/m^2$/day. In some embodiments the second effective amount of the additional treatment is between 50-1250 $mg/m^2$/day. In some embodiments the second effective amount of the additional treatment is 50 $mg/m^2$/day, 100 $mg/m^2$/day, 150 $mg/m^2$/day, 200 $mg/m^2$/day, 300 $mg/m^2$/day, 400 $mg/m^2$/day, 500 $mg/m^2$/day, 600 $mg/m^2$/day, 700 $mg/m^2$/day, 800 $mg/m^2$/day, 900 $mg/m^2$/day, 1000 $mg/m^2$/day, 1100 $mg/m^2$/day, or 1250 $mg/m^2$/day.

Coadministered encompasses methods where SRA141 and the additional treatment are given simultaneously, where SRA141 and the additional treatment are given sequentially, and where either one of, or both of, SRA141 and the additional treatment are given intermittently or continuously, or any combination of: simultaneously, sequentially, intermittently and/or continuously. The skilled artisan will recognize that intermittent administration is not necessarily the same as sequential because intermittent also includes a first administration of an agent and then another administration later in time of that very same agent. Moreover, the skilled artisan understands that intermittent administration also encompasses sequential administration in some aspects because intermittent administration does include interruption of the first administration of an agent with an administration of a different agent before the first agent is administered again. Further, the skilled artisan will also know that continuous administration can be accomplished by a number of routes including intravenous drip or feeding tubes, etc.

Furthermore, and in a more general way, the term "coadministered" encompasses any and all methods where the individual administration of a Cdc7 inhibitor and the individual administration of the additional treatment to a subject overlap during any timeframe.

Dosing Route

In some aspects, the present disclosure provides for methods where either one of, or both of, or any combination thereof, SRA141 and/or a additional treatment are administered by a route selected from the group consisting of: intravenous, subcutaneous, cutaneous, oral, intramuscular, and intraperitoneal. In some aspects, the present disclosure provides for methods where either one of, or both of, or any combination thereof, SRA141 and/or a additional treatment are administered intravenously. In some aspects, the present disclosure provides for methods where either one of, or both of, or any combination thereof, SRA141 and/or a additional treatment are administered orally.

It is understood by the skilled artisan that the unit dose forms of the present disclosure may be administered in the same or different physicals forms, i.e., orally via capsules or tablets and/or by liquid orally or via intravenous infusion, and so on. Moreover, the unit dose forms for each administration may differ by the particular route of administration. Several various dosage forms may exist for either one of, or both of, a Cdc7 inhibitor and an additional treatment. Because different medical conditions can warrant different routes of administration, the same components of a combination of a Cdc7 inhibitor and an additional treatment described herein may be exactly alike in composition and physical form and yet may need to be given in differing ways and perhaps at differing times to alleviate the condition. For example, a condition such as persistent nausea, especially with vomiting, can make it difficult to use an oral dosage form, and in such a case, it may be necessary to administer another unit dose form, perhaps even one identical to other dosage forms used previously or afterward, with an inhalation, buccal, sublingual, or suppository route instead or as well. The specific dosage form may be a requirement for certain combinations of SRA141 and a additional treatment, as there may be issues with various factors like chemical stability or pharmacokinetics.

Dosing Schedule

In one aspect, the frequency of administration of SRA141 or the additional treatment to a subject includes, but is not limited to, Q1d, Q2d, Q3d, Q4d, Q5d, Q6d, Q7d, Q8d, Q9d, Q10d, Q14d, Q21d, Q28d, Q30d, Q90d, Q120d, Q240d, or Q365d. The term "QnD or qnd" refers to drug administration once every "n" days. For example, QD (or qd) refers to once every day or once daily dosing, Q2D (or q2d) refers to a dosing once every two days, Q7D refers to a dosing once every 7 days or once a week, Q5D refers to dosing once every 5 days, and so on. In one aspect, SRA141 and the additional treatment are administered on different schedules.

In another aspect, the frequency of administration of SRA141 or the additional treatment to a subject includes, but is not limited to: 5 days of dosing followed by 2 days of non-dosing each week; 1 week of daily dosing followed by 1, 2, or 3 weeks of non-dosing; 2 or 3 weeks of daily dosing followed by 1, or 2 weeks of non-dosing; twice daily dosing; or dosing on days 2 and 3 of a weekly cycle. In one aspect, SRA141 and the additional treatment are administered on different schedules.

In one aspect, the present disclosure provides for methods where either one of or both of or any combination thereof SRA141 and/or the additional treatment are administered intermittently. In one aspect, the present disclosure provides for methods comprising administering either one of, or both of, or any combinations thereof, SRA141 or the additional treatment, to a subject with at least ten (10) minutes, fifteen (15) minutes, twenty (20) minutes, thirty (30) minutes, forty (40) minutes, sixty (60) minutes, two (2) hours, three (3) hour, four (4) hours, six (6) hours, eight (8) hours, ten (10) hours, twelve (12) hours, fourteen (14) hours, eighteen (18) hours, twenty-four (24) hours, thirty-six (36) hours, forty-eight (48) hours, three (3) days, four (4) days, five (5) days, six (6) days, seven (7) days, eight (8) days, nine (9) days, ten (10) days, eleven (11) days, twelve (12) days, thirteen (13) days, fourteen (14) days, three (3) weeks, or four (4) weeks, delay between administrations. In such aspects, the administration with a delay follows a pattern where one of or both of or any combination thereof SRA141 and/or the additional treatment are administered continuously for a given period of time from about ten (10) minutes to about three hundred and sixty five (365) days and then is not administered for a given period of time from about ten (10) minutes to about thirty (30) days. In one aspect, the present disclosure provides for methods where either one of or any combination of SRA141 and/or the additional treatment are administered intermittently while the other is given continuously.

In one aspect, the present disclosure provides for methods where the combination of the effective amount of SRA141 is administered sequentially with the second effective amount of an additional treatment.

In one aspect, the present disclosure provides for methods where SRA141 and the additional treatment are administered simultaneously. In one aspect, the present disclosure provides for methods where the combination of the effective amount of SRA141 is administered sequentially with the second effective amount of an additional treatment. In such aspects, the combination is also said to be "coadministered" since the term includes any and all methods where the subject is exposed to both components in the combination. However, such aspects are not limited to the combination being given just in one formulation or composition. It may be that certain concentrations of SRA141 and the additional treatment are more advantageous to deliver at certain intervals and as such, the effective amount of SRA141 and the second effective amount of the additional treatment may change according to the formulation being administered.

In some aspects, the present disclosure provides for methods wherein SRA141 and the additional treatment are administered simultaneously or sequentially. In some aspects, the present disclosure provides for methods where the effective amount of SRA141 is administered sequentially after the second effective amount of the additional treatment. In some aspects, the present disclosure provides for methods where the second effective amount of the additional treatment is administered sequentially after the effective amount of SRA141.

In some aspects, the present disclosure provides for methods where the combination is administered in one formulation. In some aspects, the present disclosure provides for methods where the combination is administered in two (2) compositions where the effective amount of SRA141 is administered in a separate formulation from the formulation of the second effective amount of the additional treatment.

In some aspects, the present disclosure provides for methods where the effective amount of SRA141 is administered sequentially after the second effective amount of the additional treatment. In some aspects, the present disclosure provides for methods where the second effective amount of the additional treatment is administered sequentially after the effective amount of SRA141. In some aspects, the SRA141 and the additional treatment are administered; and subsequently both SRA141 and the additional treatment are administered intermittently for at least twenty-four (24) hours. In some aspects, SRA141 and the additional treatment are administered on a non-overlapping every other day schedule. In some aspects, the additional treatment is administered on day 1, and SRA141 is administered on days 2 and 3 of a weekly schedule.

In some aspects, the present disclosure provides for methods where the effective amount of SRA141 is administered no less than four (4) hours after the second effective amount of the additional treatment. In one aspect, the present disclosure provides for methods where the effective amount of SRA141 is administered no less than ten (10) minutes, no less than fifteen (15) minutes, no less than twenty (20) minutes, no less than thirty (30) minutes, no less than forty (40) minutes, no less than sixty (60) minutes, no less than one (1) hour, no less than two (2) hours, no less than four (4) hours, no less than six (6) hours, no less than eight (8) hours, no less than ten (10) hours, no less than twelve (12) hours, no less than twenty four (24) hours, no less than two (2) days, no less than four (4) days, no less than six (6) days, no less than eight (8) days, no less than ten (10) days, no less than twelve (12) days, no less than fourteen (14) days, no less than twenty one (21) days, or no less than thirty (30) days after the second effective amount of the additional treatment. In one aspect, the present disclosure provides for methods where the second effective amount of the additional treatment is administered no less than ten (10) minutes, no less than fifteen (15) minutes, no less than twenty (20) minutes, no less than thirty (30) minutes, no less than forty (40) minutes, no less than sixty (60) minutes, no less than one (1) hour, no less than two (2) hours, no less than four (4) hours, no less than six (6) hours, no less than eight (8) hours, no less than ten (10) hours, no less than twelve (12) hours, no less than twenty four (24) hours, no less than two (2) days, no less than four (4) days, no less than six (6) days, no less than eight (8) days, no less than ten (10) days, no less than twelve (12) days, no less than fourteen (14) days, no less than twenty one (21) days, or no less than thirty (30) days after the effective amount of a SRA141.

Cancers and Tumors

Methods are disclosed for the treatment of cancer. Accordingly, the present disclosure provides for methods of treating a cancer in a subject in need thereof (i.e., a subject with cancer or a subject suffering from cancer), the method comprising administering an effective amount of SRA141 to the subject with cancer, wherein the cancer is melanoma, uterine cancer, thyroid cancer, blood cancer, bladder cancer, breast cancer, cervical cancer, colorectal cancer (CRC), gastric cancer, endometrial cancer, cholangiocarcinoma, hepatocellular cancer, leukemia, lymphoma, myeloma, non-small cell lung cancer, ovarian cancer, prostate cancer, pancreatic cancer, brain cancer, sarcoma, small cell lung cancer, neuroblastoma, or head and neck cancer. In some aspects, the cancer is a blood cancer, such as acute myeloid leukemia (AML), chronic myelogenous leukemia (CML), chronic eosinophilic leukemia, and diffuse large B-cell lymphoma (DLBCL). In some aspects, the cancer is AML.

In some aspects, the cancer can be categorized as not having a microsatellite instability high (MSI-H) status. The term "microsatellite instability" refers to tumors that are characterized by having genomic instability in specific repetitive DNA sequences (e.g., short tandem repeats or simple sequence repeats). Methods for detection of microsatellite instability include any methods known in the art including, but not limited to, those methods described in Wang M. et al., Screening for Microsatellite Instability in Colorectal Cancer and Lynch Syndrome—A Mini Review; N A J Med Sci. 2016; 9(1):5-11. In certain embodiments, microsatellite instability is characterized by detection of mononucleotide repeat markers (e.g., BAT-25, BAT-26, NR-21, NR-24 and MONO-27, also known as the Promega MSI Multiplex System). In certain embodiments, microsatellite instability is characterized by detection of quasimonomorphic markers and dinucleotide repeat markers (e.g., BAT25, BAT26, D2S123, D5S346, and D17S250, also known as the Bathesda Panel). MSI can be classified as MSI-high (MSI-H), MSI-Low (MSI-L), and MS-Stable (MSS) using where instability in two or more markers is classified as MSI-H, instability in one only as MSI-L, and no observed instability in the five markers as MSS. MSI can be also classified as MSI-H if greater than 30% of markers tested demonstrate instability (MSI-H), MSI-L if 10-30% of markers tested demonstrate instability, and MSS if less than 10% of markers tested demonstrate instability. MSI status can be tested using 5, 6, 7, 8, 9, 10, or greater than 10 markers. In some embodiments, the cancer is categorized as MSS. The cancer can also have an unknown MSI status, i.e., the tumor is not known to have an MSI-H status.

The term "microsatellite instability" in certain embodiments also refers to tumors that are characterized by having one or more repetitive DNA sequences known in the art to be correlated with loss of mismatch repair (MMR) compared to at least one reference sample.

In some aspects, the present disclosure provides for methods of inhibiting the growth of a tumor wherein the tumor is from a cancer that is melanoma, uterine cancer, thyroid cancer, blood cancer, bladder cancer, breast cancer, cervical cancer, colorectal cancer (CRC), gastric cancer, endometrial cancer, cholangiocarcinoma, hepatocellular cancer, leukemia, lymphoma, myeloma, non-small cell lung cancer, ovarian cancer, prostate cancer, pancreatic cancer, brain cancer, sarcoma, small cell lung cancer, neuroblastoma, or head and neck cancer. The tumor can be from a blood cancer, such as acute myeloid leukemia (AML), chronic myelogenous leukemia (CML), chronic eosinophilic leukemia, and diffuse large B-cell lymphoma (DLBCL). The tumor can be from an AML cancer. The tumor can be from a metastatic colorectal cancer (mCRC). The tumor can be from a metastatic colorectal cancer (mCRC) not categorized as having an MSI-H status. The tumor can have a Wnt signaling pathway mutation, such as an Adenomatous polyposis coli (APC) gene mutation, a FAT1 mutation, a FAT4 mutation, or combinations thereof. The tumor can have a FBXW7 mutation.

In some aspects, the tumor associated with the cancer comprises a phenotype that is prospectively screened by using either an archival or a fresh tumor biopsy and examining the pattern of chromosome separation by employing histochemical staining of tumor sections with hematoxylin and eosin (or similar stains) and determining whether the tumor exhibits aberrant mitosis (e.g., lagging chromosomes, anaphase bridges, multipolar spindles), such as upon examination under a microscope either manually or by automated methods. In some aspects, a pharmacodynamic marker of aberrant mitosis is determined by histochemical staining using post-treatment tumor biopsies after SRA141 administration. Post treatment biopsies can be obtained several days after SRA141 administration, such as the same day biopsies are obtained for pMCM2 monitoring (see below).

Subjects

The present disclosure provides for administering an effective amount of SRA141 to a subject that is in need thereof. The present disclosure provides for administering an effective amount of SRA141 in a combination therapy with a additional treatment to a subject that is in need thereof. In some aspects, the tumor from a subject is screened with genetic testing and/sequencing prior to administration. In some aspects, the tumor from a subject is screened with genetic testing and/sequencing after administration. In some aspects, the tumor from a subject is screened both after and before administration. In some aspects, healthy cells from the subject are screened with genetic testing and/sequencing prior to administration, after administration, or both. In some aspects, the tumor from a subject is screened with other biological tests or assays to determine the level of expression of certain biomarkers, such as microsatellites or repetitive DNA. In some aspects, the tumor from a subject is screened with both genetic testing and/sequencing and other biomarker tests or assays.

In some aspects, the present disclosure provides for methods wherein the subject is a mammal. In some aspects, the present disclosure provides for methods wherein the subject is a primate.

In some aspects, the present disclosure provides for methods wherein the subject is a mouse.

In some aspects, the present disclosure provides for methods wherein the subject is a human.

In some aspects, the present disclosure provides for methods wherein the tumor is in a human suffering from cancer that is selected from the group consisting of: melanoma, uterine cancer, thyroid cancer, blood cancer, bladder cancer, breast cancer, cervical cancer, colorectal cancer (CRC), gastric cancer, endometrial cancer, cholangiocarcinoma, hepatocellular cancer, leukemia, lymphoma, myeloma, non-small cell lung cancer, ovarian cancer, prostate cancer, pancreatic cancer, brain cancer, sarcoma, small cell lung cancer, neuroblastoma, or head and neck cancer. In some aspects, the cancer is a blood cancer, such as acute myeloid leukemia (AML), chronic myelogenous leukemia (CML), chronic eosinophilic leukemia, and diffuse large B-cell lymphoma (DLBCL). In some aspects, the cancer is AML. In some aspects, the cancer is metastatic colorectal cancer (mCRC). The mCRC can be categorized as not having a MSI-H status.

In some aspects, subjects have tumors that harbor genomic alterations expected to confer sensitivity to Cdc7 inhibition, such as not having a MSI-H status, having a chromosome instability (CIN) phenotype (e.g., a CRC CIN phenotype is generally mutually exclusive from microsatellite unstable (MSI) CRC tumors), a spindle checkpoint assembly defect, a mitosis defect, a G1/S checkpoint defect, having a Wnt signaling pathway mutation (e.g., an Adenomatous polyposis coli (APC) gene mutation, a FAT1 mutation, a FAT4 mutation, or combinations thereof), or combinations thereof.

Pharmacokinetics

The methods described herein for the treatment of cancer can result in a plasma $C_{max}$ greater than 400 ng/mL, greater than 600 ng/mL, greater than 1000 ng/mL, or greater than 1400 ng/mL of the SRA141 compound. The methods described herein for the treatment of cancer can result in a in a plasma $C_{max}$ of at least 500 ng/mL, at least 600 ng/mL, at least 700 ng/mL, at least 800 ng/mL, at least 900 ng/mL, at least 1000 ng/mL, at least 1100 ng/mL, at least 1100 ng/mL, at least 1200 ng/mL, at least 1300 ng/mL, at least 1400 ng/mL, or at least 1500 ng/mL of the SRA141 compound.

The methods described herein for the treatment of cancer can result in a in an $AUC_{last}$ greater than 3000 ng·h/mL, greater than 5800 ng·h/mL, greater than 11900 ng·h/mL, or greater than 16400 ng·h/mL of the SRA141 compound. The methods described herein for the treatment of cancer can result in a in an $AUC_{last}$ of at least 5000 ng·h/mL, at least 6000 ng·h/mL, at least 7000 ng·h/mL, at least 8000 ng·h/mL, at least 9000 ng·h/mL, at least 10000 ng·h/mL, at least 11000 ng·h/mL, at least 12000 ng·h/mL, at least 13000 ng·h/mL, at least 14000 ng-h/mL, at least 15000 ng-h/mL, or at least 16000 ng-h/mL of the SRA141 compound.

The methods described herein for the treatment of cancer can result in a in an intra-tumoral concentration of greater than 500 ng/mL, greater than 600 ng/mL, greater than 900 ng/mL, or greater than 1300 ng/mL of the SRA141 compound. The methods described herein for the treatment of cancer can result in a in an intra-tumoral concentration of at least 500 ng/mL, at least 600 ng/mL, at least 700 ng/mL, at least 800 ng/mL, at least 900 ng/mL, at least 1000 ng/mL, at least 1100 ng/mL, at least 1100 ng/mL, at least 1200 ng/mL, at least 1300 ng/mL, at least 1400 ng/mL, or at least 1500 ng/mL of the SRA141 compound.

Kinase Inhibition

In some embodiments, the methods described herein result in in vivo kinase inhibition, e.g., inhibition of MCM2 phosphorylation. As is known in the art, prior to entering S phase and subsequent DNA replication, multiple origins of replication are established across the genome. These origins of replication are composed of multiple components including six mini-chromosome maintenance proteins (MCM2-7) collectively referred to as the pre-replication complex (pre-RC). Once the pre-RC is established, Cdc7 phosphorylates MCM2, which initiates S phase entry and DNA replication. As S phase progresses, Cdc7 phosphorylates MCM2 at additional replication origins until DNA replication is completed prior to entering the next phase of the cell cycle. Consequently, MCM2 phosphorylation can be used as a surrogate marker for Cdc7 activity.

Disclosed herein are methods for the treatment of cancer resulting in in vivo inhibition of MCM2 phosphorylation, such phosphorylation at amino acid residues Ser40 or Ser53. The in vivo inhibition of MCM2 phosphorylation can be in a tumor associated with the cancer. The in vivo inhibition of MCM2 phosphorylation in a tumor can be at least 50% relative to an untreated tumor sample. The in vivo inhibition of MCM2 phosphorylation in a tumor can be at least 10%, 20%, 30%, 40%, 50%, 60%, 70%, 80%, or 90% relative to an untreated tumor sample. The in vivo inhibition of MCM2 phosphorylation can be in skin of a subject. In vivo inhibition of MCM2 phosphorylation can be measured by assays known to those skilled in the art including, but not limited to, Western blot analysis, immunohistochemistry (IHC), liquid chromatography-mass spectrometry (LC/MS), or LC/MS/MS. In vivo inhibition of MCM2 phosphorylation can be measured in a biopsy of the subject.

The methods described herein for the treatment of cancer may not result in (i.e., may avoid) specific inhibition of an off target kinase in the subject, wherein the off target kinase is selected from the group consisting of: WEE1, CDK7, CDK8, CDK9, and LATS2. The methods described herein for the treatment of cancer can result in less than 90% inhibition of an off-target kinase.

Tumor Inhibition

The present disclosure is directed to methods using an effective amount of the compound, e.g., SRA141, to inhibit the progression of, reduce the size in aggregate of aggregation of, reduce the volume of, reduce the diameter of, and/or otherwise inhibit the growth of a tumor. Accordingly, the methods described herein for the treatment of cancer can result in growth inhibition of a tumor associated with a cancer. The methods described herein for the treatment of cancer can result in cytotoxicity of a tumor associated with a cancer. The methods described herein for the treatment of cancer can result in growth inhibition and cytotoxicity of a tumor associated with a cancer. The methods described herein for the treatment of cancer can result in growth inhibition or cytotoxicity of a tumor associated with a cancer. The methods described herein for the treatment of cancer can result in a regression of a tumor associated with the cancer, including a complete regression or a partial regression. Also provided herein are methods of treating the underlying disease, e.g., cancer, and extending the survival of the subject.

In one embodiment provided for is a method of inhibiting the growth of a tumor in a subject in need thereof, the method comprising administering to the subject an effective amount of SRA141. In some aspects, the disclosure provides for a method of administering to the subject an effective amount of SRA141 to inhibit growth of a tumor, wherein tumor growth is reduced by at least 47%. In some aspects, the disclosure provides for a method of administering to the subject an effective amount of SRA141 to inhibit growth of a tumor, wherein tumor growth is reduced by at least 93%. In some aspects, the disclosure provides for a method of administering to the subject an effective amount of SRA141 to inhibit growth of a tumor, wherein tumor growth is reduced by 1%, 2%, 3%, 4%, 5%, 6%, 7%, 8%, 9%, 10%, 12%, 14%, 16%, 18%, 20%, 22%, 24%, 26%, 28%, 30%, 32%, 34%, 36%, 38%, 40%, 42%, 44%, 46%, 48%, 50%, 52%, 54%, 56%, 58%, 60%, 62%, 64%, 66%, 68%, 70%, 72%, 74%, 76%, 78%, 80%, 82%, 84%, 86%, 88%, 90%, 92%, 94%, 96%, 98%, or 100% as measured by tumor volume. In some aspects, the disclosure provides for a method of administering to the subject an effective amount of SRA141 to inhibit growth of a tumor, wherein tumor growth is reduced by 1%, 2%, 3%, 4%, 5%, 6%, 7%, 8%, 9%, 10%, 12%, 14%, 16%, 18%, 20%, 22%, 24%, 26%, 28%, 30%, 32%, 34%, 36%, 38%, 40%, 42%, 44%, 46%, 48%, 50%, 52%, 54%, 56%, 58%, 60%, 62%, 64%, 66%, 68%, 70%, 72%, 74%, 76%, 78%, 80%, 82%, 84%, 86%, 88%, 90%, 92%, 94%, 96%, 98%, or 100% as measured by the absolute size of the tumor. In some aspects, the disclosure provides for a method of administering to the subject an effective amount of SRA141 to inhibit the growth of a tumor, wherein tumor growth is reduced by 1%, 2%, 3%, 4%, 5%, 6%, 7%, 8%, 9%, 10%, 12%, 14%, 16%, 18%, 20%, 22%, 24%, 26%, 28%, 30%, 32%, 34%, 36%, 38%, 40%, 42%, 44%, 46%, 48%, 50%, 52%, 54%, 56%, 58%, 60%, 62%, 64%, 66%, 68%, 70%, 72%, 74%, 76%, 78%, 80%, 82%, 84%, 86%, 88%, 90%, 92%, 94%, 96%, 98%, or 100% as measured by the expression levels of tumor markers for that type of tumor. The present disclosure is also directed to methods using an effective amount of the compound SRA141 and a second effective amount of an additional treatment to inhibit the progression of, reduce the size in aggregation of, reduce the volume of, reduce the diameter of, and/or otherwise inhibit the growth of a tumor. Also provided herein are methods of treating the underlying disease, e.g., cancer, and extending the survival of the subject.

In one embodiment provided for is a method of inhibiting the growth of a tumor in a subject in need thereof, the method comprising administering to the subject an effective amount of SRA141 and a second effective amount of an additional treatment. In some aspects, the disclosure provides for a method of administering to the subject an effective amount of SRA141 and a second effective amount of an additional treatment to inhibit growth of a tumor, wherein tumor growth is reduced by 1%, 2%, 3%, 4%, 5%, 6%, 7%, 8%, 9%, 10%, 12%, 14%, 16%, 18%, 20%, 22%, 24%, 26%, 28%, 30%, 32%, 34%, 36%, 38%, 40%, 42%, 44%, 46%, 48%, 50%, 52%, 54%, 56%, 58%, 60%, 62%, 64%, 66%, 68%, 70%, 72%, 74%, 76%, 78%, 80%, 82%, 84%, 86%, 88%, 90%, 92%, 94%, 96%, 98%, or 100% as measured by tumor volume. In some aspects, the disclosure provides for a method of administering to the subject an effective amount of SRA141 and a second effective amount of an additional treatment to inhibit growth of a tumor, wherein tumor growth is reduced by 1%, 2%, 3%, 4%, 5%, 6%, 7%, 8%, 9%, 10%, 12%, 14%, 16%, 18%, 20%, 22%, 24%, 26%, 28%, 30%, 32%, 34%, 36%, 38%, 40%, 42%, 44%, 46%, 48%, 50%, 52%, 54%, 56%, 58%, 60%, 62%, 64%, 66%, 68%, 70%, 72%, 74%, 76%, 78%, 80%, 82%, 84%, 86%, 88%, 90%, 92%, 94%, 96%, 98%, or 100% as measured by the absolute size of the tumor. In some aspects, the disclosure provides for a method of administering to the subject an effective amount of SRA141 and a second effective amount of an additional treatment to inhibit growth of a tumor, wherein tumor growth is reduced by 1%, 2%, 3%, 4%, 5%, 6%, 7%, 8%, 9%, 10%, 12%, 14%, 16%, 18%, 20%, 22%, 24%, 26%, 28%, 30%, 32%, 34%, 36%, 38%, 40%, 42%, 44%, 46%, 48%, 50%, 52%, 54%, 56%, 58%, 60%, 62%, 64%, 66%, 68%, 70%, 72%, 74%, 76%, 78%, 80%, 82%, 84%, 86%, 88%, 90%, 92%, 94%, 96%, 98%, or 100% as measured by the expression levels of tumor markers for that type of tumor.

Clinical Endpoints

Provided herein are methods for treating cancer, e.g., inhibiting the growth of a tumor in a subject and/or inhibiting growth of a tumor cell, wherein the method results in a clinically relevant endpoint.

Tumor growth occurs when one or more biological cells grow and divide much more rapidly resulting in an increase in the number of cells in comparison to the normal and healthy process of cells division. This phenomenon is an indication that the cells are in a disease state such as cancer or pre-cancer. Moreover, tumor growth oftentimes comes about in discrete stages prior to the agglomerated cells forming a tumor.

There are several methods the skilled artisan can use to measure cell replication rates. The overall metabolic activity inside a cell can be measured via a labeled biological product. For example, there are several commercially available dyes (e.g., MTT) that can penetrate the cell and interact with certain enzymes and other factors to produce a detectable product. Also, cellular biomarkers can be measured in a cell. For example a BrdU assay can incorporate a thymidine derivative into cellular DNA and be detected with an antibody. Proliferating cell nuclear antigen (PCNA) is another such biomarker for detection. Besides tagging techniques, the skilled artisan can also use for example, microscopy or flow cytometry to allow for cell counts.

In one aspect, cellular replication is measured by a clinical endpoint that includes: a quality of life (QOL) score, duration of response (DOR, clinical benefit rate (CBR), patient reported outcomes (PRO), an objective response rate (ORR) score, a disease-free survival (DFS) or progression-free survival (PFS), a time to progression (TTP), an Overall Survival, a time-to-treatment failure (TTF), RECIST criteria, Partial Response (PR), Stable Disease (SD), Progressive Disease (PD) and/or a Complete Response (CR). The clinical endpoints can be determined using methods well known to one of skill in the art.

In some aspects, CR is disappearance of all target lesions wherein any pathological lymph nodes (either target or non-target) are reduced in short axis to <10 mm. In some aspects, PR is at least a 30% decrease in the sum of diameters of target lesions in reference to the baseline sum diameters. In some aspects, PD is at least a 20% increase in the sum of diameters of target lesions, taking as reference the smallest sum (including the baseline sum if it is the smallest). In some aspects, the sum may demonstrate an absolute increase of at least 5 mm in addition to the relative increase of 20%. In some aspects, SD is neither sufficient shrinkage to qualify of PR nor sufficient increase to qualify for PD, taking as reference the smallest sum diameters.

In some aspects, the present disclosure provides methods wherein the growth of the tumor is reduced at least about 5, 10, 20, 30, 40, 50, 60, 80, 90, 95, 97, 99, or 99.9% after administration of the effective amount of SRA141.

In some aspects, the present disclosure provides methods wherein the % reduction is calculated based on measurement (s) of one or more clinical endpoints.

In some aspects, the present disclosure provides methods wherein the growth of the tumor is reduced as measured by an increase or a decrease in total cell count in a MTT assay, or by change in genetic profile as measured by a ctDNA assay, by no more than or at least 5, 10, 20, 30, 40, 50, 60, 80, 90, 95, 97, 99, or 99.9% after administration of the effective amount of SRA141.

In some general aspects, the present disclosure provides methods wherein the growth of the tumor is reduced at least 5, 10, 20, 30, 40, 50, 60, 80, 90, 95, 97, 99, or 99.9% after administration of the effective amount of SRA141. In some aspects, the present disclosure provides methods wherein the growth of the tumor is reduced as measured by an increase or a decrease in total cell count in a MTT assay, or by change in genetic profile as measured by a ctDNA assay, by at least 5, 10, 20, 30, 40, 50, 60, 80, 90, 95, 97, 99, or 99.9% after administration of the effective amount of SRA141.

In some aspects, the present disclosure provides methods wherein administration results in an $IC_{50}$ value below 10 μM and/or a $GI_{50}$ value below 1 μM. In some aspects, the present disclosure provides methods wherein administration results in an $IC_{50}$ value below 10 μM and/or a $GI_{50}$ value below 1 μM at twenty-four (24) hours after administration. In some aspects, the present disclosure provides methods wherein administration results in an $IC_{50}$ value below 10 μM and/or a $GI_{50}$ value below 1 μM at forty-eight (48) hours after administration.

In some aspects, the present disclosure provides methods wherein the administration results in an AUC of at least 1, 10, 25, 50, 100, 200, 400, 600, 800, or 1000.

In some aspects, the present disclosure provides methods wherein the administration results in an $IC_{50}$ value of no more than 0.001, 0.005, 0.01, 0.05, 0.1, 1, 3, 5, 10, 20, 40, 50, 60, 80, 90, 100, 200, 250, 300, 350, or 400 μM.

In some aspects, the present disclosure provides methods wherein the administration results in an $EC_{50}$ value of at least 0.01, 0.1, 1, 3, 5, 10, 20, 40, 50, 60, 80, 90, 100, 200, 250, 300, 350, or 400 μM.

In some aspects, the present disclosure provides methods wherein the administration results in an therapeutic index (TI) value ranging from about 1.001:1 to about 50:1, about 1.1:1 to about 15:1, about 1.2:1 to about 12:1, about 1.2:1 to about 10:1, about 1.2:1 to about 5:1, or about 1.2:1 to about 3:1.

In some aspects, the present disclosure provides methods wherein the administration results in an $GI_{50}$ value of at least 0.1 μM, 0.3 μM, 0.5 μM, 0.7 μM, 1 μM, 1.5 μM, 2 μM, 2.5 μM, 3 μM, 4 μM, 5 μM, or 10 μM.

In some aspects, the present disclosure provides methods wherein the administration results in a Maximum Response Observed (Max Response) value of no more than 0.1, 0.5, 1, 2 μM, 2.5 μM, 3 μM, 4 μM, 5 μM, or 10 μM.

Tumor growth can be expressed in terms of total tumor volume. There exist formulas, both generally speaking and specific to certain tumor models, that the skilled artisan can use to calculate tumor volume based upon the assumption that solid tumors are more or less spherical. In this regard, the skilled artisan can use experimental tools such as: ultrasound imaging, manual or digital calipers, ultrasonography, computed tomographic (CT), microCT, $^{18}$F-FDG-microPET, or magnetic resonance imaging (MRI) to measure tumor volume. See for example Monga S P, Wadleigh R, Sharma A, et al. Intratumoral therapy of cisplatin/epinephrine injectable gel for palliation in patients with obstructive esophageal cancer. Am. J. Clin. Oncol. 2000; 23(4):386-392; Mary M. Tomayko C., Patrick Reynolds, 1989. Determination of subcutaneous tumor size in athymic (nude) mice. Cancer Chemotherapy and Pharmacology, Volume 24, Issue 3, pp 148-154; E Richtig, G Langmann, K Müllner, G Richtig and J Smolle, 2004. Calculated tumour volume as a prognostic parameter for survival in choroidal melanomas. Eye (2004) 18, 619-623; Jensen et al. BMC Medical Imaging 2008. 8:16; Tomayko et al. Cancer Chemotherapy and Pharmacology September 1989, Volume 24, Issue 3, pp 148-154; and Faustino-Rocha et al. Lab Anim (NY). 2013 June; 42(6):217-24, each of which are hereby incorporated by reference in their entirety.

In some aspects, the present disclosure provides methods wherein administration results in a reduction in tumor volume of at least 5, 10, 20, 30, 40, 50, 60, 80, 90, 95, 97, 99 or 99.9% after administration of the effective amount of SRA141. In some aspects, the present disclosure provides methods wherein administration results in a reduction in tumor size, as measured by medical imaging techniques, of at least 5, 10, 20, 30, 40, 50, 60, 80, 90, 95, 97, 99 or 99.9% after administration of the effective amount of SRA141.

In some aspects, the present disclosure provides methods wherein administration results in method where administration results in a reduction in tumor volume of at least 5% after one (1), two (2), three (3), four (4), six (6), eight (8), twelve (12), sixteen (16), twenty (20), twenty four (24), thirty six (36), or fifty two (52) weeks.

In order to assess objective response or tumor growth, the overall tumor burden at baseline may be estimated and used as a comparator for subsequent measurements. Measurable disease may be defined by the presence of at least one measurable lesion.

In some aspects, the present disclosure provides methods wherein when more than one measurable lesion is present at baseline all lesions up to a maximum of five lesions total (and a maximum of two lesions per organ) representative of all involved organs are identified as target lesions and are recorded and measured at baseline. In some aspects, target lesions are selected on the basis of their size (lesions with the longest diameter) and are representative of all involved organs. In some aspects, target lesions are those that lend themselves to reproducible repeated measurements. In some cases, the largest lesion does not lend itself to reproducible measurement in which circumstance the next largest lesion which can be measured reproducibly is selected, as exemplified in FIG. 3 Eisenhauer, et al. (2009).

Pathological lymph nodes may be defined as measurable and in some cases identified as target lesions when the node has a short axis of ≥15 mm by CT scan. In some embodiments the short axis of the nodes contributes to the baseline sum. In some embodiments the short axis of the node is the diameter used by radiologists to judge if a node is involved by solid tumor. In some embodiments, nodal size is reported as two dimensions in the plane in which the image is obtained (e.g., the axial plane for a CT scan; the axial, sagital, or coronal plane for an MRI scan, depending on the plane of acquisition of the scan). In some embodiments the smaller of the measures is the short axis. In some embodiments, pathological nodes with a short axis ≥10 mm but <15 mm are considered non-target lesions. In some embodiments, nodes that have a short axis <10 mm are considered non-pathological and are not recorded or followed.

In some aspects, a sum of the diameters (longest for non-nodal lesions, short axis for nodal lesions) for all target lesions is calculated and reported as the baseline sum diameters. In some aspects if lymph nodes are to be included in the sum, then only the short axis is added into the sum. In some aspects the baseline sum diameters are used as reference to characterize objective tumor growth or regression.

In some aspects, all other lesions or sites of disease (including pathological lymph nodes) are identified as non-target lesions and are recorded at baseline. In some cases measurements are not required and the lesions are followed as 'present,' 'absent,' or 'unequivocal progression.' In some cases, multiple non-target lesions involving the same organ may be recorded (e.g., 'multiple enlarged pelvic lymph nodes' or 'multiple liver metastases').

Therapeutically Effective Amount and Unit Dose Form

In general, the compounds of the present technology will be administered in a therapeutically effective amount by any of the accepted modes of administration for agents that serve similar utilities. The actual amount of the compound of the present technology, i.e., the active ingredient, will depend upon numerous factors such as the severity of the disease to be treated, the age and relative health of the subject, the potency of the compound used, the route and form of administration, and other factors well known to the skilled artisan. The drug can be administered at least once a day, preferably once or twice a day.

An effective amount of such agents can readily be determined by routine experimentation, as can the most effective and convenient route of administration and the most appropriate formulation. Various formulations and drug delivery systems are available in the art. See, e.g., Gennaro, A. R., ed. (1995) Remington's Pharmaceutical Sciences, 18th ed., Mack Publishing Co.

A therapeutically effective dose can be estimated initially using a variety of techniques well-known in the art. Initial doses used in animal studies may be based on effective concentrations established in cell culture assays. Dosage ranges appropriate for human subjects can be determined, for example, using data obtained from animal studies and cell culture assays.

An effective amount or a therapeutically effective amount or dose of an agent, e.g., a compound used in the methods described herein, e.g., the Cdc7 inhibitor SRA141, refers to that amount of the agent or compound that results in amelioration of symptoms or a prolongation of survival in a subject. Toxicity and therapeutic efficacy of such molecules can be determined by standard pharmaceutical procedures in cell cultures or experimental animals, e.g., by determining the $LD_{50}$ (the dose lethal to 50% of the population) and the $ED_{50}$ (the dose therapeutically effective in 50% of the population), and the minimum effective concentration (MEC) or minimum effective dose (MED). The dose ratio of toxic to therapeutic effects is therapeutic index, which can be expressed as the ratio of MTD or highest non-severely toxic dose (HNSTD) to MED. Agents that exhibit high therapeutic indices are preferred.

The effective amount or therapeutically effective amount is the amount of the compound or pharmaceutical composition that will elicit the biological or medical response of a tissue, system, animal or human that is being sought by the researcher, veterinarian, medical doctor or other clinician. Dosages particularly fall within a range of circulating concentrations that includes the $ED_{50}$ with little or no toxicity. Dosages may vary within this range depending upon the dosage form employed and/or the route of administration utilized. The exact formulation, route of administration, dosage, and dosage interval should be chosen according to methods known in the art, in view of the specifics of a subject's condition.

Dosage amount and interval may be adjusted individually to provide plasma levels of the active moiety that are sufficient to achieve the desired effects; i.e., the minimal effective concentration (MEC). The MEC will vary for each compound but can be estimated from, for example, in vitro data and animal experiments. Dosages necessary to achieve the MEC will depend on individual characteristics and route of administration. In cases of local administration or selective uptake, the effective local concentration of the drug may not be related to plasma concentration.

The amount of agent or composition administered may be dependent on a variety of factors, including the sex, age, and weight of the subject being treated, the severity of the affliction, the manner of administration, and the judgment of the prescribing physician.

A therapeutically effective amount can be the same or different than either one of, or both of, the effective amount of SRA141 and the second effective amount of the additional treatment. This is because the present disclosure provides that the methods, as described herein, are effective even where neither the effective amount of SRA141 nor the second effective amount of the additional treatment must be an amount that, alone, will ameliorate a symptom of a disease (e.g., the amount of the SRA141 and/or the additional treatment may be considered a "sub-therapeutic" amount if administered as an individual therapy). However, the present disclosure does provide that a therapeutically effective amount of the combination must be provided, i.e., the combination does at least affect a treatment of a symptom of a disease.

A unit dose form is a term that is generally understood by the skilled artisan. A unit dose forms is a pharmaceutical drug product that is marketed for a specific use. The drug product includes the active ingredient(s) and any inactive components, most often in the form of pharmaceutically acceptable carriers or excipients. It is understood that multiple unit dose forms are distinct drug products. Accordingly, one unit dose form may be e.g., the combination of SRA141 and an additional treatment of 250 mg at a certain ratio of each component, while another completely distinct unit dose form is e.g. the combination of SRA141 and an additional treatment of 750 mg at the same certain ratio of each component referred to above. So from one unit dose form to another, the effective amount of SRA141 and the second effective amount of the additional treatment may both remain the same. Of course when the either one of the effective amount of SRA141 or the second effective amount of the additional treatment changes, the unit dose form is distinct.

In some aspects, the effective amount is unique to the SRA141 compound, i.e., it is different than the second effective amount of the additional treatment. In some aspects, the effective amount of SRA141 is an amount that is equivalent to a "therapeutically effective amount" or an amount that brings about a therapeutic and/or beneficial effect. In some aspects, the effective amount of SRA141 is a "therapeutically effective amount". In some aspects, the second effective amount of the additional treatment is a "therapeutically effective amount". In some aspects, both the effective amount of SRA141 and second effective amount of the additional treatment are not a "therapeutically effective amount". In some aspects, the second effective amount is unique to the additional treatment, i.e., the second effective amount is a different amount for different additional treatments.

In some aspects, the SRA141 and the additional treatment combination is formulated in one (1) unit dose form. In some aspects, the same unit dose form is administered for at least four (4) hours, six (6) hours, eight (8) hours, twelve (12) hours, twenty four (24) hours, one (1) day, two (2) days, three (3) days, seven (7) days, ten (10) days, fourteen (14) days, twenty one (21) days, or thirty (30) days.

In some aspects, the SRA141 and the additional treatment combination is formulated in at least two (2) separately distinct unit dose forms. In some aspects, the first effective amount is different in the first unit dose form than in the second unit dose form. In some aspects, the effective amount of SRA141 is the same in the first unit dose form as it is in the second unit dose form.

In some aspects, the first unit dose form is the same as the second unit dose form. In some aspects, the first unit dose form is the same as the second and third unit dose forms. In some aspects, the first unit dose form is the same as the second, third, and fourth unit dose forms.

Compounds of the Invention

In one aspect, the present disclosure provides for methods of use of the compound SRA141.

SRA141

The compound SRA141 is also identified by the chemical name: Ethyl 5-(1H-pyrrolo[2,3-b]pyridin-3-yl)methylene 4-oxo-2-{[4-(2,2,2-trifluoroethyl)piperazinyl]amino-4,5-dihydrofuran-3-carboxylate.

SRA141 is a compound that is disclosed in International Patent Pub No. WO 2012133802, which is herein incorporated by reference for all that it teaches. The skilled artisan will find how to synthesize SRA141 in International Patent Pub No. WO 2012133802.

The SRA141 structure is shown below:

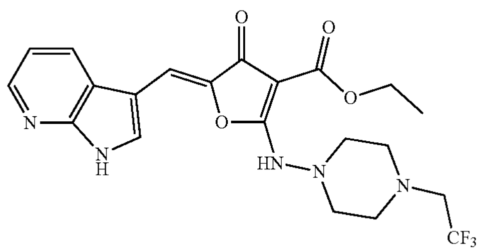 [SMILES: CCOC(=O)C1=C(NN2CCN(CC(F)(F)F)CC2)O/C(=C\c2c[nH]c3ncccc23)C1=O]

Pharmaceutical Compositions

Methods for inhibiting the growth of a tumor, inhibiting the progression of or treating cancer are described herein. Said methods include administering an effective amount of SRA141 and, optionally, a second effective amount of an additional treatment. The SRA141 and the additional treatment can each be formulated in pharmaceutical compositions. These pharmaceutical compositions may comprise, in addition to the active compound(s), a pharmaceutically acceptable excipient, carrier, buffer, stabilizer or other materials well known to those skilled in the art. Such materials should be non-toxic and should not interfere with the efficacy of the active ingredient. The precise nature of the carrier or other material can depend on the route of administration, e.g., oral, intravenous, cutaneous or subcutaneous, nasal, intramuscular, intraperitoneal routes.

Pharmaceutical compositions for oral administration can be in tablet, capsule, powder or liquid form. A tablet can include a solid carrier such as gelatin. Liquid pharmaceutical compositions generally include a liquid carrier such as water, petroleum derivative, animal or vegetable oils, mineral oil or synthetic oil. Physiological saline solution, dextrose or other saccharide solution or glycols such as ethylene glycol, propylene glycol or polyethylene glycol can be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives can be included, as required.

A composition can be administered alone or in combination with other treatments, either simultaneously or sequentially dependent upon the condition to be treated.

The present technology is not limited to any particular composition or pharmaceutical carrier, as such may vary. In general, compounds of the present technology will be administered as pharmaceutical compositions by any one of the following routes: oral, systemic (e.g., transdermal, intranasal or by suppository), or parenteral (e.g., intramuscular, intravenous or subcutaneous) administration. The preferred manner of administration is oral using a convenient daily dosage regimen that can be adjusted according to the degree of affliction. Compositions can take the form of tablets, pills, capsules, semisolids, powders, sustained release formulations, solutions, suspensions, elixirs, aerosols, or any other appropriate compositions. Another preferred manner for administering compounds of the present technology is inhalation.

The choice of formulation depends on various factors such as the mode of drug administration and bioavailability of the drug substance. For delivery via inhalation the compound can be formulated as liquid solution, suspensions, aerosol propellants or dry powder and loaded into a suitable dispenser for administration. There are several types of pharmaceutical inhalation devices-nebulizer inhalers, metered dose inhalers (MDI) and dry powder inhalers (DPI). Nebulizer devices produce a stream of high velocity air that causes therapeutic agents (which are formulated in a liquid form) to spray as a mist that is carried into the subject's respiratory tract. MDI's typically are formulation packaged with a compressed gas. Upon actuation, the device discharges a measured amount of therapeutic agent by compressed gas, thus affording a reliable method of administering a set amount of agent. DPI dispenses therapeutic agents in the form of a free flowing powder that can be dispersed in the subject's inspiratory air-stream during breathing by the device. In order to achieve a free flowing powder, therapeutic agent is formulated with an excipient such as lactose. A measured amount of therapeutic agent is stored in a capsule form and is dispensed with each actuation.

Pharmaceutical dosage forms of a compound of the present technology may be manufactured by any of the methods well-known in the art, such as, for example, by conventional mixing, sieving, dissolving, melting, granulating, dragee-making, tabletting, suspending, extruding, spray-drying, levigating, emulsifying, (nano/micro-) encapsulating, entrapping, or lyophilization processes. As noted above, the compositions of the present technology can include one or more physiologically acceptable inactive ingredients that facilitate processing of active molecules into preparations for pharmaceutical use.

Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of in general, a compound of the present technology in combination with at least one pharmaceutically acceptable excipient. Acceptable excipients are non-toxic, aid administration, and do not adversely affect therapeutic benefit of the claimed compounds. Such excipient may be any solid, liquid, semisolid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Compressed gases may be used to disperse a compound of the present technology in aerosol form. Inert gases suitable for this purpose are nitrogen, carbon dioxide, etc. Other suitable pharmaceutical excipients and their formulations are described in Remington's Pharmaceutical Sciences, edited by E. W. Martin (Mack Publishing Company, 18th ed., 1990).

In some embodiments, the pharmaceutical compositions include a pharmaceutically acceptable salt. The term "pharmaceutically acceptable salt" refers to salts derived from a variety of organic and inorganic counter ions well known in the art that include, by way of example only, sodium, potassium, calcium, magnesium, ammonium, and tetraalkylammonium, and when the molecule contains a basic functionality, salts of organic or inorganic acids, such as hydrochloride, hydrobromide, tartrate, mesylate, acetate, maleate, and oxalate. Suitable salts include those described in Stahl and Wermuth (Eds.), Handbook of Pharmaceutical Salts Properties, Selection, and Use; 2002.

The present compositions may, if desired, be presented in a pack or dispenser device containing one or more unit dosage forms containing the active ingredient. Such a pack or device may, for example, comprise metal or plastic foil, such as a blister pack, or glass, and rubber stoppers such as in vials. The pack or dispenser device may be accompanied by instructions for administration. Compositions comprising a compound of the present technology formulated in a compatible pharmaceutical carrier may also be prepared, placed in an appropriate container, and labeled for treatment of an indicated condition.

The amount of the compound in a formulation can vary within the full range employed by those skilled in the art. Typically, the formulation will contain, on a weight percent (wt %) basis, from about 0.01-99.99 wt % of a compound of the present technology based on the total formulation, with the balance being one or more suitable pharmaceutical excipients. Preferably, the compound is present at a level of about 1-80 wt %. Representative pharmaceutical formulations are described below.

Formulation Examples

The following are representative pharmaceutical formulations containing the SRA141 and an additional treatment, either alone or in combination.

A composition can be administered alone or in combination with other treatments, either simultaneously or sequentially dependent upon the condition to be treated.

Kits

The present disclosure also provides for a kit comprising the combination of SRA141 and, optionally, an additional treatment and instructions for use. The present disclosure further provides for a kit comprising one or more pharmaceutical compositions where the pharmaceutical composition(s) comprise SRA141 and an additional treatment, and instructions for use, optionally the combination includes at least one pharmaceutically acceptable carrier or excipient.

Individual components of the kit can be packaged in separate containers and, associated with such containers, can be a notice in the form prescribed by a governmental agency regulating the manufacture, use or sale of pharmaceuticals or biological products, which notice reflects approval by the agency of manufacture, use or sale. The kit may optionally contain instructions or directions outlining the method of use or administration regimen for the antigen-binding construct.

In some aspects, the disclosure provides for a kit comprising a combination of SRA141 and a additional treatment and at least one pharmaceutically acceptable carrier or excipient.

When one or more components of the kit are provided as solutions, for example an aqueous solution, or a sterile aqueous solution, the container means may itself be an inhalant, syringe, pipette, eye dropper, or other such like apparatus, from which the solution may be administered to a subject or applied to and mixed with the other components of the kit.

The components of the kit may also be provided in dried or lyophilized form and the kit can additionally contain a suitable solvent for reconstitution of the lyophilized components. Irrespective of the number or type of containers, the kits described herein also may comprise an instrument for assisting with the administration of the composition to a patient. Such an instrument may be an inhalant, nasal spray device, syringe, pipette, forceps, measured spoon, eye dropper or similar medically approved delivery vehicle.

In another aspect described herein, an article of manufacture containing materials useful for the treatment, prevention and/or diagnosis of the disorders described herein, e.g., inhibition of tumor growth is provided. The article of manufacture comprises a container and a label or package insert on or associated with the container. Suitable containers include, for example, bottles, vials, syringes, iv. solution bags, etc. The containers may be formed from a variety of materials such as glass or plastic. The container(s) holds a composition which is by itself or combined with another composition effective for treating, preventing and/or diagnosing the disorder and may have a sterile access port (for example the container may be an intravenous solution bag or a vial having a stopper pierceable by a hypodermic injection needle).

The article of manufacture in this embodiment described herein may further comprise a label or package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Polypeptides and Nucleic Acids

Described herein are polypeptide and nucleic acid sequences of genes useful for the methods described herein, e.g., genes for Cdc7. In some embodiments, polypeptide and nucleic acid sequences useful for the methods described herein are at least 95, 96, 97, 98, or 99% identical to sequences described herein or referred to herein by a database accession number. In some embodiments, polypeptide and nucleic acid sequences useful for the methods described herein are 100% identical to sequences described herein or referred to herein by a database accession number.

The term "percent identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the percent "identity" can exist over a region of the sequence being compared, e.g., over a functional domain, or, alternatively, exist over the full length of the two sequences to be compared. For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., Current Protocols in Molecular Biology (2003)). One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information (www.ncbi.nlm.nih.gov).

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences,* 18th Edition (Easton, Pennsylvania: Mack Publishing Company, 1990); Carey and Sundberg *Advanced Organic Chemistry* 3$^{rd}$ *Ed.* (Plenum Press) Vols A and B (1992).

Abbreviations

TABLE 1

| Abbreviations | |
|---|---|
| QD | Once a day |
| BID | Twice a day |
| BIW | Twice weekly |
| p.o. | Oral(ly) |
| i.p. | Intraperitoneal (ly) |
| RT | Room Temperature |
| BW | Body weight |
| BWL | Body weight loss |
| FFPE | Formalin Fixed Paraffin Embedded |
| SD | Standard deviation |
| SEM | Standard error of mean |

Example 1: SRA141 Treatment of Mouse AML Xenografts Models

The efficacy of a Cdc7 inhibitor (compound I-D, also named SRA141) alone as a monotherapy was tested in xenografts using an acute myeloid leukemia cell line, MV-4-11. Female BALB/c mice bearing MV-4-11 xenograft tumors were administered SRA141 at various doses. 60 female BALB/C mice aged 5-6 weeks were subcutaneously inoculated MV-4-11 tumor cells. Mice were inoculated with $5.0\times10^6$ cells (mixed with Matrigel® at a ratio of 1:1) per mouse. 32 mice were selected and randomized into 4 groups and were orally administered (i) vehicle control (0.2 M HCl/0.5% MC400) or (ii) SRA141 at 30 or 60 mg/kg BID for 3 weeks or (iii) SRA141 120 mg/kg QD for 3 weeks (n=8 per treatment group). The body weights of mice were recorded once per week before grouping and mice conditions were recorded daily during the treatment. After 21 days of dosing, mice were sacrificed for tumor weight measurement. Tumor growth inhibition was calculated on Day 21, the final day of the study.

Figure 1B:
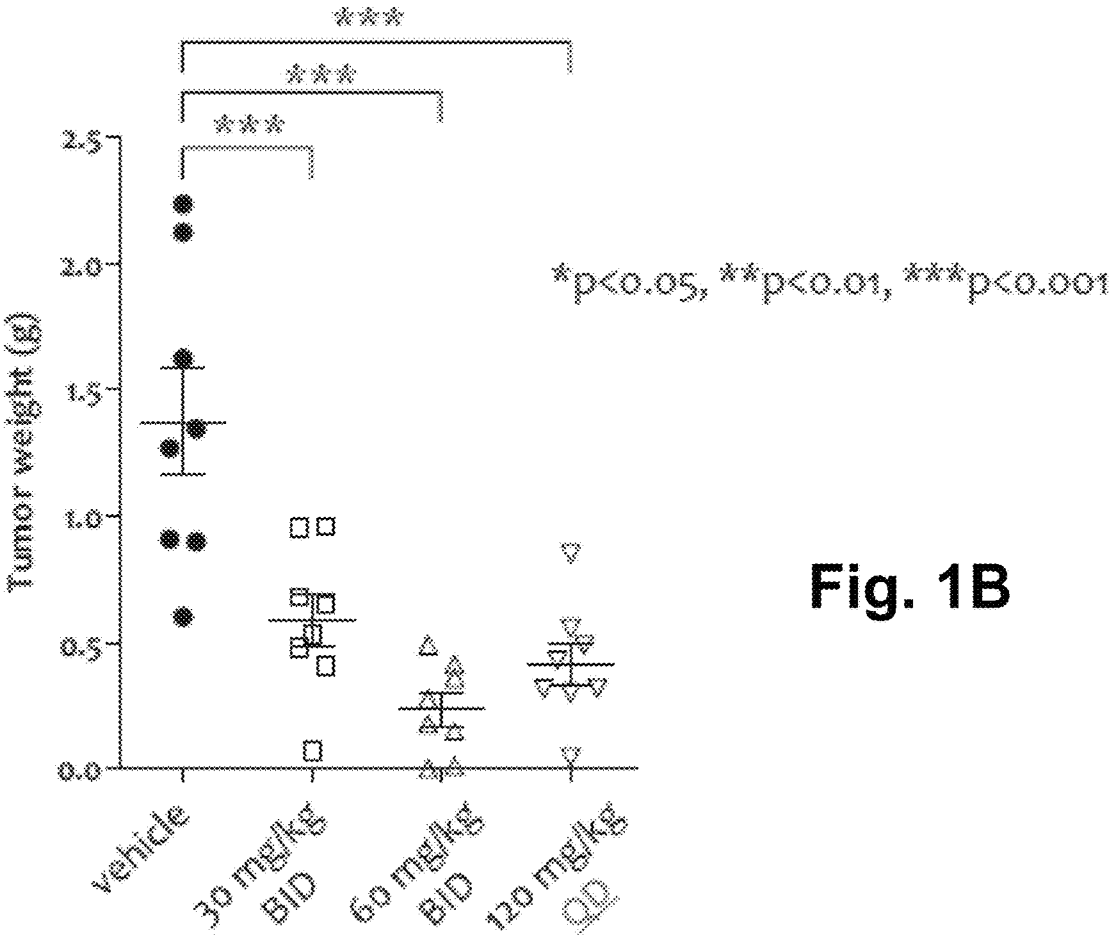
FIG. 1B is a graph showing tumor weights of animals treated with SRA141 monotherapy in a mouse xenograft model of acute myeloid leukemia.

As shown in FIG. 1A, the average tumor volumes of the four groups at day 21 were 1612.66 $mm^3$, 655.68 $mm^3$, 300.77 $mm^3$ and 530.83 $mm^3$, at vehicle and 30 mg/kg BID, 60 mg/kg BID and 120 mg/kg QD mg/kg dose levels, respectively. Tumor weight for individual mice was also calculated (FIG. 1B). Thus, SRA141 administration resulted in tumor growth inhibition of 59%, 81% and 67% at the 30 mg/kg BID, 60 mg/kg BID and 120 mg/kg QD mg/kg dose levels, respectively.

Figure 1C:
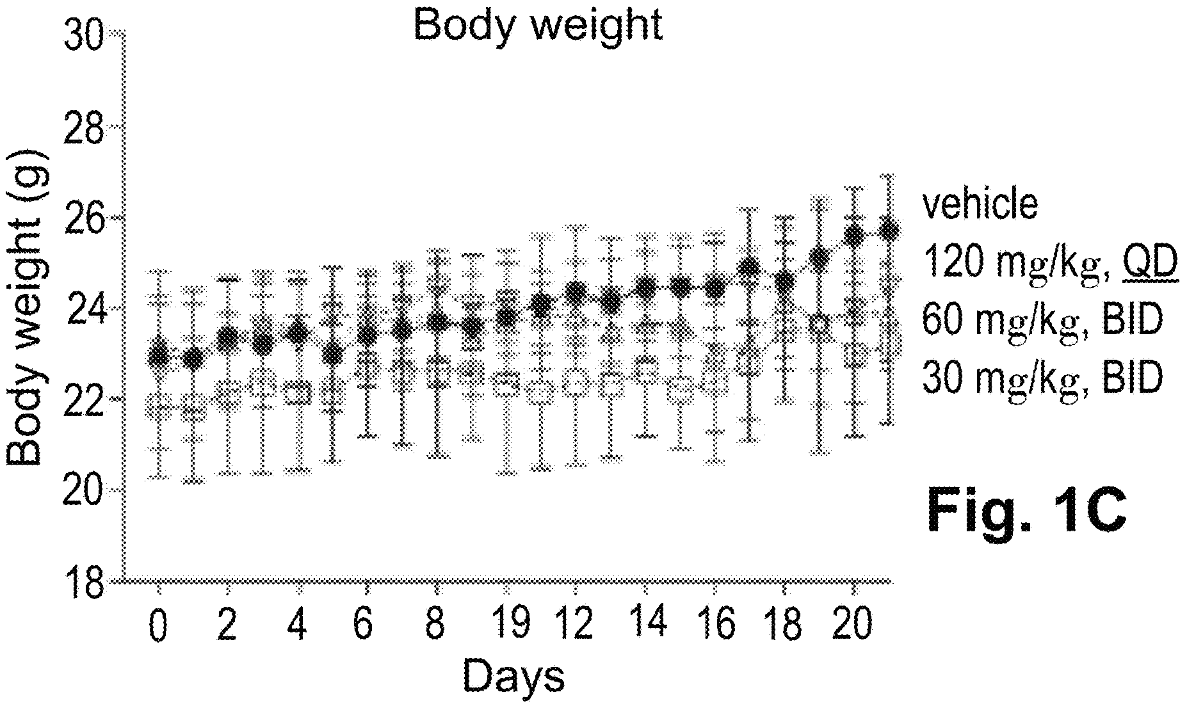
FIG. 1C is a graph showing body weight change of animals treated with SRA141 monotherapy in a mouse xenograft model of acute myeloid leukemia.

All treatments were tolerated with no significant body weight loss (FIG. 1C). The average relative body weight change (RCBW) of the four groups at day 21 were 12.11%, 16.39%, 3.18% and 8.47%, respectively.

These results demonstrate that SRA141 alone as a monotherapy can provide effective therapy for the treatment of acute myeloid leukemia.

Example 2: SRA141 Treatment of Rat AML Xenografts Models

The efficacy of a Cdc7 inhibitor (compound SRA141) as a monotherapy was tested in a rat xenograft model of Acute Myelogenous Leukemia (AML) (FIG. 2). Female rnu/rnu rats were inoculated subcutaneously with $1\times10^7$ MV-4-11 human acute myelogenous leukemia cells. MV-4-11 cells were injected in a totally volume of 0.1 mL PBS in 1:1 Matrigel®. Rats began SRA141 treatment when tumors reached an average size of 300-400 $mm^3$. Rats bearing MV-4-11 tumor xenografts were orally administered (i) vehicle control (0.5% CMC-Na/1% Poloxamer 188) or (ii) SRA141 at 75 mg/kg BID for 5 consecutive days of a 7-day cycle for 4 weeks or (iii) SRA141 at 150 mg/kg QD for 5 consecutive days of a 7-day cycle for 4 weeks (n=10 per treatment group). Tumor volume measurements were taken biweekly and body weight measurements were taken biweekly to day 15, then daily to end of study. Tumor growth inhibition was calculated on Day 42, the final day of the study.

Figures 2A, 2B, 2C:
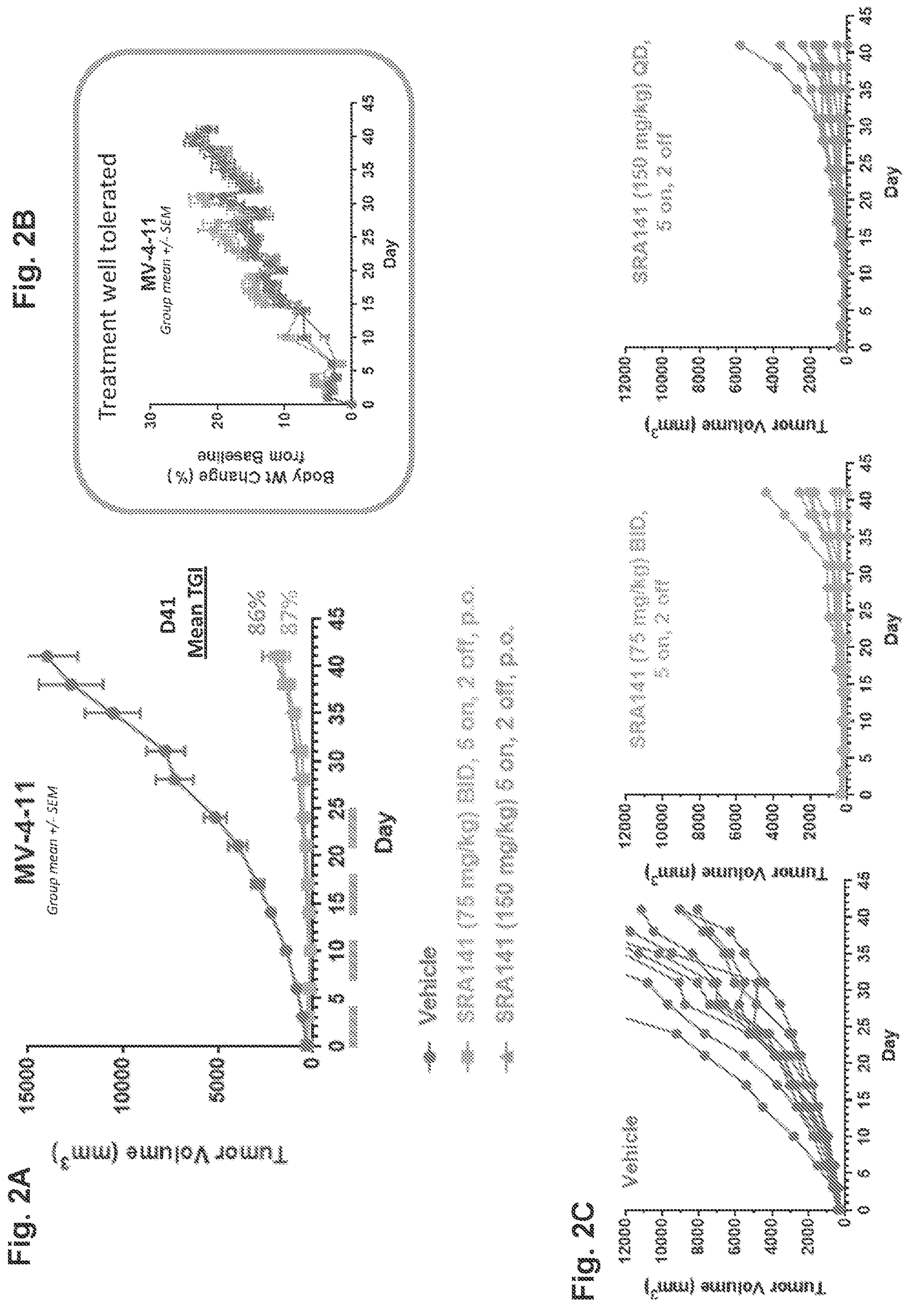
FIG. 2A is a graph showing mean tumor volumes of animals treated with SRA141 monotherapy in a rat xenograft model of acute myeloid leukemia.
FIG. 2B is a graph showing body weight change of animals treated with SRA141 monotherapy in a rat xenograft model of acute myeloid leukemia.
FIG. 2C is a graph showing tumor volumes of individual subjects treated with SRA141 monotherapy in a rat xenograft model of acute myeloid leukemia.

As shown in FIG. 2A, significant tumor growth inhibition (TGI) was observed in rats treated with 75 mg/kg SRA141 (86.1% TGI) and 150 mg/kg SRA141 (86.7% TGI). Additional studies in rats treated with 75 mg/kg SRA141 resulted in observed TGI of 92% at day 27 of treatment and TGI of 85% at day 34 of treatment. Median tumor volume for Vehicle control group was 13247 (n=10), for the SRA141 treated group 75 mg/kg was 1838 (n=8) and for the SRA141 treated group 150 mg/kg group was 1764 (n=9). Results for each treatment per individual rat are shown over the course of treatment (FIG. 2C). Notably, treatment with SRA141 at 75 mg/kg BID produced 1 complete regression (tumor volume <13.5 mm3 for 3 consecutive measurements) and 3 partial regressions (tumor volume <50% of initial volume for 3 consecutive measurements). The complete regression persisted to study termination. Treatment with SRA141 at 150 mg/kg QD produced 2 partial regressions with one animal having no measurable tumor at study completion.

In general, all treatments were well tolerated with no significant body weight loss (FIG. 2B). Three animals were found dead during the course of the study (n=2 in the 75 mg/kg BID and n=1 in the 150 mg/kg BID dosing groups, respectively). The causes of these deaths were classified as non-treatment related.

These results demonstrate that SRA141 as a monotherapy can provide effective therapy for the treatment of AML.

Example 3: SRA141 Treatment of Various Cancer Cells Lines

The concentration-dependent effect of SRA141 on cell viability was determined in a panel of 235 cancer cell lines, utilizing the CellTiter-Glo™ luminescence assay (Promega) with a 72-hour drug incubation period. The 50% inhibition concentration (IC50) was determined in the cancer cell lines using Cell Titer-Glo® luminescent cell viability assay after incubation with SRA141 at different concentrations.

SRA141 demonstrated potent inhibitory activity (IC50<3 μM) in a range of solid tumor cell lines, including those of bladder (5673, RT112/84), sarcoma (143B, CADO-ES1, RD-ES, A673), colon and cecum (Colo-205, DLD-1, LS1034, SK-CO-1, SNU-C1), renal (UO.31), head-and-neck (CNE-2Z, RPMI-2650), melanoma (A2058, A875), and gastric (HGC-27) lineages.

Figure 3A:
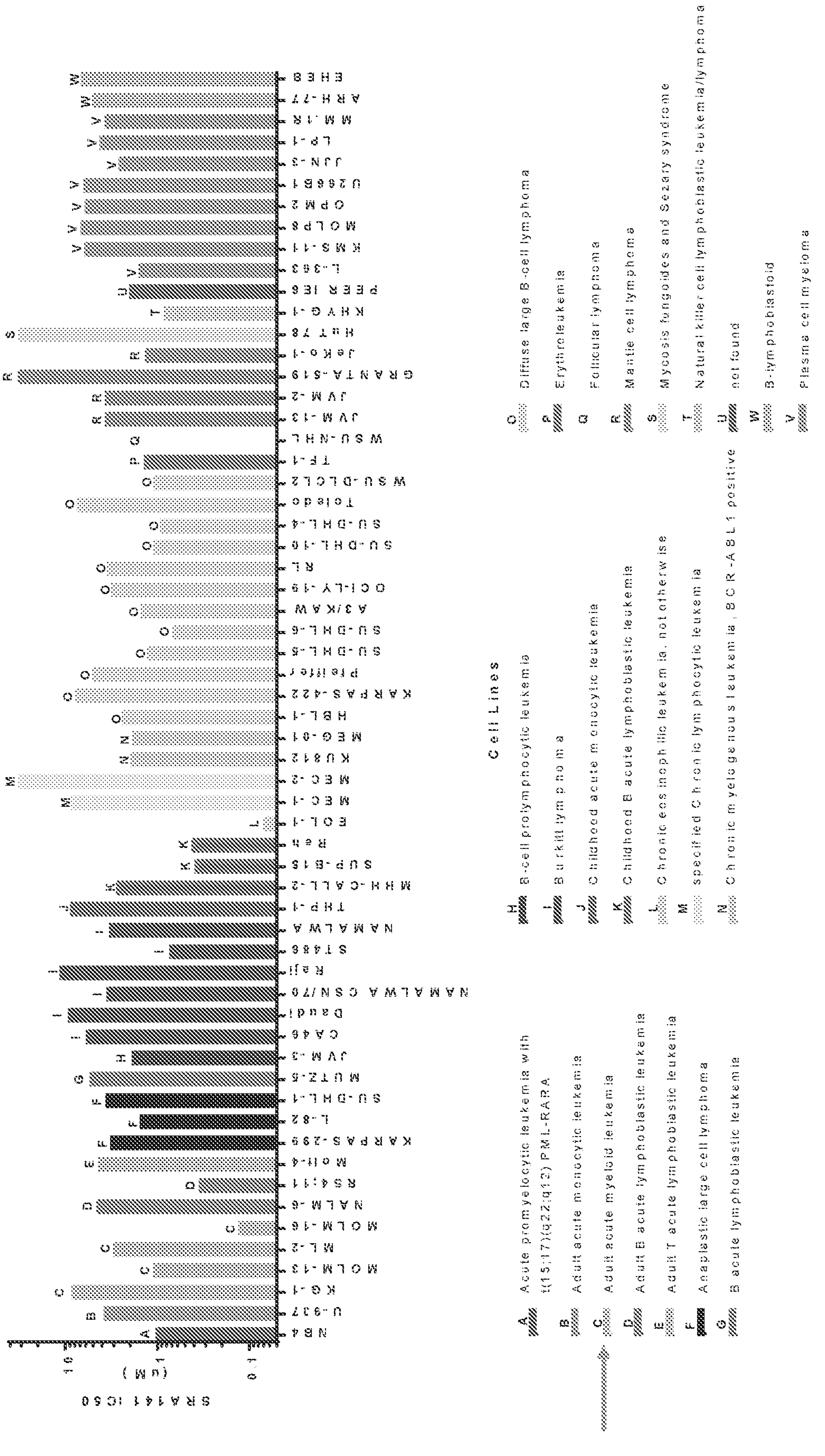
FIG. 3A is a graph showing the half maximal inhibitory concentration ($IC_{50}$) of SRA141 in a panel of hematological cancer derived cell lines.

Significant activity was also observed in hematologic-derived cell lines. The results for 59 hematologic cancer cell lines tested are shown in FIG. 3A. These results demonstrate that SRA141 alone as a monotherapy can provide effective therapy for the treatment of hematologic cancers, such as acute myeloid leukemia (FIG. 3A, cell lines denoted "C") and chronic eosinophilic leukemia (FIG. 3A, cell lines denoted "L"). Significant activity was also observed in i ALL lines (RS411, SUP-B15, Reh) and other leukemias and lymphomas (KHYG-1 and JeKo-1).

Figure 3B:
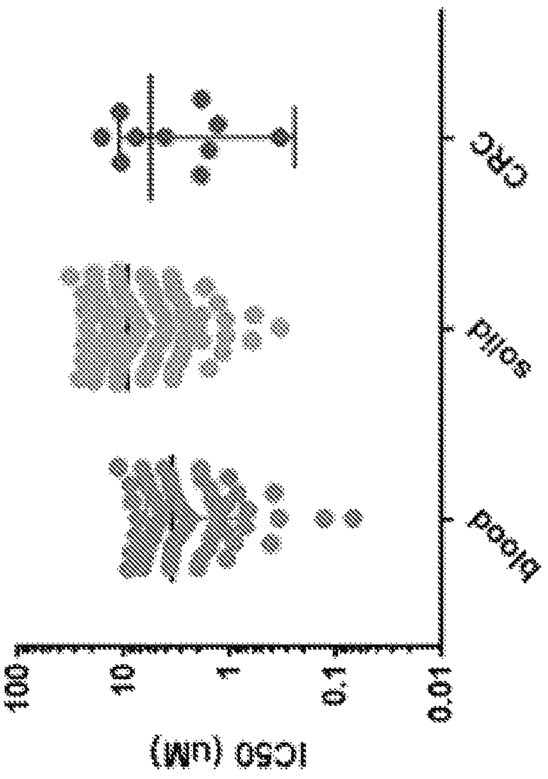
FIG. 3B shows a summary of determined $IC_{50}$ values broken down by cancer type.

A summary of determined IC50 values is summarized in FIG. 3B, and broken down by cancer type. Overall, hematologic cancer lines showed higher sensitivity than solid tumor lines, and within the latter, colorectal cancer lines were among the most sensitive.

Figure 3C:
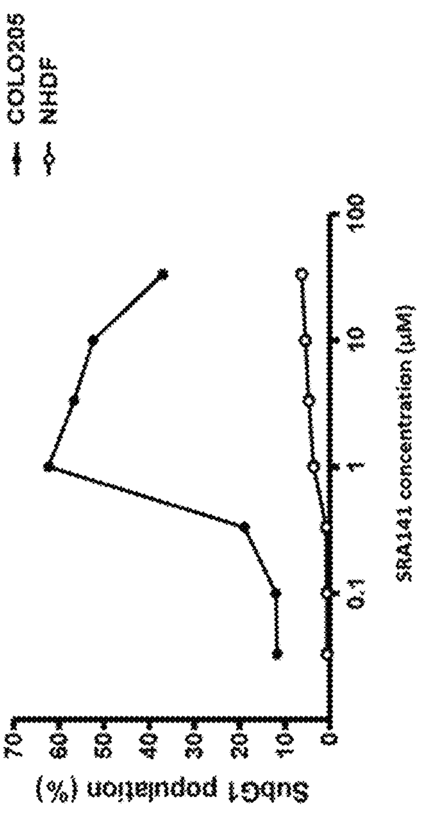
FIG. 3C illustrates sensitivity to SRA141 between cancer and normal cells.

The differential cytotoxic activity of SRA141 in Colo-205 colon cancer cells versus normal human dermal fibroblast cells (NHDF) was assessed at drug concentrations ranging from 0.03 to 33.3 μM (48 h incubation). Following treatment, cells labelled with propidium iodide were analyzed by flow cytometry to determine the percentage of dying cells found in sub-G1 fractions as a consequence of apoptosis-mediated DNA fragmentation. As shown in FIG. 3C, a marked difference in sensitivity to SRA141 between cancer and normal cells was observed. Notably, as many as 62% of cancer cells were dying and found in sub-G1 fraction at compound concentrations between 1 μM and 10 μM. In contrast, fewer than 10% of the normal cells were apoptotic as determined by sub-G1 fraction, consistent with published reports showing minimal cytotoxicity of non-transformed cells following Cdc7 inhibition (Montagnoli, 2004). Thus, these findings support a potential therapeutic index for SRA141 between tumor and non-transformed tissues.

As shown in FIG. 3C, part B, experiments using two different viability assays demonstrated that SRA141 had comparable or superior in vitro activity in numerous cell lines versus other Cdc7 inhibitors, TAK-931 and LY-3177833. Taken together, SRA141 demonstrated potent anti-proliferative activity in numerous cell lines across several indications.

Figure 3D:
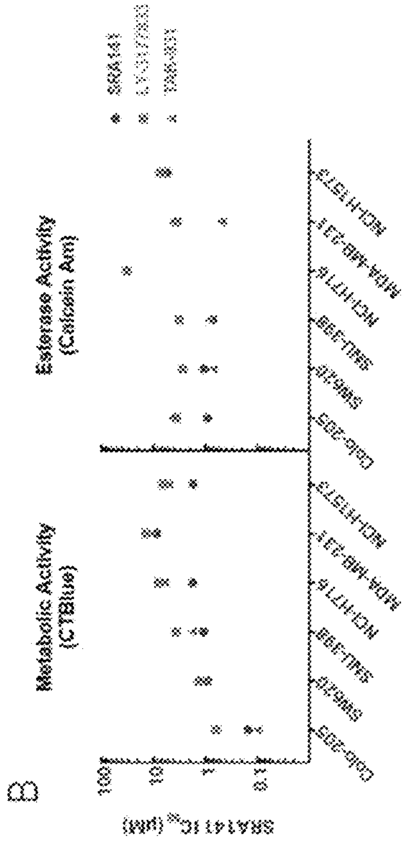
FIG. 3D shows activity of Cdc7 inhibitors SRA141, TAK-931, and LY-3177833 in numerous cell lines.
Figure 3E:
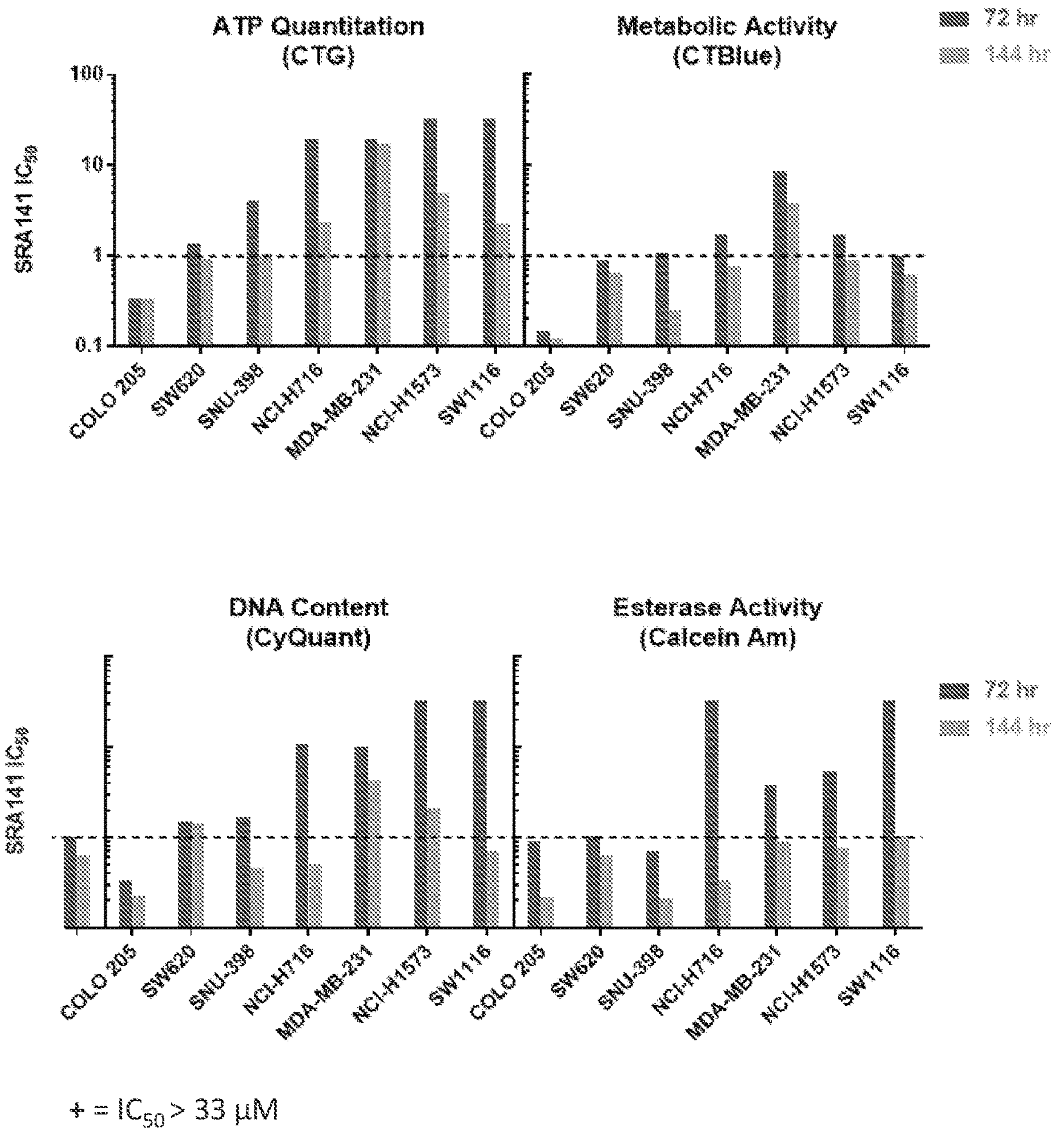
FIG. 3E shows $IC_{50}$ values using four orthogonal assays designed to measure ATP levels (CTG); metabolic activity (CellTiter-Blue (CTB)); DNA content of the cells (CyQuant); and esterase activity (Calcein AM) in seven cell lines after 72 h (left column) and 144 h (right column).
Figure 3F:
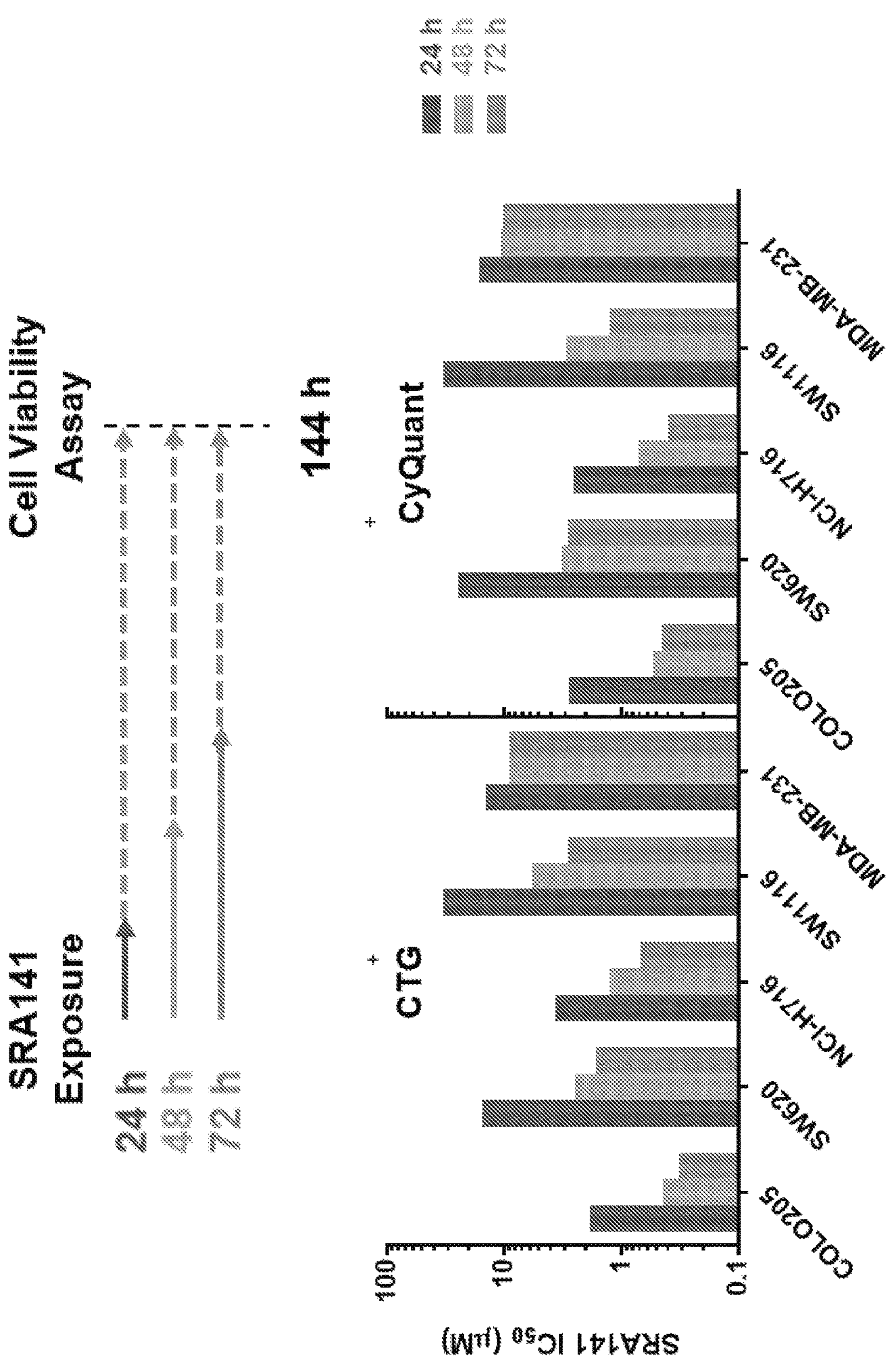
FIG. 3F shows $IC_{50}$ values determined by CTG and CyQuant at 144 h following differing exposure times to SRA141.

The antiproliferative activity of SRA141 was further characterized in seven cell lines (Colo-205, SW620, SNU-398, NCI-H716, MDA-MB-231, NCI-H1573 and SW1116) using four orthogonal assays designed to measure ATP levels (CTG); metabolic activity (CellTiter-Blue (CTB)); DNA content of the cells (CyQuant); and esterase activity (Calcein AM). The relative sensitivities of cell lines within each assay format were generally concordant. As shown in FIG. 3D, a consistent increase of SRA141 potency was observed with a longer treatment duration of 144 h (right column) when compared with 72 h (left column) across all assays and cell lines tested, suggesting that the continuous target coverage would be required for optimal antitumor activity. Monotherapy SRA141 IC50s were also determined by CTG and CyQuant at 144 h following differing exposure times to SRA141. As shown in FIG. 3E, consistent with the earlier assessment, SRA141 potency increased with treatment duration beyond 24 h (24 h left column, 48 h middle column, or 72 h right column).

Example 4: SRA141 Treatment of Patient Derived Xenograft Mouse Models of CRC

The efficacy of a Cdc7 inhibitor (compound SRA141) as a monotherapy was tested in a patient derived xenograft (PDX) model of colorectal cancer (CRC). Female nu/nu mice bearing CTG-1009 patient-derived APC- and TP53-mutant colorectal tumor xenografts were administered (i) vehicle control (0.1 M HCl/0.5% MC) or (ii) SRA141 at 120 mg/kg QD for 28 days or (iii) SRA141 at 150 mg/kg QD for 2 consecutive days of a 7-day cycle for 28 days (n=8 per SRA141 treatment group; n=6 vehicle control group; Champions study 1250-003). Tumor growth inhibition was calculated on Day 32, the final day of the study. Dosing was suspended temporarily to a number of animals in the SRA141 120 mg/kg QD and 150 mg/kg QD groups due to weight loss (FIG. 4B). These dosing holidays ranged from 1-3 days (n=1 and 3 animals), 4-8 days (n=7 and 0 animals) in the SRA141 120 mg/kg QD and 150 mg/kg QD treatment groups, respectively.

Figure 4A:
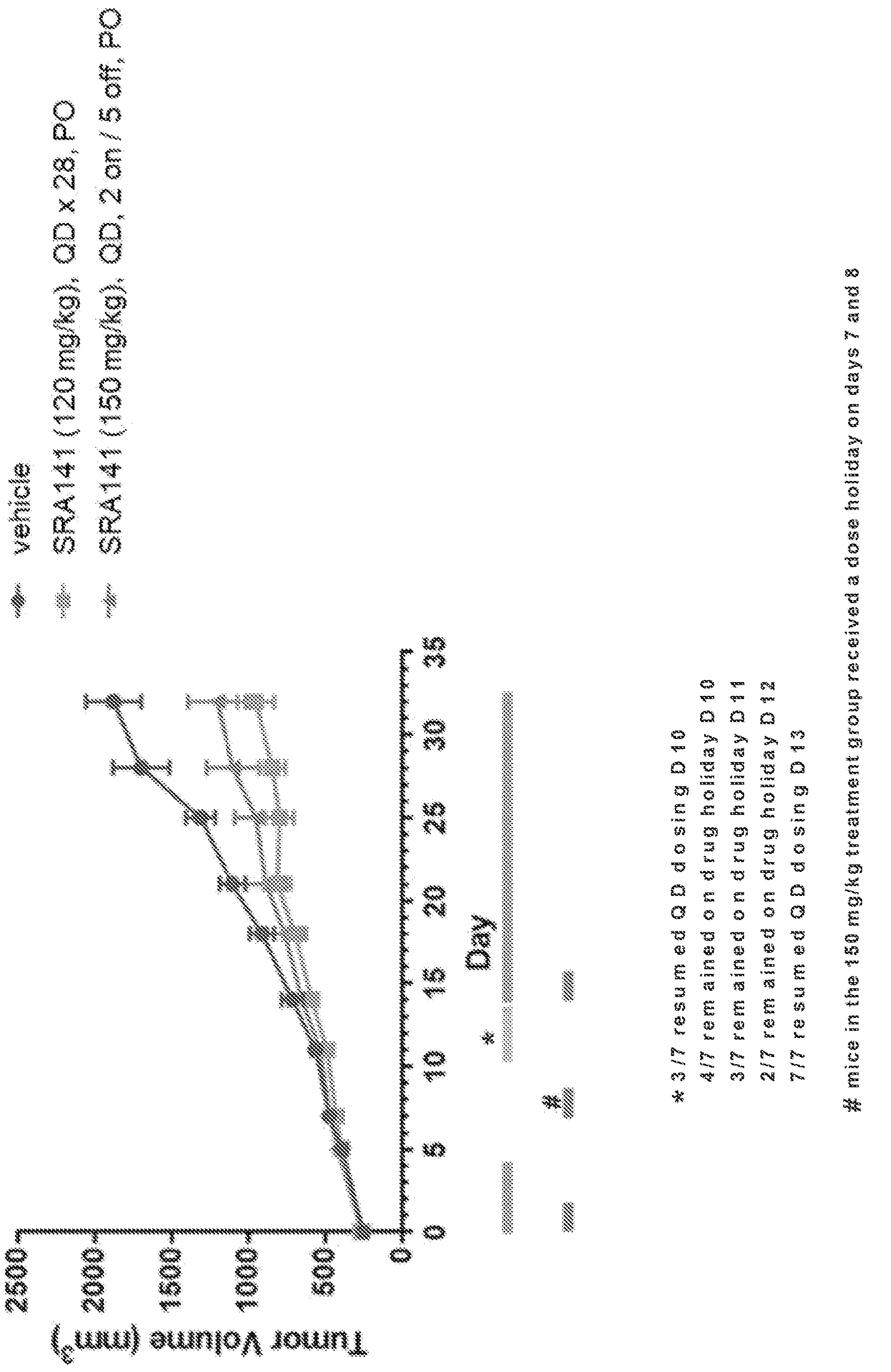
FIG. 4A is a graph showing mean tumor volumes of animals treated with SRA141 monotherapy in a patient derived xenograft (PDX) model of colorectal cancer (CRC).
Figure 4B:
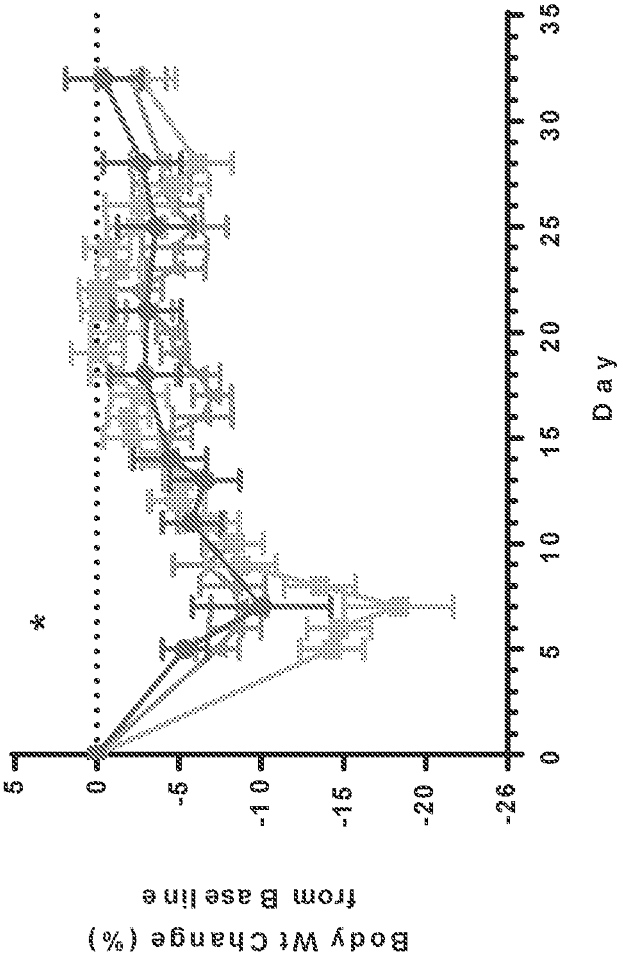
FIG. 4B is a graph showing body weight change of animals treated with SRA141 monotherapy in a patient derived xenograft (PDX) model of colorectal cancer (CRC).

As shown in FIG. 4A, SRA141 administration resulted in tumor growth inhibition of 49% and 36% at the 120 mg/kg QD and 150 mg/kg QD dose levels, respectively.

Figure 5:
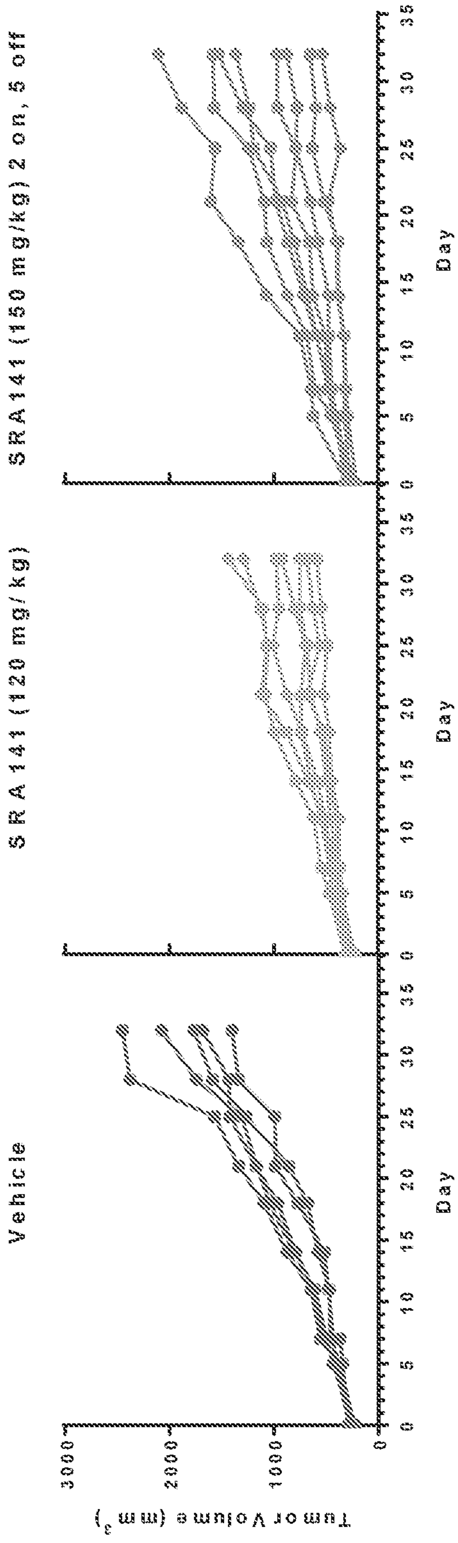
FIG. 5 is a graph showing tumor volumes of individual subjects of animals treated with SRA141 monotherapy in a patient derived xenograft (PDX) model of colorectal cancer (CRC).
Figure 6:
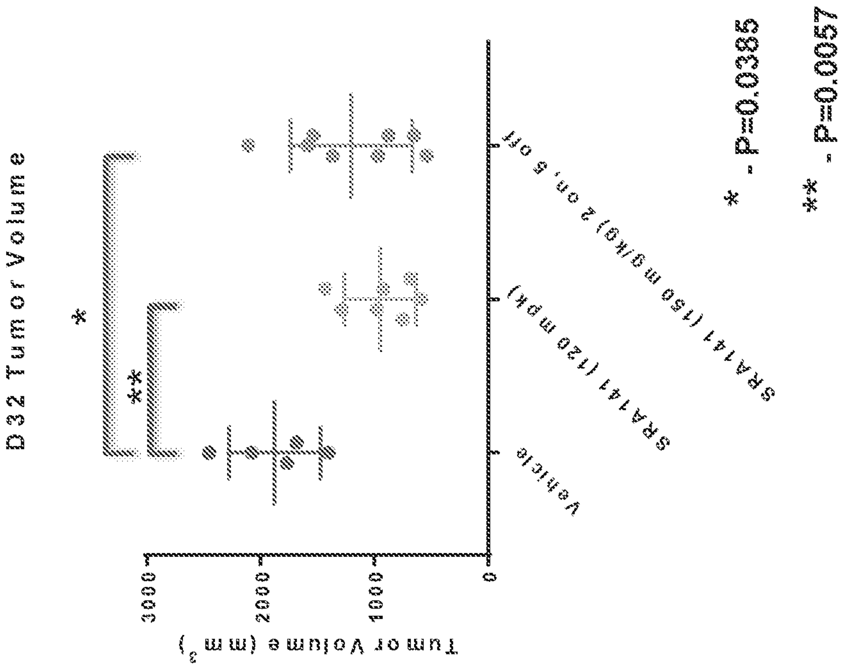
FIG. 6 is a graph showing mean tumor volumes of animals treated with SRA141 monotherapy on Day 32 (D32) of treatment in a patient derived xenograft (PDX) model of colorectal cancer (CRC).

The mean tumor growth inhibition (TGI) observed following SRA141 (120 mg/kg, dosed QD 5D on with a dose holiday ranging from 5-7D and subsequent QD dosing) was 49.4% (P=0.0057). SRA141 dosed 4 or 6 times during the time of the experiment resulted in a mean TGI of 35.8% on D32 (P=0.0385). The mean TGI observed following SRA141 (120 mg/kg, dosed QD 5D on with a dose holiday ranging from 5-7D and subsequent QD dosing) was 49.4% (P=0.0057). The individual TGI from mean vehicle tumor volume (TV) were: 23.5, 31.3, 47.8, 50.8, 59.9, 63.6 and 68.6%. SRA141 dosed 4 or 6 times during the time of the experiment resulted in a mean TGI of 35.8% on D32 (P=0.0385). The 3 mice with 4 doses had TGI from mean vehicle TV of 12.4, 27.2 and 53.2%. The 5 mice that received 6 doses had TGI form mean vehicle TV of 15.6, 18.2, 48.2, 65.2, and 71.2%. Results for each treatment per individual mouse are shown over the course of treatment (FIG. 5) and at Day 32 (FIG. 6). Therefore, monotherapy with SRA141 resulted in significant tumor growth inhibition (TGI) as determined on D32 of the study.

In general, all treatments were well tolerated by the end of treatment with no significant body weight loss relative to vehicle (closed circles). Modest weight loss was observed following initial 5 days dosing in the 120 mg/kg group (closed squares) but recovered following several day drug holiday to vehicle levels (FIG. 4B).

These results demonstrate that SRA141 as a monotherapy can provide effective therapy for the treatment of colorectal cancer in APC and TP53 mutated CRC settings.

Example 5: SRA141 Treatment of Patient Derived Xenograft Rat Models of CRC

The efficacy of a Cdc7 inhibitor (compound SRA141) as a monotherapy was tested in a rat xenograft model of colorectal cancer (CRC) (FIG. 7). Female Rowett nude rats were inoculated sub-cutaneously with $2\times10^7$ COLO-205 human colorectal carcinoma cells. All rats were gamma-irradiated (4Gy) 24 hours before tumor cell injection. The COLO-205 cells were injected in 0.2 mL PBS in 1:1 Matrigel®. Female The nude rats bearing Colo-205 tumor xenografts were orally administered (i) vehicle control (0.5% CMC-Na/1% Lutrol F-68) or (ii) SRA141 150 mg/kg once a day (QD) for 5 consecutive days of a 7-day cycle for 6 weeks or (iii) SRA141 75 mg/kg twice a day (BID) for 5 consecutive days of a 7-day cycle for 6 weeks (n=7 per treatment group). Tumor growth inhibition was calculated on Day 31, the final day all vehicle control animals remained on study. Tumor volume measurements and body weight measurements were taken biweekly.

Figure 7A:
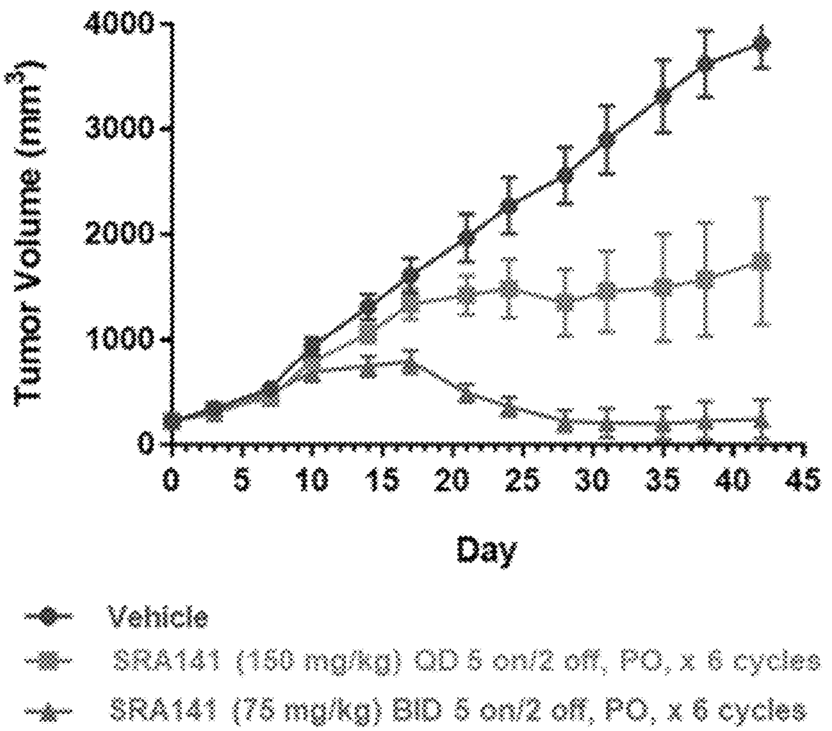
FIG. 7A is a graph showing mean tumor volumes of animals treated with SRA141 in a rat xenograft model of colorectal cancer.

As shown in FIG. 7A, administration of SRA141 resulted in significant tumor growth inhibition of 50% and 93% at the 150 mg/kg QD and 75 mg/kg BID dose levels, respectively. Complete tumor regressions were observed in 4/7 rats. Furthermore, complete tumor regressions (defined as no measurable tumor for 3 consecutive measurements) were observed in 4 of 7 animals and a partial regression (tumor volume <50% of initial volume for 3 consecutive measurements) in 1 of 7 animals at the 75 mg/kg BID dose. All 4 complete regressions persisted to study completion.

Figure 7B:
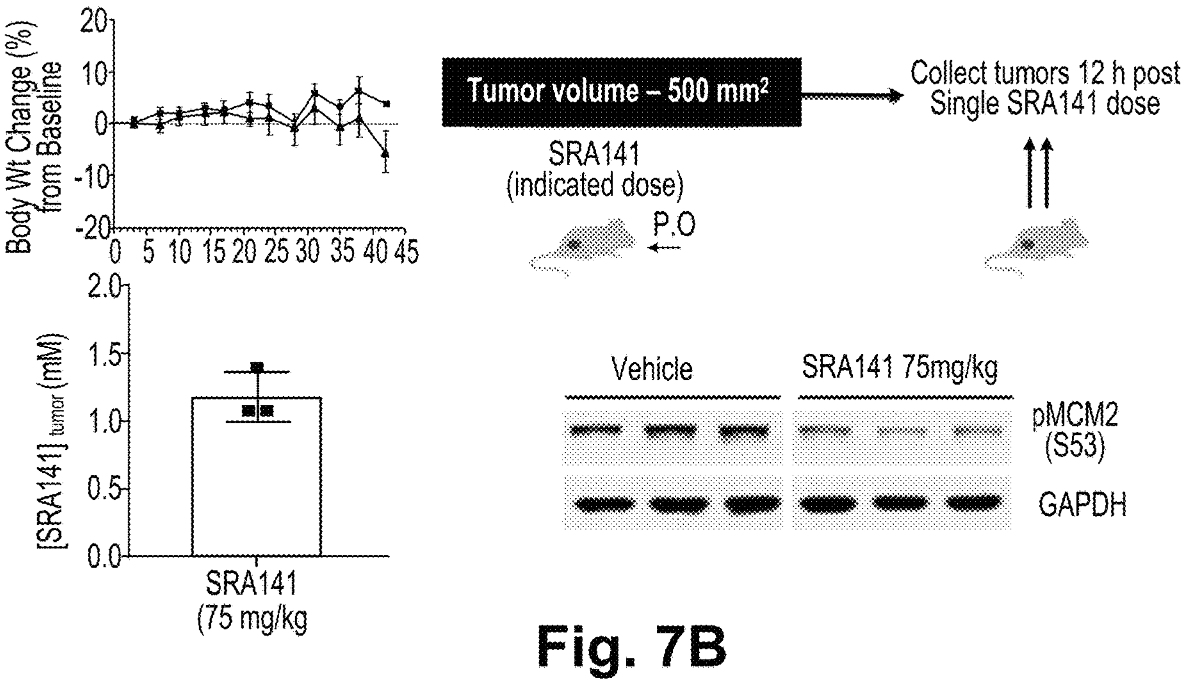
FIG. 7B shows graphs of percent body weight change, tumor concentration of SRA141, and an immunoblot showing reduction of phosphorylated MCM2 12 hours post-treatment with SRA141 in a rat xenograft model of colorectal cancer.

As shown in FIG. 7B, tumor SRA141 concentration of approximately 1.2 μM resulted in an approximate 50% decrease in phosphorylated MCM2 (Serine 53) as compared to rats treated with vehicle, suggesting that selective inhibition of Cdc7 is incompatible with tumor cell survival. Colo-205 tumor-bearing rats were treated with a single dose of SRA141 or vehicle and the tumors were collected 12 hours later. Tumor homogenates prepared from three animals per treatment group were analyzed by LC/MSMS or Western blot. The results demonstrate that SRA141 as a monotherapy can provide effective therapy for the treatment of colorectal cancer.

Example 6: SRA141 Combination with Additional Anti-Neoplastic Agents

To confirm the efficacy of a Cdc7 inhibitor in combination with anti-neoplastic agents to sensitize cancer cells, experiments were performed in human cancer cells.

Methods for Combination Assessment:

The combination screen was performed using the co-treatment dosing schedule for SRA141 and the partner compound. Both enhancee (SRA141) and enhancer (partner compound) were added at time zero (0 h). Cells were exposed to SRA141 and the enhancer for the entire 72-hour treatment time. All data points were collected via automated processes and were subject to quality control and analyzed using proprietary software. Assay plates were accepted if they pass the following quality control standards: relative raw values were consistent throughout the entire experiment, Z-factor scores were greater than 0.6 and untreated/vehicle controls behaved consistently on the plate.

The Growth Inhibition (GI) was utilized as a measure of cell growth. GI percentages are calculated by applying the following test and equation:

$$\text{If } T < V_0 : 100 * \left(1 - \frac{T - V_0}{V_0}\right)$$

$$\text{If } T\text{â\%¥}V_p : 100 * \left(1 - \frac{T - V_0}{V - V_0}\right)$$

where T is the signal measure for a test article at 72 or 96 hours, V is the untreated/vehicle-treated control measure, and $V_0$ is the untreated/vehicle control measure at time zero (also colloquially referred to as $T_0$ plates). This formula is derived from the Growth Inhibition calculation used in the National Cancer Institute's NCI-60 high throughput screen. A GI reading of 0% represents no growth inhibition and would occur in instances where the T reading at 72 or 96 hours are comparable to the V reading at the respective time period. A GI 100% represents complete growth inhibition (cytostasis) and in this case cells treated with compound for 72 or 96 hours would have the same endpoint reading as T0 control cells. A GI of 200% represents complete death (cytotoxicity) of all cells in the culture well and in this case the T reading at 72 or 96 hours will be lower than the $T_0$ control (values near or at zero). These GI calculations were used in all single agent and combination data analysis for the combination screen.

Inhibition as a measure of cell viability: Inhibition levels of 0% represent no inhibition of cell growth by treatment. Inhibition of 100% represents no doubling of cell numbers during the treatment window. Both cytostatic and cytotoxic treatments can yield an Inhibition Percentage of 100%. Inhibition Percentage is calculated as the following: I=1−T/U, where T is treated and U is untreated.

Synergy Score Analysis

To measure combination effects in excess of Loewe additivity, a scalar measure was used to characterize the strength of synergistic interaction termed the Synergy Score. The Synergy Score is calculated as:

$$\text{Synergy Score}=\log f_X \log f_Y \Sigma \max(0, I_{data})(I_{data}-I_{Loewe})$$

The fractional inhibition for each component agent and combination point in the matrix is calculated relative to the median of all vehicle-treated control wells. The Synergy Score equation integrates the experimentally-observed activity volume at each point in the matrix in excess of a model surface numerically derived from the activity of the component agents using the Loewe model for additivity. Additional terms in the Synergy Score equation (above) are used to normalize for various dilution factors used for individual agents and to allow for comparison of synergy scores across an entire experiment. The inclusion of positive inhibition gating or an Idata multiplier removes noise near the zero effect level, and biases results for synergistic interactions at that occur at high activity levels. Combinations with higher maximum Growth Inhibition (GI) effects or those which are synergistic at low concentrations will have higher Synergy Scores. Those combinations with Synergy Scores that statistically supersede baseline self-cross values can be considered synergistic. The magnitude of GI effects may be linked to the growth rate of cells which varies for each cell line examined.

Potency shifting was evaluated using an isobologram, which demonstrates how much less drug is required in combination to achieve a desired effect level, when compared to the single agent doses needed to reach that effect. The isobologram was drawn by identifying the locus of concentrations that correspond to crossing the indicated inhibition level. This is done by finding the crossing point for each single agent concentration in a dose matrix across the concentrations of the other single agent. Practically, each vertical concentration $C_Y$ is held fixed while a bisection algorithm is used to identify the horizontal concentration $C_X$ in combination with that vertical dose that gives the chosen effect level in the response surface $Z(C_X,C_Y)$. These concentrations are then connected by linear interpolation to generate the isobologram display. For synergistic interactions, the isobologram contour fall below the additivity threshold and approaches the origin, and an antagonistic interaction would lie above the additivity threshold. The error bars represent the uncertainty arising from the individual data points used to generate the isobologram. The uncertainty for each crossing point is estimated from the response errors using bisection to find the concentrations where $Z-\sigma_Z(C_X,C_Y)$ and $Z+\sigma_Z(C_X,C_Y)$ cross $I_{cut}$, where $\sigma_Z$ is the standard deviation of the residual error on the effect scale.

Synergy Score Analysis: Loewe Volume Score Analysis

Figure 8:
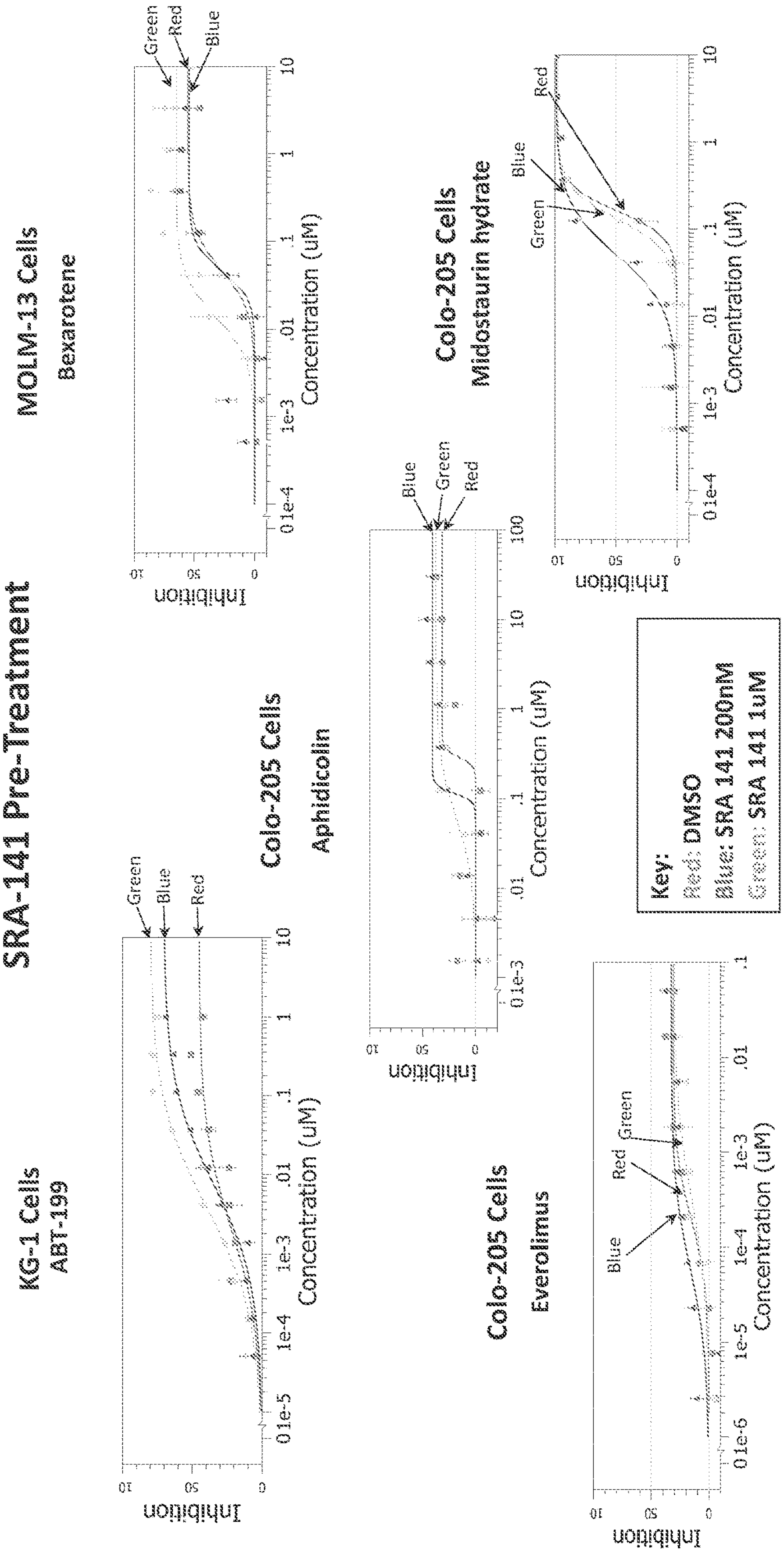
FIG. 8 are graphs showing inhibition of cell growth (cell viability compared to 0 hr and 72 hr untreated control) of cells lines sequentially treated (pre-treated) with SRA141 in combination with anti-neoplastic agents.

Loewe Volume Score is used to assess the overall magnitude of the combination interaction in excess of the Loewe additivity model. Loewe Volume is particularly useful when distinguishing synergistic increases in a phenotypic activity (positive Loewe Volume) versus synergistic antagonisms (negative Loewe Volume). When antagonisms are observed, as in the current dataset, the Loewe Volume is assessed to examine if there is any correlation between antagonism and a particular drug target-activity or cellular genotype. This model defines additivity as a non-synergistic combination interaction where the combination dose matrix surface is indistinguishable from either drug crossed with itself. The calculation for additivity is: $I_{Loewe}$ that satisfies $(X/X_I)+(Y/Y_I)=1$ where $X_I$ and $Y_I$ are the single agent effective concentrations for the observed combination effect I. For example, if 50% inhibition is achieved separately by 1 μM of drug A or 1 μM of drug B, a combination of 0.5p M of A and 0.5 μM of B should also inhibit by 50%. Activity observed in excess of Loewe additivity identifies synergistic interaction. For the present analysis, empirically derived combination matrices were compared to their respective Loewe additivity models constructed from experimentally collected single agent dose response curves. Summation of this excess additivity across the dose response matrix is referred to as Loewe Volume. Positive Loewe Volume suggests synergy, while negative Loewe Volume suggests antagonism. As mentioned above, Synergy Score is a positively gated value and cannot be used to gauge potential antagonism To confirm the efficacy of a Cdc7 inhibitor in combination with anti-neoplastic agents to kill cancer cells, experiments were performed in Colo-205 colorectal adenocarcinoma cells and acute myeloid leukemia cells, either with sequential treatment or simultaneous treatment with the Cdc7 inhibitor, SRA141, in combination with an anti-neoplastic agent. To confirm the efficacy of a Cdc7 inhibitor to sensitize cancer cells when used in combination with an inhibitor of the mammalian target of rapamycin (mTOR) pathway, an inhibitor of DNA polymerase, an inhibitor of receptor tyrosine kinases (RTK), an inhibitor of the mitogen activated protein kinase pathway (MAPK) or an inhibitor of phosphatidylinositol-4,5-bisphosphate 3 kinase (PI3K) pathway, human Colo-205 colorectal adenocarcinoma cells were sequentially treated with SRA141, followed by treatment with everolimus, aphidicolin or midostaurin as a single agent (FIG. 8). Flasks of Colo-205 cells were pre-treated with SRA141 (1 μM and 200 nM) and DMSO control for 48 hrs; cells were washed and seeded into 384-well plates, and plates were left to incubate for 6 hrs, followed by treatment with everolimus, aphidicolin or midostaurin six hours after plating as single agents. After 72 hrs, ATP levels were measured using ATPlite. Pre-treatment of COLO-205 cells with SRA141 demonstrated an enhancer potency shift towards increase in sensitivity for midostaurin, and a 3.19 $EC_{50}$ fold change was observed with 200 nM SRA141 pre-treatment compared to DMSO pre-treatment. For aphidicolin, a 4.60 $EC_{50}$ fold change was observed with 1 μM SRA141 pre-treatment compared to DMSO pre-treatment. For everolimus, a 3.3 $EC_{50}$ fold change was observed for 200 nM SRA141 pre-treatment compared to DMSO pre-treatment.

Figure 9:
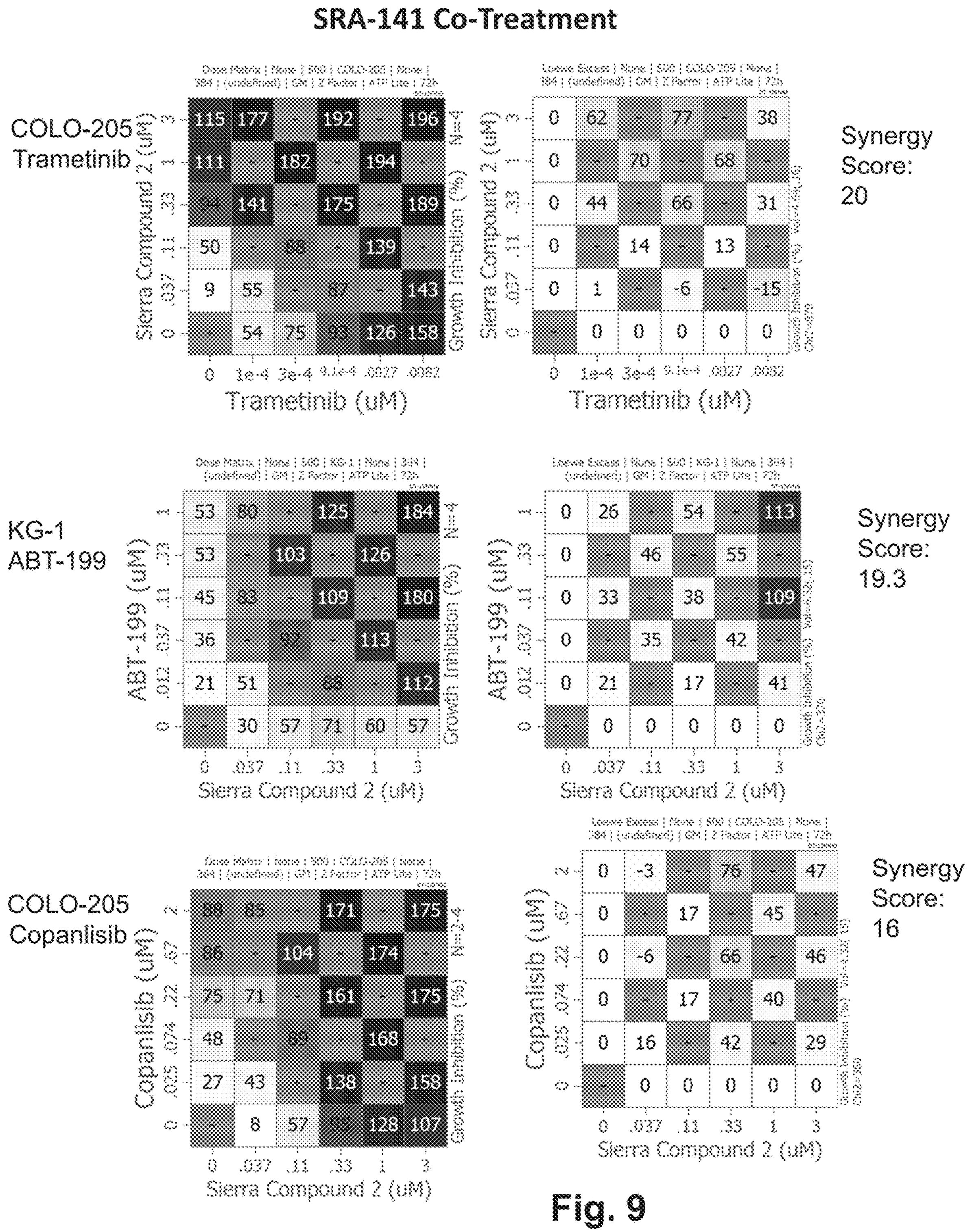
FIG. 9 shows tables depicting synergy scores for growth inhibition of cell lines co-treated with SRA141 ("Sierra compound 1") in combination with anti-neoplastic agents.
Figure 9:
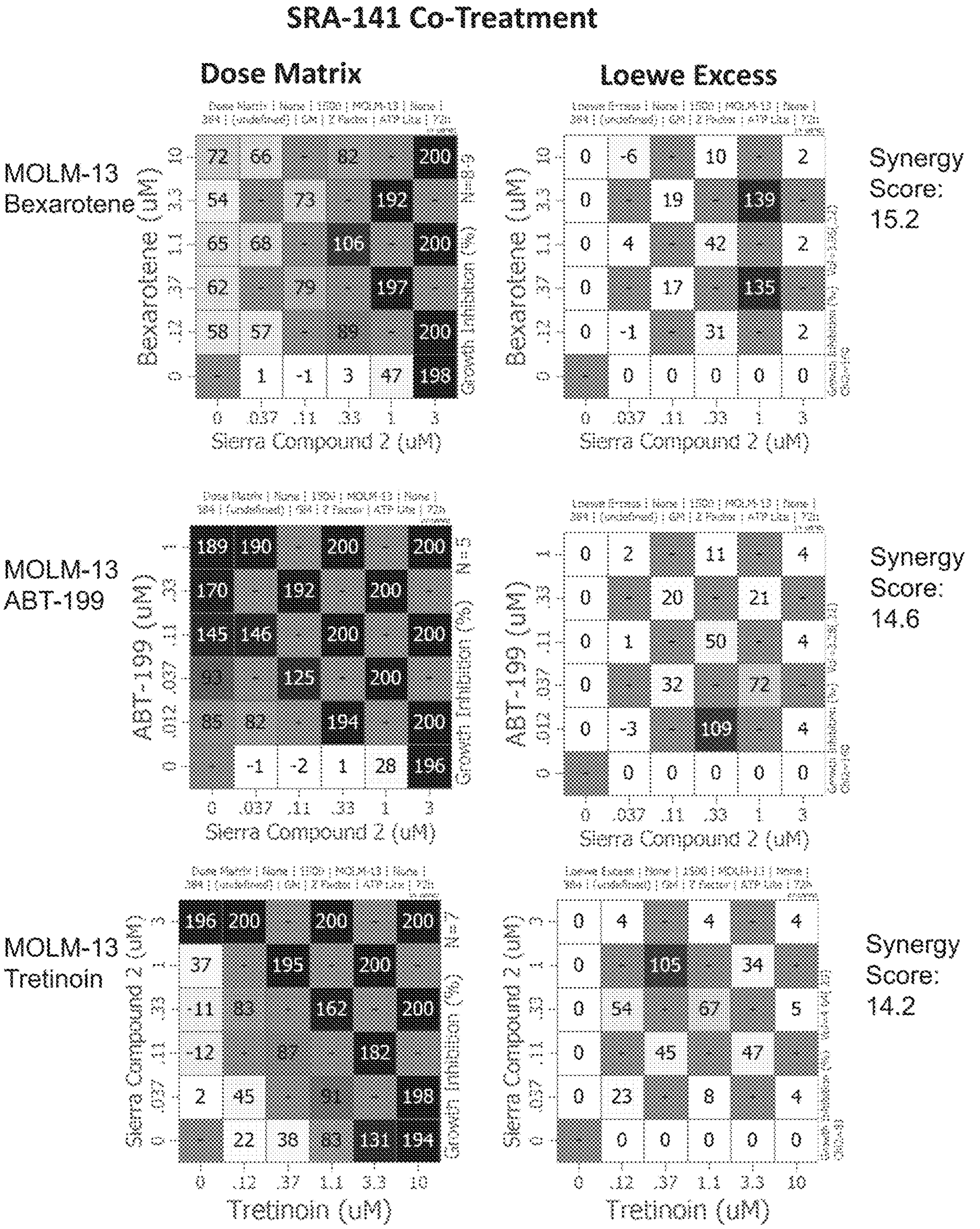
Figure 10A:
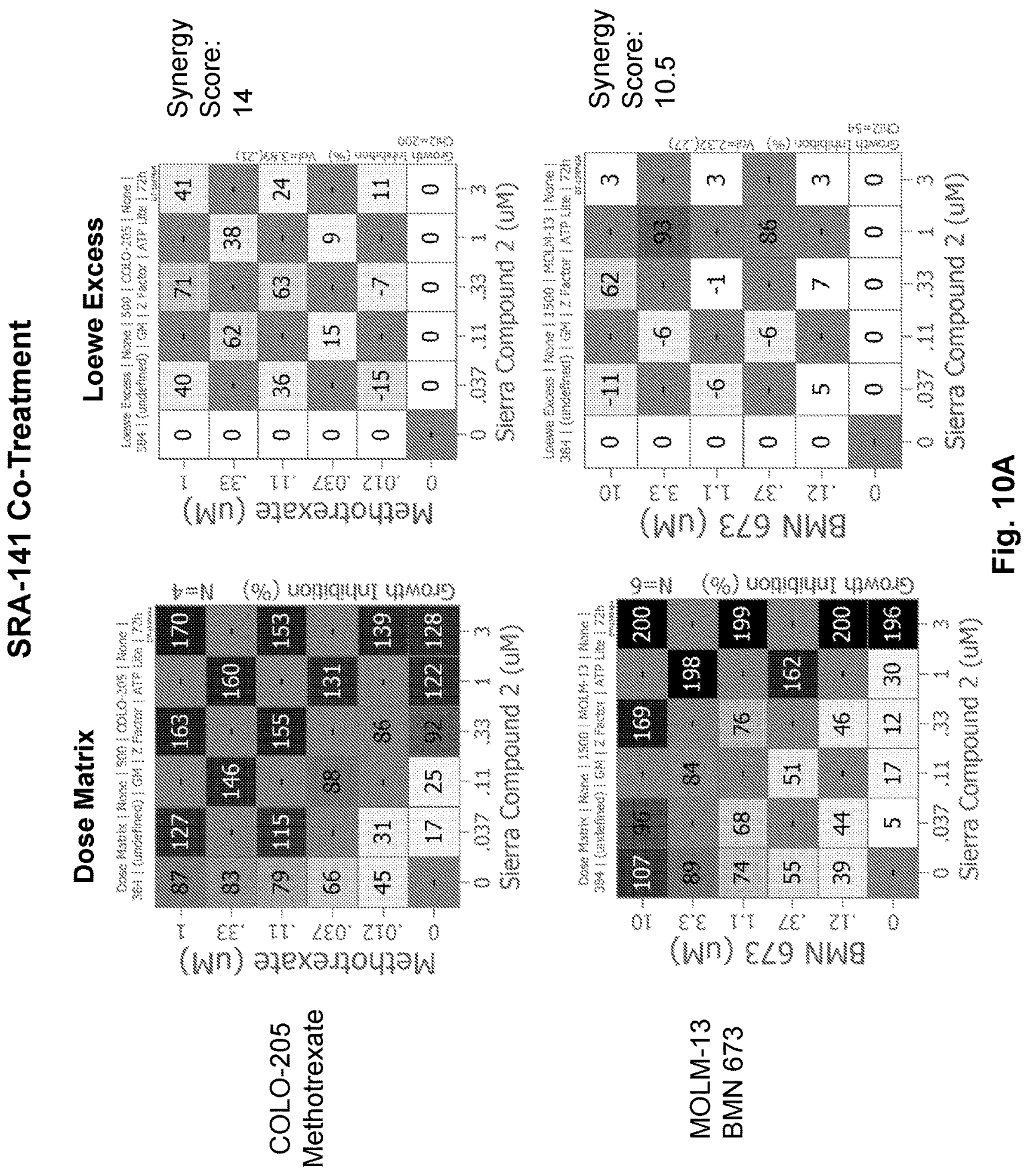
FIG. 10A shows tables depicting synergy scores for growth inhibition of cell lines co-treated with SRA141 ("Sierra compound 1") in combination with anti-neoplastic agents.

To confirm the efficacy of a Cdc7 inhibitor in combination with MAPK pathway inhibitor or a PI3K pathway inhibitor, for killing cancer cells and for use in the treatment of cancer, Colo-205 cells were simultaneously treated with the MAPK pathway inhibitor, trametinib, a PI3K pathway inhibitor, copanlisib, and an anti-metabolite, (anti-folte), methotrexate (FIGS. 9 and 10A). Cells were seeded into 384-well plates on day 0; plates were left to incubate for 24 hrs; cells were dosed with trametinib and copanlisib in combination with SRA141, and after 72 hours, ATP levels were measured using ATPlite. Strong synergies were observed in the COLO-205 cells with simultaneous combination treatment with inhibitors of the MAPK pathway and PI3K pathway and the antifolate antimetabolite, methotrexate.

To confirm the efficacy of a Cdc7 inhibitor to sensitize cancer cells when used in combination with an inhibitor of the mitogen activated protein kinase pathway (MAPK), a regulator of the retinoid pathway, an apoptosis regulator, a PARP inhibitor, or an inhibitor of the mammalian target of rapamycin (mTOR) pathway, human acute myeloid leukemia cells, MOLM-13 cells, were sequentially treated with SRA141, followed by treatment with trametinib or bexarotene as a single agent (FIG. 8). Flasks of MOLM-13 cells were pre-treated with SRA141 (1 μM and 200 nM) and DMSO control for 48 hrs; cells were washed and seeded into 384-well plates; plates left to incubate for 6 hrs, followed by treatment with trametinib or bexarotene six hours after plating as single agents. After 72 hrs, ATP levels were measured using ATPlite. For trametinib, a 2.63 $EC_{50}$ fold change was observed for 200 nM SRA141 pre-treatment compared to DMSO pre-treatment. For bexarotene, a 2.63 $EC_{50}$ fold change was observed for 200 nM SRA141 pre-treatment compared to DMSO pre-treatment. For everolimus, a 3.25 $EC_{50}$ fold change was observed with 200 nM SRA141 pre-treatment compared to DMSO pre-treatment.

To confirm the efficacy of a Cdc7 inhibitor in combination with a regulator of the retinoid pathway, an apoptosis regulator, or a PARP inhibitor for killing cancer cells and for use as a combination therapy for the treatment of cancer, human MOLM-13 and KG-1 cells were simultaneously treated with the PARP inhibitor, BMN673, the apoptosis regulator ABT-199, the retinoid pathway regulator, bexarotene, or the retinoid pathway regulator, tretinoin (FIGS. 9 and 10A). Cells were seeded into 384-well plates on day 0; plates left to incubate for 24 hrs; cells were dosed with BMN673, ABT-199, bexarotene or tretinoin in combination with SRA141, and after 72 hours, ATP levels were measured using ATPlite. MOLM-13 cells demonstrated strong synergies for BMN673 (PARP inhibitor), ABT-199 (BCL-2 inhibitor), bexarotene and tretinoin (regulators of the Retinoid pathway). These results confirm that combination therapies comprising use of a Cdc7 inhibitor in combination with an inhibitor of the mTOR pathway, an inhibitor of DNA polymerase, and inhibitor of receptor tyrosine kinases, and inhibitor of the MAPK pathway, a regulator of the retinoid pathway, a regulator of apoptosis, or a PARP inhibitor, are effective for killing cancer cells, either with sequential or concurrent administration with a Cdc7 inhibitor and demonstrates that administration of a Cdc7 inhibitor in combination with an inhibitor of the mTOR pathway, an inhibitor of DNA polymerase, and inhibitor of receptor tyrosine kinases, and inhibitor of the MAPK pathway, a regulator of the retinoid pathway, a regulator of apoptosis, or a PARP inhibitor, are regulator of the retinoid pathway, a regulator of apoptosis, or a PARP inhibitor, are effective cancer treatment regimens.

Figure 10B:
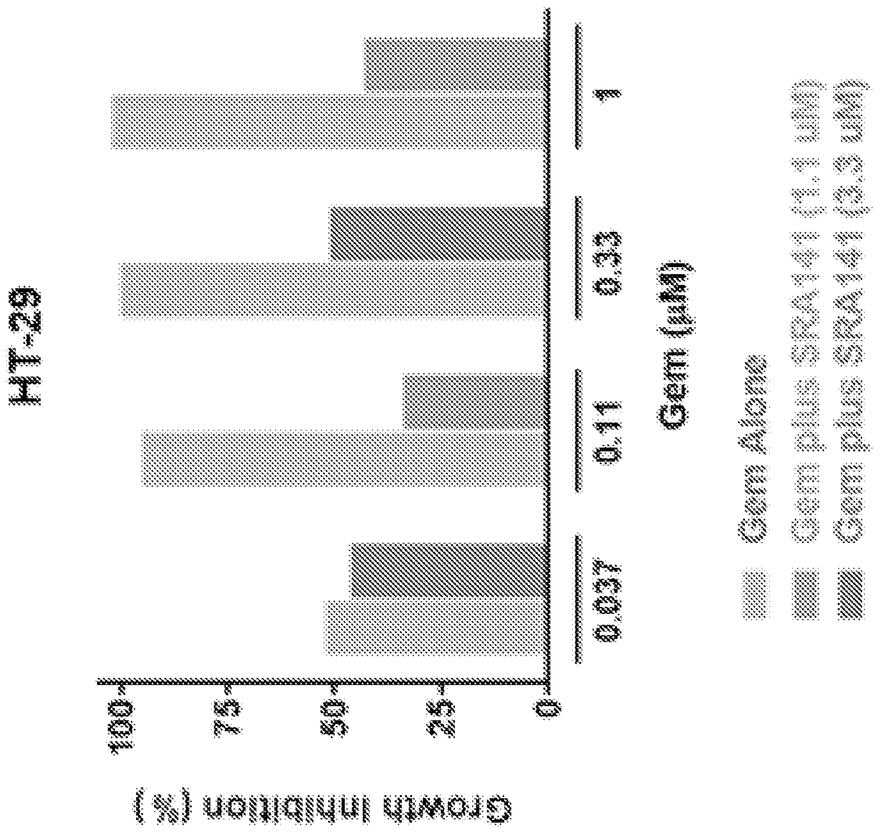
FIG. 10B is a graph showing percent growth inhibition of HT-29 cells treated with gemcitabine alone or in combination with SRA141.

To confirm the efficacy of a Cdc7 inhibitor in combination with the replicative stress-inducing anti-neoplastic agent gemcitabine, human HT-29 colorectal adenocarcinoma cells were treated with increasing concentrations of gemcitabine (from 0.037 to 1 μM) for 96 hours. Data shown in FIG. 10B demonstrate that gemcitabine doses greater than 100 nm resulted in near 100% growth inhibition of the treated cells. Further, addition of SRA141 at a concentration of either 1.1 μM or 3.3 μM substantially reduced the inhibitory effects of gemcitabine.

Example 7: Potency and Selectivity of SRA141 in Biochemical Assays

Inhibition of Cdc7 by SRA141 was measured using in vitro kinase assays.

Figure 11:
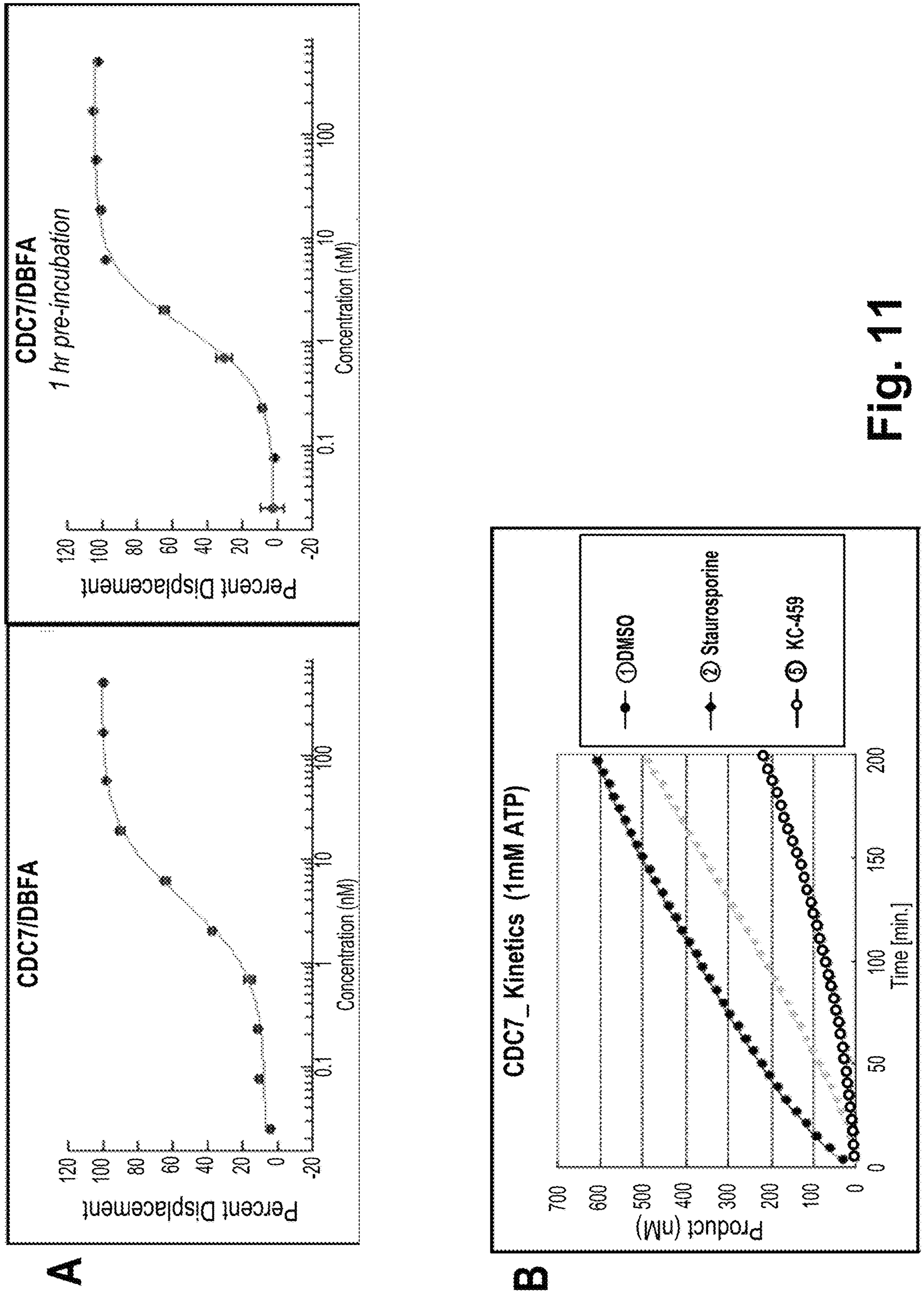
FIG. 11A shows potent inhibition of Cdc7 by SRA141 in an in vitro biochemical assay.
FIG. 11B shows residence time for SRA141 binding to Cdc7 and dissociation kinetics.

As shown in FIG. 11A, SRA141 demonstrated potent inhibition of Cdc7 in an in vitro biochemical assay (IC50=4 nM). Pre-incubation of SRA141 with Cdc7 enzyme for 1 hour prior to assay conduct modestly improved the compound potency (IC50=1.4 nM), confirming potent inhibition of Cdc7 with potentially advantageous inhibitor binding kinetics. These findings are consistent with rapid dilution studies that indicate a long residence time for SRA141 binding to Cdc7 (t1/2=215 mins) and slow dissociation kinetics (Koff=0.0032 at 5 nM), as shown in FIG. 11B.

Figure 12:
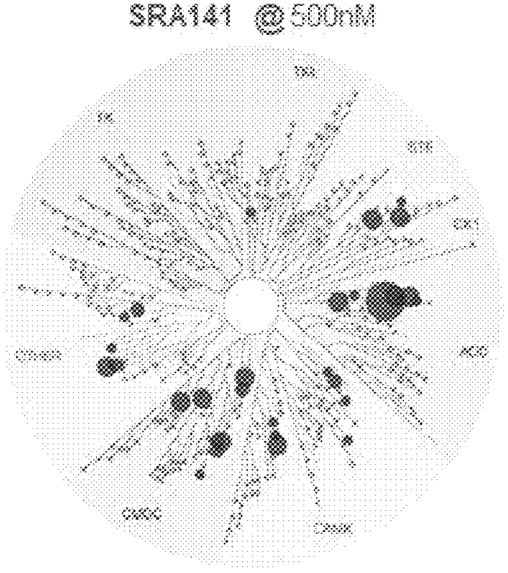
FIG. 12 shows results of kinome screening assays of SRA141 and TAK931.
Figure 12:
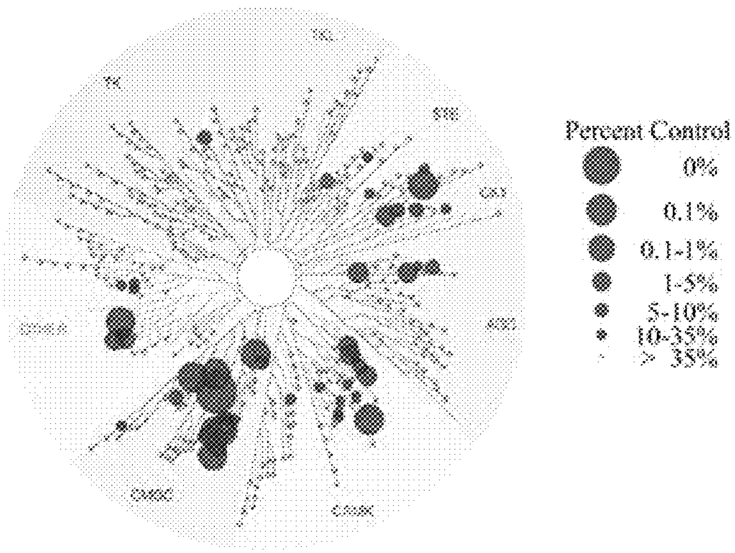

The selectivity of SRA141 for Cdc7 was assessed using the DiscoverX kinome screening assay, containing approximately 430 native and mutant kinases. Minimal off-target kinase activity was detected at a compound concentration of 500 nM. Selectivity of SRA141 for Cdc7 was compared to TAK-931. Results of the kinome screening assay (FIG. 12), demonstrate that SRA141 has less off-target activity compared to TAK-931 at a compound concentration of 500 nM.

Example 8: Effect of SRA141 on Cellular Substrates of Several Cell Cycle Kinases Colo-205 cells were treated with SRA141 (at concentrations between 0.033 and 3.3 μM) for 8 to 24 hours with subsequent assessment of the phosphorylation status of the downstream targets for Cdc7 (MCM2, Ser40/41 and Ser53), and the putative off-target kinases CDK8 (STAT1, Ser727); CDK7 and 9 (RNA pol II, Ser2); LATS2 (YAP1, Ser127) as well as the levels of MCL-1, known to be indirectly controlled by CDK9 (Gregory, 2015).

MV411 cells were also treated with SRA141 in a dose-dependent manner (at concentrations between 0.5 and 3.3 μM) and were subsequently assessed for phosphorylation status of MCM2 at Ser40/41 and Ser53.

Figure 13:
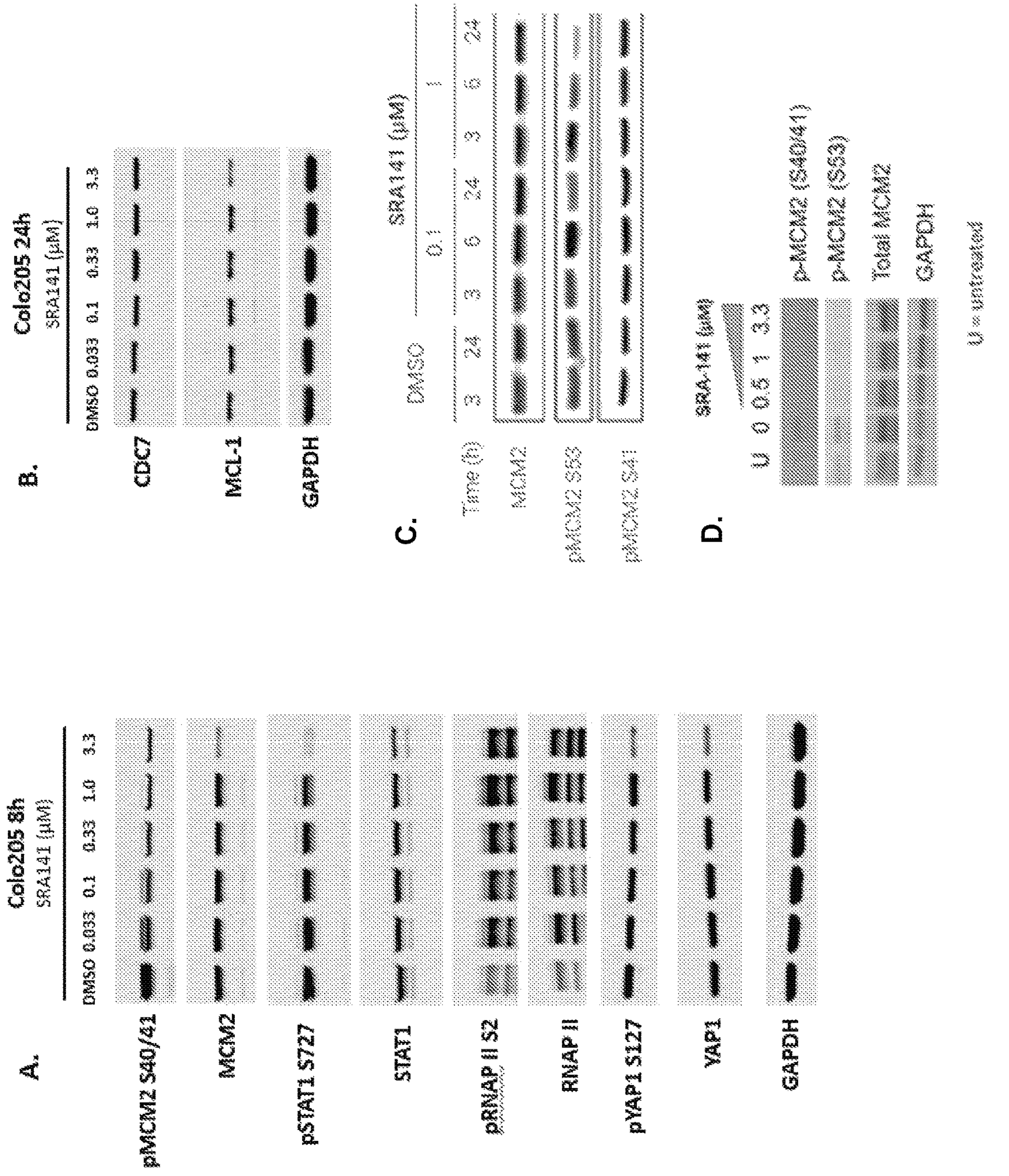
FIG. 13 shows Colo-205 cells treated with SRA141 for 8 (FIG. 13A) to 24 (FIG. 13B) hours at concentrations between 0.033 and 3.3 μM, and for 3, 6, and 24 hours (FIG. 13C) at concentrations of 0.1 and 1 μM, and MV411 cells treated with SRA141 at concentrations between 0.5 and 3.3 μM (FIG. 13D) with subsequent assessment of the phosphorylation status of the downstream targets for Cdc7.

As shown in FIG. 13, Cdc7 levels were unchanged in these studies, while the phosphorylation of its target MCM2 at Ser40/41 and Ser53 was reduced in a concentration-dependent manner starting at 0.033 μM (Colo-205) and 0.5 μM (MV411), demonstrating robust on-target inhibition in cells.

There was no significant change in the phosphorylation status (or protein level of MCL-1) for any of the cellular substrates at concentrations of SRA141 up to 1 μM. Minimal inhibition of STAT1, YAP1 and MCL-1 was observed at 3.3 μM, although the co-incident reduction of total protein levels suggests that these findings may have been due to SRA141 mediated cell death.

Together, these data confirm the potency and selectivity of SRA141 in cellular settings.

Example 9: Activity of SRA141 in AML Three-Dimensional (3D) Cultures

The activity of SRA141 was investigated in in vitro and ex vivo three-dimensional (3D) cultures prepared from three AML cell lines (EOL-1, Molm-16 and MV-4-11) and three AML PDX models (AM5512, AM7440 and AM7577), respectively. Tumor cultures were treated with SRA141 (0.08 to 33 μM) for 5 days. SRA141 demonstrated potent anti-cellular activity (IC50 range 0.15 to 1.6 μM) in five of the six models, with reduced activity noted in the AM5512 preparation (IC50=3.2 μM; Table 2). This latter model was also relatively resistant to cytarabine and cisplatin (IC50 >8.9 μM).

TABLE 2

SRA141 Activity in AML 3D Cultures

| Model Type | Model | SRA141 IC50 (μM) | Cytarabine IC50 (μM) | Cisplatin IC50 (μM) |
|---|---|---|---|---|
| Cell line | EOL-1 | 0.27 (>97%) | 0.002 (>98%) | 0.64 (>98%) |
| Cell line | Molm-16 | 0.24 (>97%) | 0.07 (>98%) | 0.38 (>98%) |
| Cell line | MV-4-11 | 1.44 (>97%) | 0.05 (>98%) | 0.62 (>98%) |
| AML PDX | AM7440 | 1.61 (>97%) | 0.27 (>91%) | 1.34 (>98%) |
| AML PDX | AM7577 | 0.15 (>97%) | ND (>98%) | 4.18 (>98%) |
| AML PDX | AM5512 | 3.16 (>97%) | 8.89 (>72%) | 11.91 (>98%) |

Note:
Maximum inhibition is noted as a percentage next to IC50

Note: Maximum inhibition is noted as a percentage next to IC50

The anti-proliferative activity of SRA141 (0.3-5 μM) was also evaluated in additional 3D growth studies conducted in a methylcellulose growth matrix using normal human myeloid (n=3) and AML-blast progenitors incubated for 14 days.

The mean SRA141 IC50 value for the normal bone marrow preparations was 0.25 μM, while the mean IC50 value for the AML samples was approximately 0.16 μM (with the resistant progenitor sample AML810 censored; Table 3). The positive control, cytosine arabinoside (Ara C), had equipotent IC50 values (approximately 0.004 μM) for both the normal bone marrow and AML-blast progenitor samples. The Therapeutic Index was also calculated for each sample [(Primary AML $IC_{50}$)÷(BMNC control $IC_{50}$)]. As shown in Table 3, 5 out of 9 primary AML samples demonstrated response to SRA141 with a TI (AML200, AML917, AML915, AML190, and AML717), while only 2 out of 9 samples responded with a TI to Ara-C (AML200 and AML250).

Collectively, these data demonstrate that SRA141 possesses potent cytotoxic activity in AML 3D cultures, with a potential therapeutic index over normal bone marrow progenitors.

TABLE 3

SRA141 Activity in Normal Bone Marrow and AML-Blast Progenitors Grown in 3D Cultures

| Model Type | Model | SRA141 $IC_{50}$ (nM) | Ara C $IC_{50}$ (nM) |
|---|---|---|---|
| Normal bone marrow | 525 | 375 | 3.7 |
| Normal bone marrow | 111 | 165 | 4.8 |
| Normal bone marrow | 525 | 212 | 3.8 |
| Mean normal bone marrow IC50 (nM) | | 251 ± 110 | 4.1 ± 0.6 |
| AML-blast progenitor | 917 | 202 | 5.7 |
| AML-blast progenitor | 915 | 177 | 8.1 |
| AML-blast progenitor | 717 | 118 | 3.8 |
| AML-blast progenitor | 810 ** | 831 | 9.6 |
| AML-blast progenitor | 180 | 337 | 3.6 |
| AML-blast progenitor | 190 | 73 | 6.1 |
| AML-blast progenitor | 200 | 119 | 2.8 |
| AML-blast progenitor | 250 | 159 | 2.2 |
| AML-blast progenitor | 260 | 140 | 3.0 |
| Mean AML-blast progenitor IC50 (with AML 810; nM) | | 240 ± 234 | 5.0 ± 2.6 |
| Mean AML-blast progenitor IC50 (without AML 810; nM) | | 166 ± 80 | 4.4 ± 2.0 |

TABLE 3-continued

** Sample Censored

** Sample Censored

Example 10: Durability of Cdc7 Inhibition by SRA141 in Cultured Cells

The durability of drug-induced Cdc7 inhibition was investigated in Colo-205 cells treated with two concentrations of SRA141 (0.1 μM and 1 μM) for 48 hours, followed by either immediate cell harvest, or removal of the drug incubate followed by an additional 24 hours incubation prior to cell harvest. Phosphorylation of MCM2 at Ser53, a target site of Cdc7 activity, was compared between the two conditions.

Figure 14:
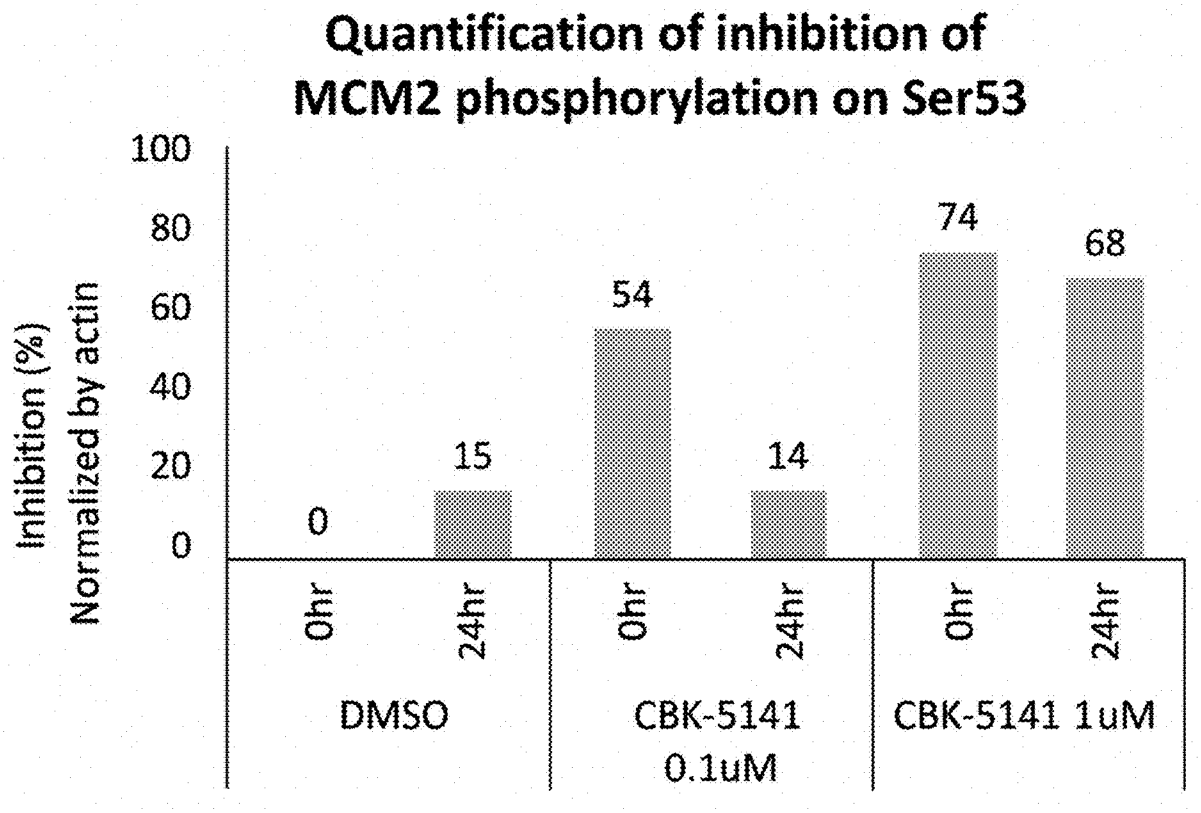
FIG. 14 is a graph showing quantification of phosphorylation on Ser53 of MCM2 following treatment with SRA141 at 0.1 μM and 1 μM for 24 hours.

As shown in FIG. 14, data from this study indicated recovery of Cdc7 activity by 24 hours following compound washout at the 0.1 μM drug concentration while prolonged pMCM2 inhibition was observed at 24 hours following washout of the higher incubation concentration (1 μM). These results are consistent with the precedent biochemical assays which indicated a slow target off-rate and consequent prolonged enzyme inhibition.

Example 11: SRA141 Cell Cycle Sensitivity Analysis

The sensitivity to SRA141 treatment at the various phases of the cell cycle was determined in Colo-205 cells synchronized with double thymidine block. Upon block release, SRA141 (1 μM) was added as the cells reached either S or M phase.

Figure 15B:
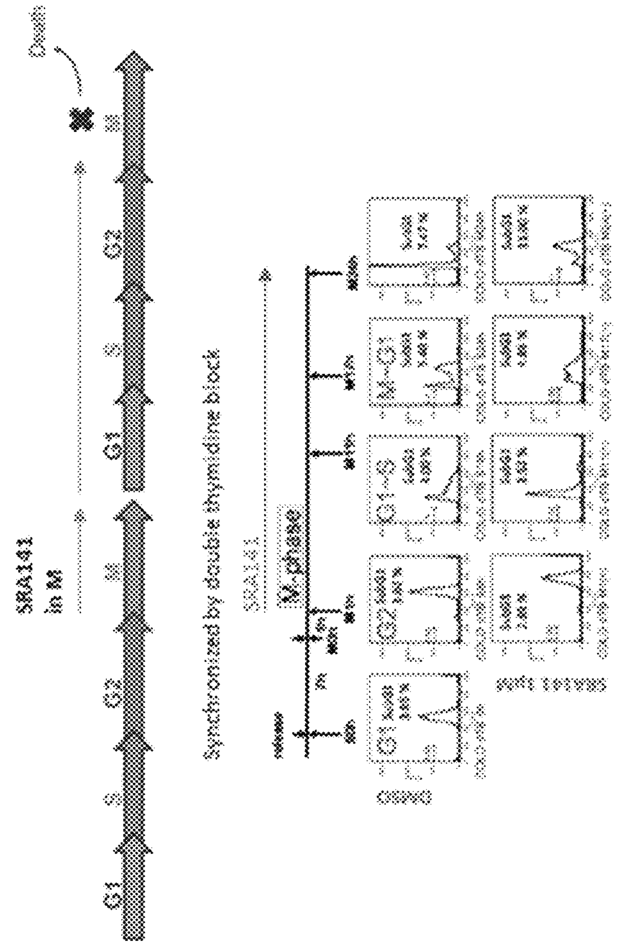
FIG. 15 shows flow cytometry data from cells treated with SRA141 during S phase (FIG. 15A) and at the beginning of M phase (FIG. 15B); assessment of cell cycle and DNA markers in cells treated with SRA141 (FIG. 15C); and assessment of the percent of mitotic cells in a population of cells treated a Cdc7 inhibitor (FIG. 15D).
Figure 15A:
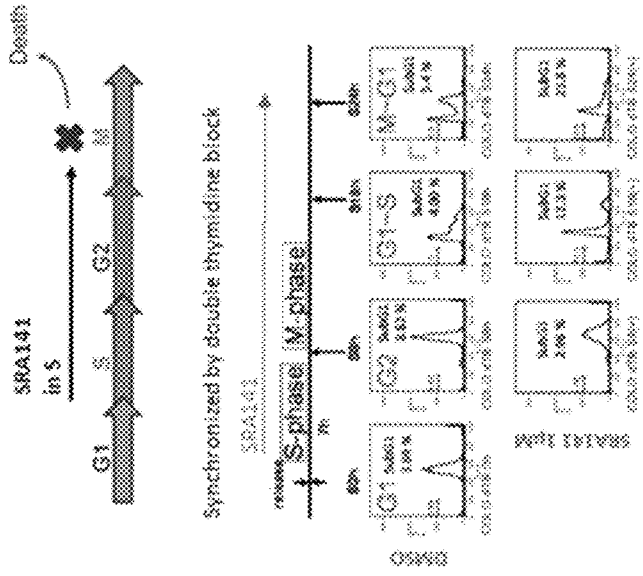

As shown in FIG. 15, flow cytometry analysis of cells labelled with propidium iodide demonstrated that a sub-G1 population, indicative of apoptotic cells, accumulated as the cells progressed through M phase provided they were treated with SRA141 during the preceding S phase (FIG. 15A), but not if the treatment started after S phase completion (beginning of M phase) (FIG. 15B). If SRA141 was added first at M phase, the sub-G1 accumulation was delayed and required that cells progress through a subsequent S phase in the presence of SRA141 before showing signs of apoptosis.

These data support the hypothesis that inhibition of Cdc7 functions in S phase, most likely replication origin firing mediated by MCM2/MCM4 phosphorylation, results in cells entering mitosis with under-replicated DNA, resulting in induction of apoptotic cell death.

Figure 15D:
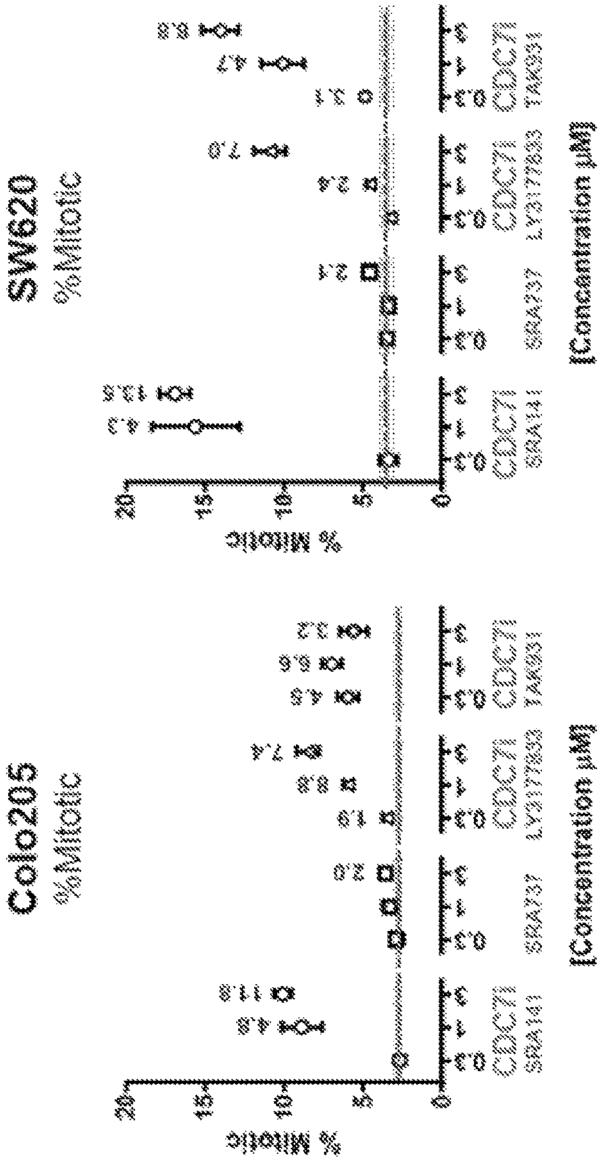
Figure 15C:
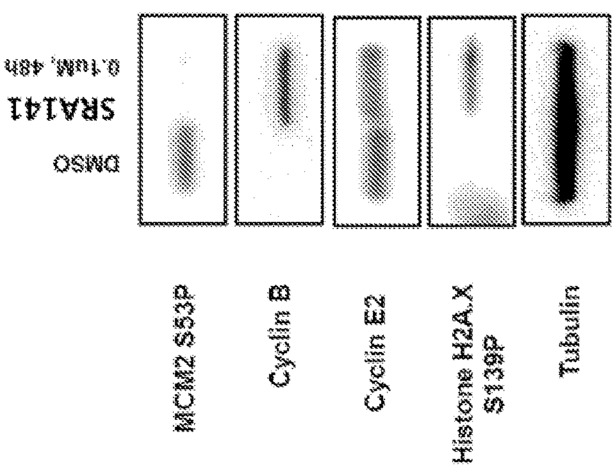

As shown in FIG. 15C, Colo-205 cells treated with 0.1 μM SRA141 for 48 hours were assessed for cell cycle and DNA damage markers by western blot. Results demonstrate the presence of mitotic markers of G2/M phase following treatment with SRA141. These results are consistent with data obtained by use of high content imaging that demonstrates that Colo-205 and SW620 cell populations treated with SRA141 for 48 hours have an accumulation of cells in mitosis (FIG. 15D). The percent of cells in mitosis is greater in populations treated with SRA141 compared to other Cdc7 inhibitors.

Example 12: In Vitro Cellular Genetic Sensitivity Analysis

Figure 16:
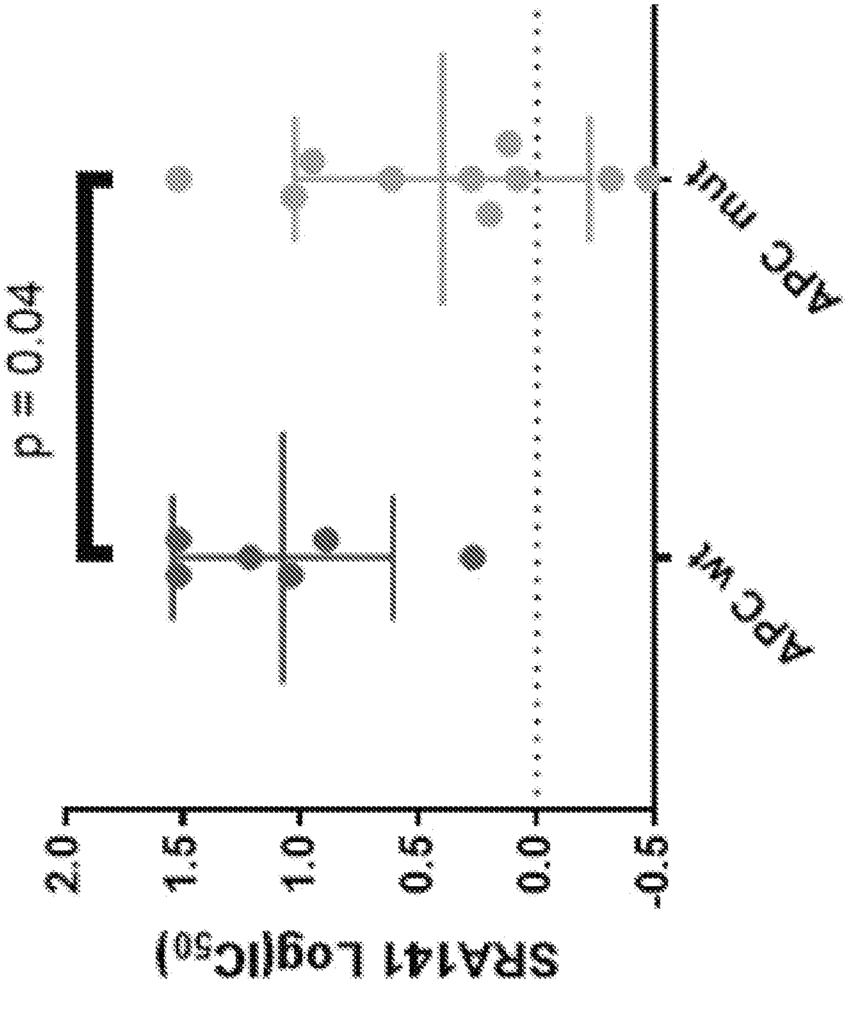
FIG. 16 shows a summary of SRA141 sensitivity in cell lines with and without APC mutations.

Analysis of SRA141 sensitivity of a 235-cell line panel demonstrated that colorectal cancer was among the most sensitive solid tumor lines (FIG. 16). Furthermore, bioinformatic analysis of genomics and methylation patterns of the 235 cell lines showed that mutations of FAT1 correlated with SRA141 sensitivity. Given the role of FAT1 in the Wnt signaling pathway that is commonly altered in colorectal cancer, we further examined the correlation between sensitivity of 16 colorectal cancer lines and presence of mutations in 2 other Wnt pathway genes, APC and FAT4.

The results show that APC mutations, which are commonly found in chromosomally unstable (CIN) colorectal tumors, were associated with increased sensitivity to SRA141 (p=0.04, FIG. 16). Although FAT4 mutations were not determined to be statistically correlated with SRA141 sensitivity, three of the most sensitive lines were found to harbor FAT4 mutations. These preliminary data support the use of SRA141 in CIN colorectal cancers.

Example 13: Colo-205 Colorectal Xenograft Study (Mouse)

Female BALB/c mice bearing Colo-205 tumor xenografts were orally administered (i) vehicle (0.2 M HCl/0.5% MC400) or (ii) SRA141 30 or 60 mg/kg BID for 17 days or (iii) SRA141 120 mg/kg QD for 17 days (n=8 per treatment group). Tumor growth inhibition was calculated on Day 16, the final day of the study.

All treatments were tolerated; however, dosing was temporarily suspended for two days for two mice from the SRA141 60 mg/kg BID and for 1 and 5 days for two mice from the 120 mg/kg QD treatment groups due to excessive body weight loss (>15% loss).

Figure 17:
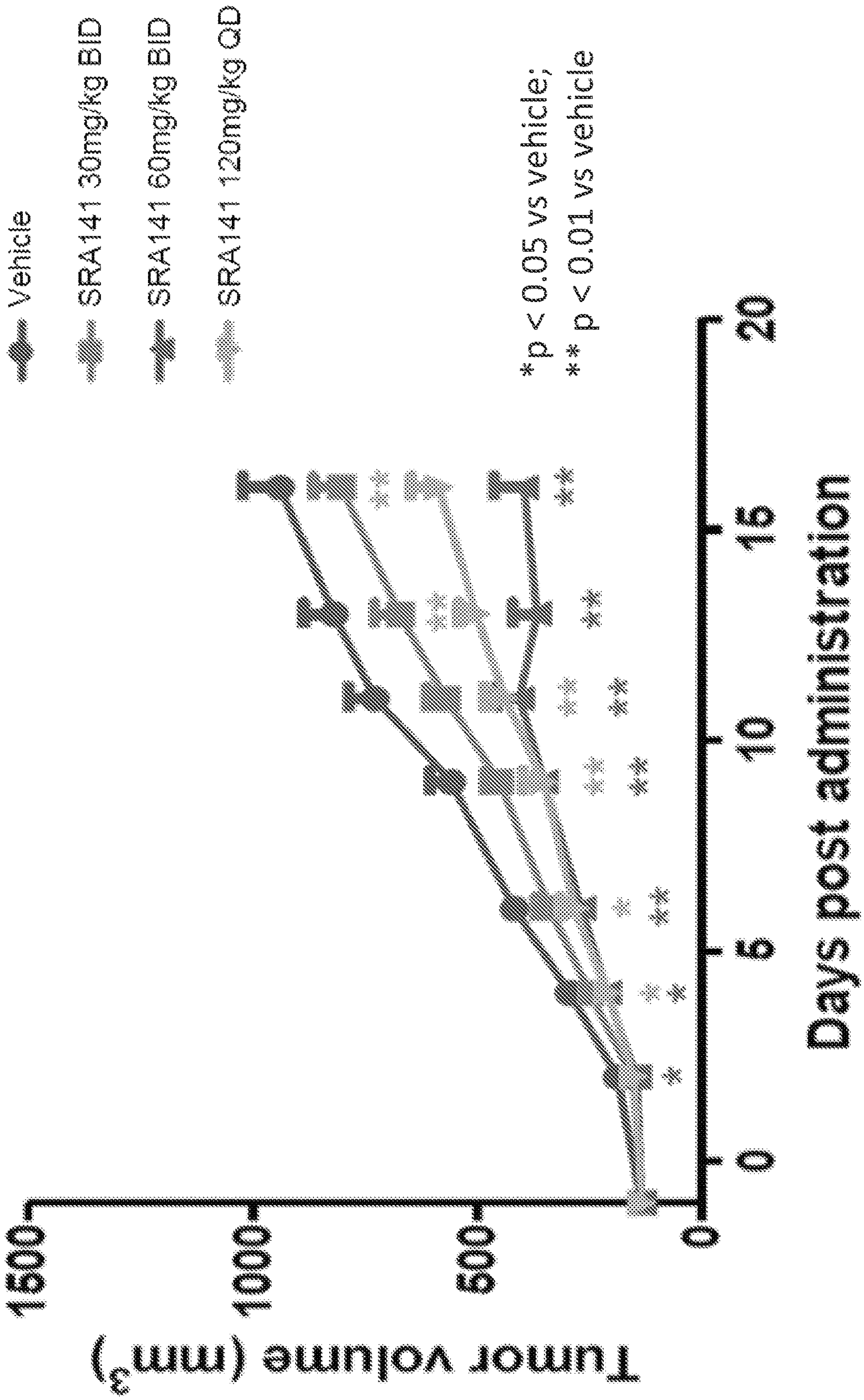
FIG. 17 is a graph showing mean tumor volumes of animals treated with SRA141 monotherapy in BALB/c mice bearing Colo-205 tumor xenografts.

As shown in FIG. 17, SRA141 administration resulted in tumor growth inhibition of 15%, 58% and 37% at the 30 mg/kg BID, 60 mg/kg BID and 120 mg/kg QD dose levels, respectively. These preliminary data support the use of SRA141 in colorectal cancers.

Example 14: SW620 Colorectal Xenograft Study (Mouse)

Female BALB/c mice bearing SW620 tumor xenografts were orally administered (i) vehicle (0.1 M HCl/0.5% MC400) or (ii) SRA141 60 mg/kg three times a day (TID) for 4 consecutive days followed by a 2-day dosing holiday for 21 days or (iii) SRA141 120 mg/kg QD for 21 days (n=10 per treatment group). Tumor growth inhibition was calculated on Day 21, the final day of the study. All vehicle control animals remained on study on Day 21.

Four of 10 mice treated with SRA141 at 60 mg/kg TID experienced a maximum body weight loss greater than 20%. Dosing to these animals was suspended until the body weight loss recovered to less than 20%. None of the mice treated with SRA141 120 mg/kg QD met the 20% weight loss threshold.

Figure 18:
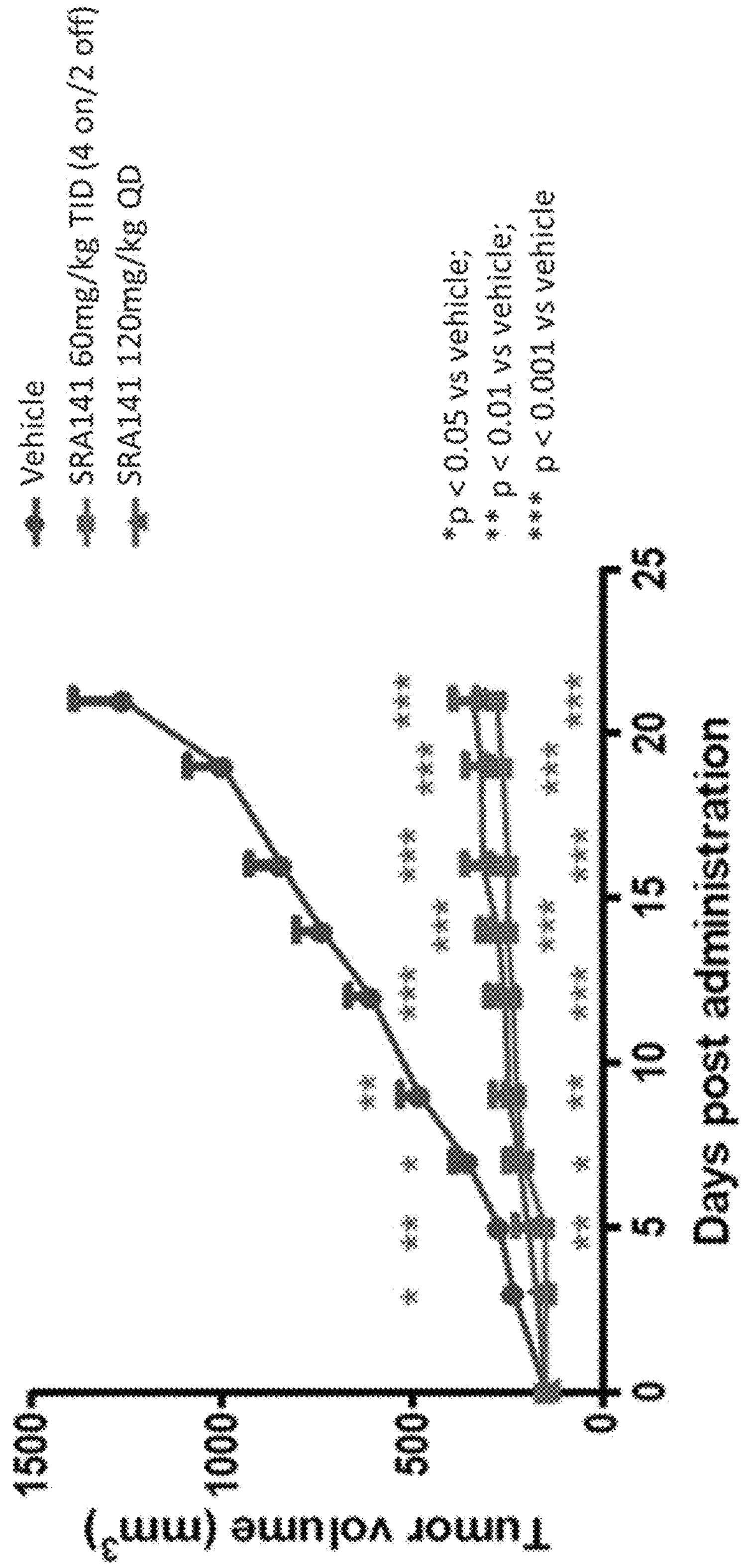
FIG. 18 is a graph showing mean tumor volumes of animals treated with SRA141 monotherapy in BALB/c mice bearing SW620 tumor xenografts.

As shown in FIG. 18, SRA141 administration resulted in tumor growth inhibition of 78% and 73% at 60 mg/kg TID and 120 mg/kg QD, respectively. These preliminary data support the use of SRA141 in colorectal cancers.

Example 15: MV-4-11 Human Leukemia Systemic Survival Study

Female NOD SCID mice intravenously inoculated with MV-4-11 cancer cells were administered (i) vehicle control (0.1 M HCl/0.5% MC400, oral) or (ii) SRA141 initially at 60 mg/kg BID for 5 consecutive days of a 7-day cycle from Days 0 to 21, and then due to significant body weight loss, at 40 mg/kg BID on the same schedule from Days 22 to 73 (n=10 per treatment group). Survival was the only efficacy endpoint in this study, given the systemic nature of the cancer model.

In general, treatment with SRA141 was tolerated based on body weight loss data. One of ten SRA141-treated mice experienced body weight loss greater than 20%.

Five animals in the SRA141 treatment group were found deceased on Days 17 and 18 of the study, probably due to technical error or tolerability rather than disease progression. The median survival for all animals, including premature decedents, was 66 and 35 days for the vehicle and SRA141 treatment groups respectively and greater than 99 days for the SRA141 treatment group with the premature decedents censored. Thus, the increase survival of the censored treatment group supports the use of SRA141 in leukemia treatments.

Example 16: A20 Immunocompetent Lymphoma Xenograft Model (Mouse)

Immunocompetent female BALB/c mice bearing A20 tumor xenografts were administered (i) control (PBS, intraperitoneal) or (ii) SRA141 120 mg/kg orally; n=8 animals per group). Dosing occurred on Days 0 to 4, 7 to 11, and 14 to 18. Tumor growth inhibition was calculated on Day 23, the final day of the study.

In general, treatment with SRA141 was tolerated. One animal experienced body weight loss greater than 20% and was subsequently euthanized.

Figure 19:
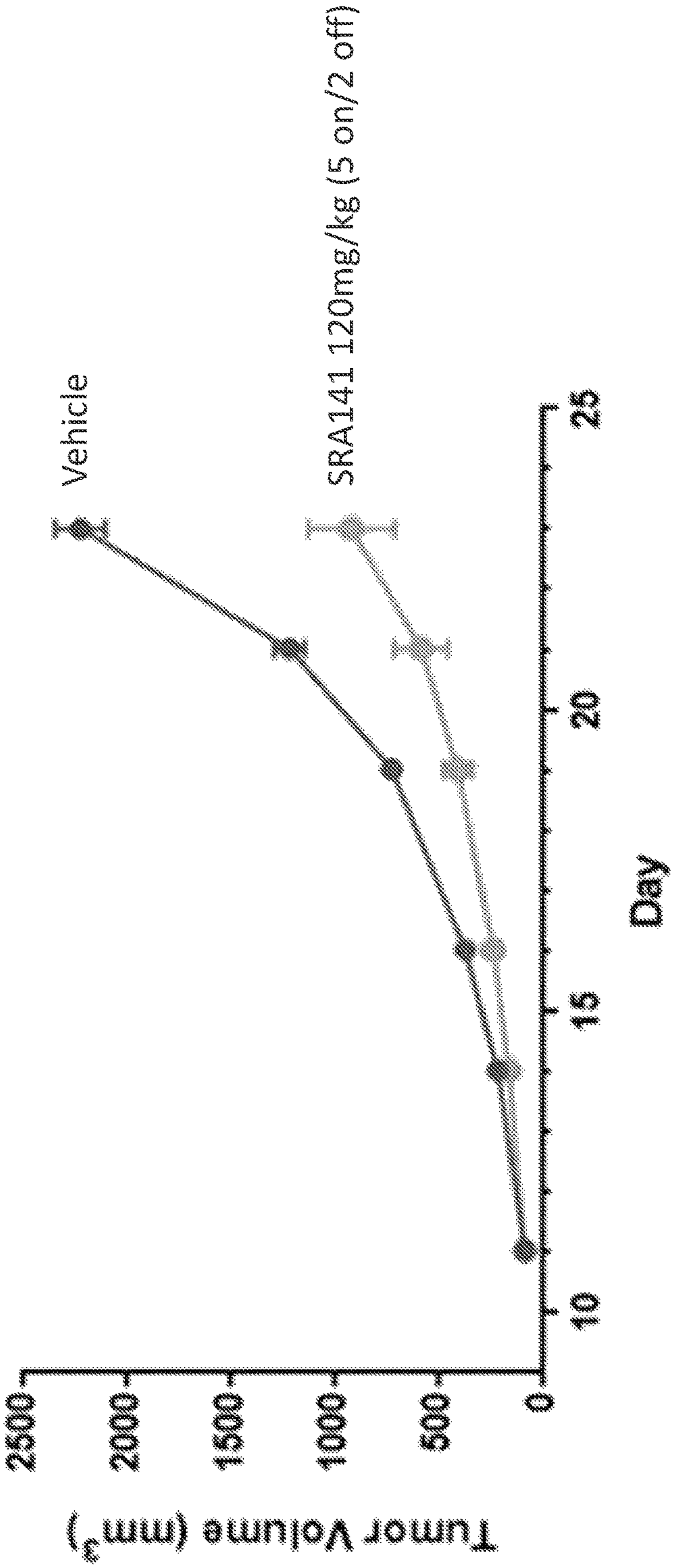
FIG. 19 is a graph showing mean tumor volumes of animals treated with SRA141 monotherapy in BALB/c mice bearing A20 tumor xenografts.

As shown in FIG. 19, SRA141 administration resulted in tumor growth inhibition of 59%. These preliminary data support the use of SRA141 in lymphomas.

Example 17: MDA-MB-486 Breast Xenograft Study (Mouse)

Female CB-17 SCID mice bearing MDA-MB-486 breast tumor xenografts were orally administered (i) vehicle control (0.1 M HCl/0.5% MC400) or (ii) SRA141 30 or 60 mg/kg BID for 5 weeks (n=10 per treatment group). Tumor growth inhibition was calculated on Day 35, the final day of the study.

The vehicle control and SRA141 at 30 mg/kg BID treatments were well tolerated.

Six of 10 mice treated with SRA141 at 60 mg/kg BID experienced a maximum body weight loss greater than 20%. Dosing was temporarily suspended to these animals on Days 18 and 19, with one animal euthanized due to prolonged body weight loss.

Figure 20:
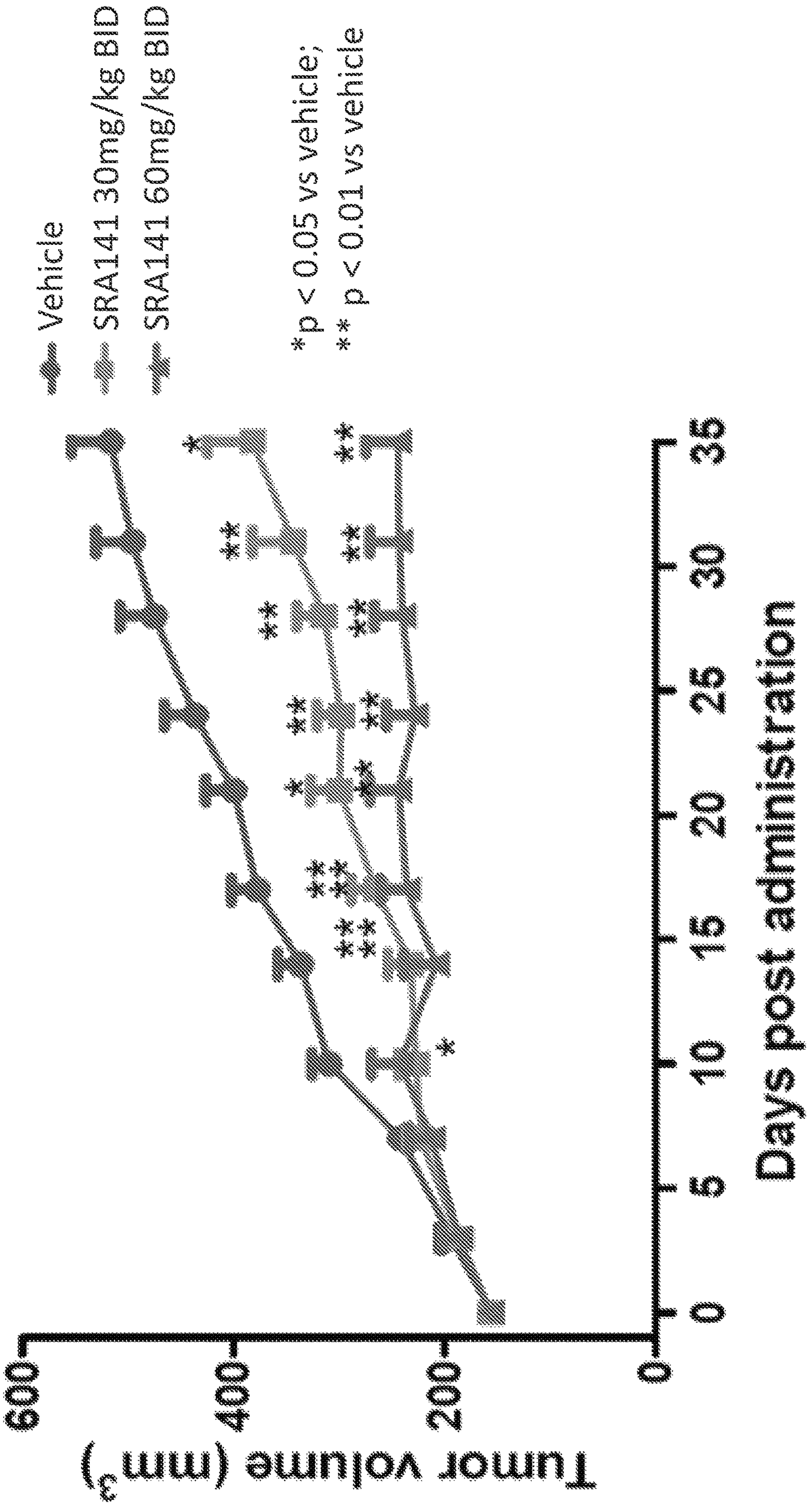
FIG. 20 is a graph showing mean tumor volumes of animals treated with SRA141 monotherapy in CB-17 SCID mice bearing MDA-MB-486 breast tumor xenografts.

As shown in FIG. 20, SRA141 administration resulted in tumor growth inhibition of 26% and 53% at 30 mg/kg BID and 60 mg/kg BID, respectively. These preliminary data support the use of SRA141 in breast cancers.

Example 18: Mouse SW620 Colorectal Xenograft Model PK/PD Assessment

The effect of SRA141 treatment on tumoral phospho-MCM2 (pMCM2), a direct substrate of Cdc7 and downstream marker of Cdc7 inhibition, was determined in mice bearing SW620 xenografts. Changes in pMCM2 were correlated with SRA141 concentrations in tumor and plasma over a 48-hour period following drug administration to construct a rudimentary PK/PD model.

Specifically, female BALB/c mice bearing subcutaneous SW620 tumors were administered single oral doses of SRA141 at 30, 60 or 120 mg/kg (n=15 per group). Control animals were administered vehicle (0.1 M HCl/0.5% MC400; n=10). At 2, 4, 8, 24 and 48 hours following treatment, three animals from each group (n=2 for control) were terminated, and plasma and tumor sampled for analysis.

Figure 21A:
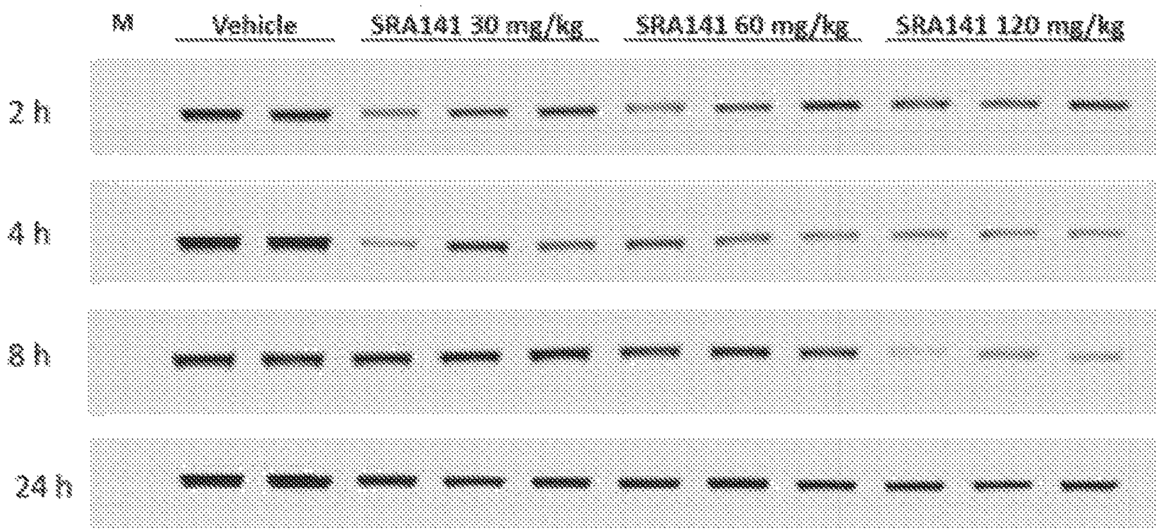
FIG. 21 shows pMCM2 levels decreased following a single SRA141 administration in BALB/c mice bearing subcutaneous SW620 tumors (pMCM2 levels shown in FIG. 21A, % inhibition quantified and normalized to actin in FIG. 21B).
Figure 21B:
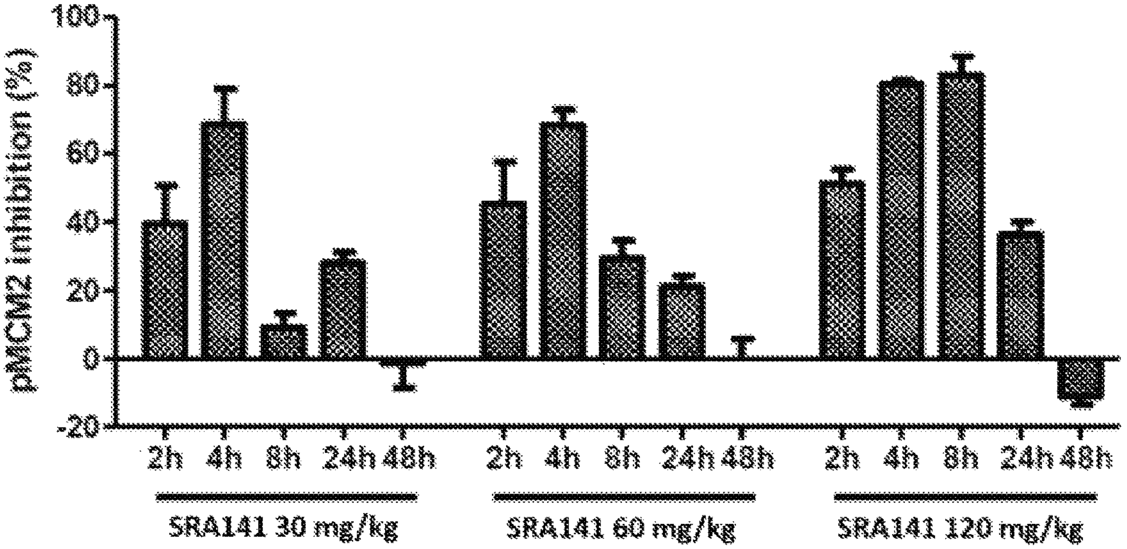

As shown in FIG. 21, pMCM2 levels decreased following a single SRA141 administration, peaking between 2-4 hours for 30 mg/kg and 60 mg/kg doses and between 2-8 hours for the 120 mg/kg dose (pMCM2 levels shown in FIG. 21A, % inhibition quantified and normalized to actin in FIG. 21B). Maximal SRA141 plasma concentrations of ca 1, 1.5, and 2 g/mL were also observed at 2 to 4 hours after administration at the 30, 60 and 120 mg/kg doses, respectively. Tumoral concentrations of drug were similar. Correlation of PK and PD data from this study suggested that a circulating plasma concentration and intra-tumoral tissue concentration of approximately 1.1 μM is required to inhibit pMCM2 by 50%.

Example 19: Rat Colo-205 Colorectal Xenograft Model PK/PD Assessment

Figure 22:
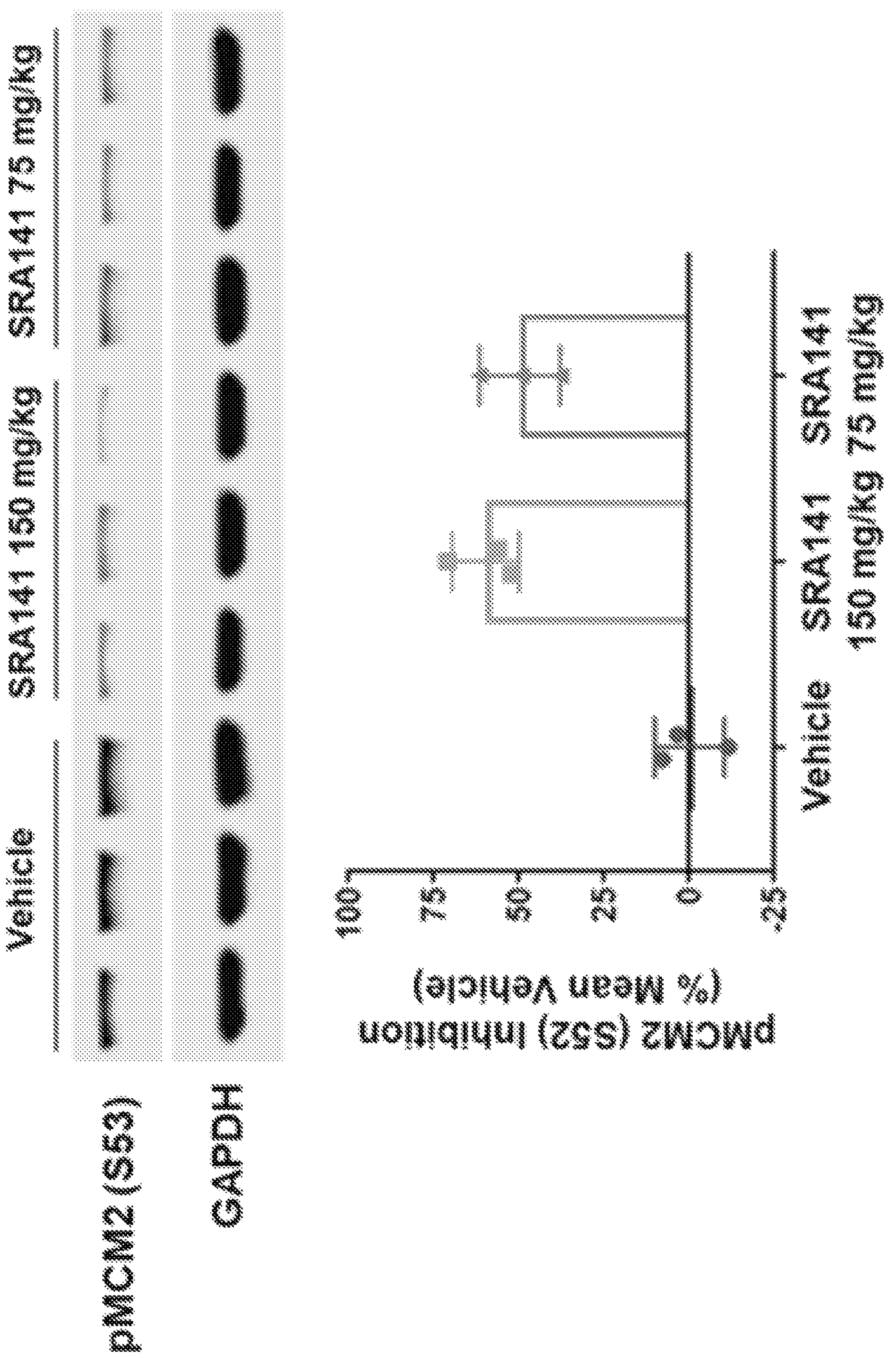
FIG. 22 shows pMCM2 levels following SRA141 treatment in female Rowett nude rats bearing subcutaneous Colo-205 tumors.

Tumoral inhibition of pMCM2 following SRA141 treatment was also determined in female Rowett nude rats bearing subcutaneous Colo-205 tumors. Twelve hours following a single oral dose of SRA141 (75 or 150 mg/kg), animals were terminated, and tumors were sampled for analysis (n=3 per group). Control animals were administered the same vehicle used in the Colo-205 rat model (see Example 5; n=3 per group). SRA141 tumor concentrations of ca 0.5 and 0.9 g/mL were observed at 12 hours after administration of the 75 and 150 mg/kg doses, respectively. Twelve hours after a single dose of SRA141, pMCM2 was inhibited approximately 50% to 60% of control (FIG. 22). These results suggest that intra-tumoral tissue concentrations of 1 μM are sufficient to inhibit MCM2 phosphorylation (pMCM2) by 50%.

Example 20: In Vivo Nonclinical Pharmacokinetics Summary

In vitro distribution studies showed SRA141 was highly bound to human and rat plasma protein (>90%) whereas moderate binding was observed in the mouse and dog matrices (58% to 77%). In addition, SRA141 did not preferentially partition into red blood cells in any species matrix.

In vitro metabolism studies conducted in preclinical and human hepatocytes indicate favorable metabolic stability of SRA141 in the rat, dog and human preparations. Eleven metabolites were identified across species, of which 6 occurred in the human matrix. One human-specific metabolite was identified, but only at trace levels. The mouse, rat and dog hepatocyte metabolite profiles contained all the other human metabolites.

At clinically relevant concentrations, SRA141 showed in vitro time and metabolism-dependent inhibition of CYP 3A4/5 (IC50=6.2 to 6.7 μM) and in vitro inhibition of human organic anion transporters OATP1B1, OATP1B3 and OAT3 (>50% inhibition at 10 μM). Collectively, these in vitro CYP and transporter inhibition data suggest SRA141 could potentially alter the metabolism and/or distribution of co-administered drugs known to be substrates for this CYP isoform or these transporters.

SRA141 (presented as free base suspension) demonstrated moderate absolute oral bioavailability (% F) in the fasted mouse, rat and dog, ranging from 31% to 54% with lower oral bioavailability evident in the monkey (% F=1% to 33%). Presentation as the bis-hydrochloride salt in suspension did not appear to significantly increase exposure in any species. Further studies in the dog suggested absolute oral bioavailability of the bis-hydrochloride salt in suspension may be improved following post-prandial administration. However, in a separate study in dogs, moderate absolute oral bioavailability was noted following administration of the two proposed clinical drug product capsule presentations (% F=41% to 62%) and prandial state appeared to have no appreciable effect on the oral bioavailability. Systemic exposure (Cmax, AUC) following oral dosing generally increased with increasing dose, but in a less than dose proportional manner.

Figure 23:
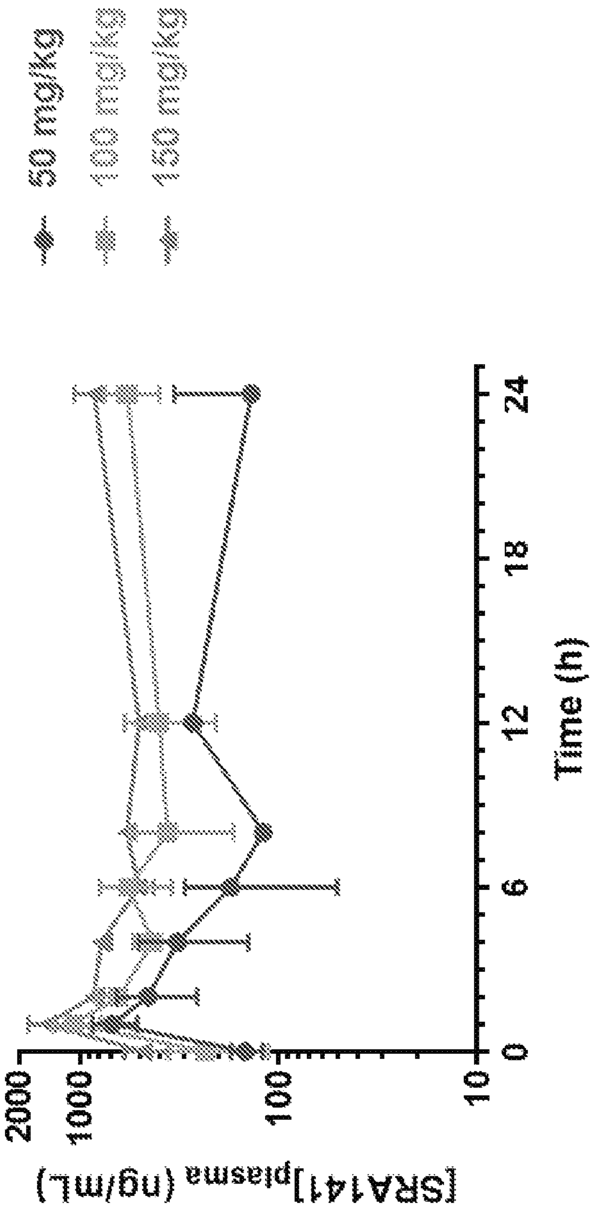
FIG. 23 shows SRA141 plasma concentrations determined by LC-MS/MS in non-tumor bearing female nude rats.

Non-tumor bearing female nude rats were treated orally with SRA141 (n=3 per route) at 50 mg/kg (QD×12 days) or 100 or 150 mg/kg (5 days on/2 days off/5 days on). The vehicle was 0.5% CMC-Na/1% Lutrol in water. SRA141 plasma concentrations were determined by LC-MS/MS following last dose. As shown in FIG. 23, systemic exposure increased with an increase in the oral dose from 50 to 150 mg/kg.

Example 21: In Vivo Nonclinical Toxicology Summary

Toxicology studies evaluating SRA141 were conducted in rat and dog following single and repeat oral dosing for up to 4 cycles (5 days on/2 days off per cycle). In addition, the potential genetic toxicity of SRA141 was evaluated in vitro. A summary of the findings in shown in Table 4.

TABLE 4

NOAEL, MTD and HNSTD and Associated Plasma Exposures in 4-Cycle Studies in Rats and Dogs

| | Species | Dose (mg/kg/day) | Dose (mg/m$_2$/day) | Cmax (ng/mL) | AUC24 h (ng · h/mL) |
|---|---|---|---|---|---|
| NOAEL | Rat | 50 | 300 | 289 (M) | 2,870 (M) |
| | | | | 711 (F) | 8,550 (F) |
| | Dog | 2 | 40 | 98 (M) | 859 (M) |
| | | | | 129 (F) | 804 (F) |
| MTD/HNSTD | Rat | 100 | 600 | 390 (M) | 5,130 (M) |
| | | | | 1,610 (F) | 29,000 (F) |
| | Dog | 10 | 200 | 497 (M) | 5,660 (M) |
| | | | | 576 (F) | 6,840 (F) |

M = Male;
F = Female

M=Male; F=Female

Findings from the rat and dog repeat-dose toxicity studies indicated potential target organs for SRA141-related toxicity are the gallbladder/biliary system, lymphoid tissues (spleen, thymus, lymph node and GALT), bone marrow, liver, kidney, male and female reproductive tract, peripheral leukocytes, and salivary gland, with the dog appearing to be the most sensitive species.

Effects on the biliary system were observed at high incidence and consistently in both rats and dogs. However, these biliary changes were generally minimal to mild and partially (biliary hyperplasia in both species) or completely reversible (gallbladder in the dog; tissue not present in rats). Furthermore, drug-induced biliary findings in animals have not been reliably predictive of similar findings in humans (Hailey, 2013; MacDonald, 2004).

Biliary and Kupffer cell changes were the only findings noted following 28-day repeat dose administration of SRA141 to the rat, with incidental hematologic and clinical chemistry changes. However, in the dose-ranging studies in rats, changes in other organs and tissues were identified including liver (hepatocellular degeneration), spleen (reduced red pulp cellularity) and stomach (inflammation and epithelial hyperplasia). Although it is not clear why comparable findings were not observed in the 28-day study in rats, the cyclical administration of drug in the pivotal study may have contributed to the different toxicological outcomes. The similarity of some of the tissue changes beyond the biliary system in the 7-day rat study and 28-day dog study, despite differences in formulation, doses and dosing duration, suggest that the dog may be more sensitive than the rat to SRA141.

Although zygomatic salivary gland changes would be considered adverse for the affected dogs, the low incidence and lack of a comparable salivary gland in humans makes this potential target of uncertain clinical relevance to humans. Similarly, the low magnitude of change and recoverability of changes in lymphoid tissues, along with the cyclical changes in peripheral leukocytes related to the intermittent dose cycle are not judged to be adverse; these changes may be inter-related and may represent transient tissue and peripheral blood alterations in leukocyte trafficking. The potentially adverse reduced cellularity of bone marrow may also be related to this proposed change in leukocyte trafficking. Thymic reductions were more severe than other lymphoid tissue changes, but this tissue change may be partially or entirely secondary to stress and not reflective of a direct SR141-related toxicity.

In the 28-day dog study, there appeared to be potential sex differences with males more affected by changes in the gallbladder, kidney tubule and bone marrow. However, the small number of animals in each test group and low magnitude of difference between sexes does not allow for definitive determination of a specific sex difference in tissue responses.

SRA141 was negative for both mutagenicity and clastogenicity in in vitro bacterial reverse mutation and human lymphocyte chromosomal aberration assays.

In conclusion, the results from these studies indicate that the toxicity findings after administration of SRA141 are generally monitorable in a clinical setting, supportive therapies are available and/or are less relevant in an advanced oncology study population. Specifically, the MTD and highest-non-severely-toxic dose (HNSTD) following a 5 days on/2 days off dosing schedule for 4 weeks were considered to be 100 mg/kg/day (600 mg/m2/day) and 10 mg/kg/day (200 mg/m2/day) in rats and dogs, respectively.

Example 22: SRA141 CRC Clinical Trial

Clinical trials are conducted to confirm the efficacy of SRA141 monotherapies in the treatment of cancer in patients with metastatic CRC of the CIN phenotype enriched for by the exclusion of patients who do have MSI-H status, while other cancers with high rates of chromosome instability, in some cases, are explored in the future.

The human equivalent starting dose for oncology clinical trials is typically the lesser of 1/10th the severely toxic dose in 10% of rodents (STD10) or 1/6th the highest non-severely toxic dose (HNSTD) in non-rodents (ICH S9, 2009). Data from the GLP pivotal toxicology studies (see Example 21) indicated a maximum tolerated dose (MTD as a surrogate for the STD10) of 100 mg/kg/day (600 mg/m2/day; the highest dose tested) in the rat and a HNSTD of 10 mg/kg/day (200 mg/m2/day) in the dog as the more sensitive species. Consequently, a Human Equivalent Dose (HED) of 33.3 mg/m2/day (0.90 mg/kg/day) equating to an absolute dose of 54 mg (for a 60 kg patient) is utilized. For the extra assurance of subject safety, a lower SRA141 starting dose of 10 mg, administered orally, is used.

The clinical dosing schedule conforms with the preclinical dosing schedule that have demonstrated antitumor activities, i.e., 5 days on/2 days off. SRA141 is supplied in hydroxypropyl methylcellulose (HPMC) capsules. SRA141 capsules are taken on an empty stomach (subjects fast for at least 2 hours pre- and 1 hour post-administration) unless guided by the Sponsor based on additional data.

Dose Escalation Stage

A Dose Escalation Stage is conducted. Between 15 and 50 subjects with metastatic CRC are enrolled. An accelerated titration design is utilized. Cohorts initially consisting of a single subject receive escalating doses of SRA141. Initial dose escalations proceed in increments as large as 100% as deemed clinically appropriate based on the emerging safety profile. Once SRA141-related National Cancer Institute-Common Terminology Criteria for Adverse Events (NCI-CTCAE) Grade 2 or greater toxicity is observed during Cycle 1 in a particular cohort, that cohort is expanded to 3 to 6 subjects, and subsequent dose level cohorts follow a rolling 6 design. The dose of SRA141 is escalated thereafter in increments to be determined after review of all available safety data. The dose of SRA141 is escalated until the MTD has been identified, unless determined otherwise by the sponsor, for example if an alternative schedule is pursued. Dose escalation with alternative schedules begin at any time and either run in parallel or instead of continued dose escalations in the original schedule.

The DLT evaluation period is from the first dose on Cycle 1 Day 1 to the end of the first cycle of treatment. Subjects who are not evaluable for DLT assessments, for example, not completing the DLT evaluation period for reasons other than intolerability/toxicity of SRA141, in some cases are replaced.

A DLT is defined as any of the following events (by NCI-CTCAE v4.03) if deemed highly probably or probably related to SRA141:

- Grade 4 neutropenia, anemia, or thrombocytopenia that lasts for >7 days despite withholding dosing and/or providing supportive care;
- Grade 4 febrile neutropenia;
- ≥Grade 3 thrombocytopenia with ≥Grade 3 bleeding;
- ≥Grade 3 nonhematological toxicity with exceptions relating to Grade 3 nausea, vomiting and/or diarrhea in the absence of adequate prophylaxis or treatment, fatigue, and transient and asymptomatic Grade 3 lab abnormalities; (refer to protocol for details)
- Inability to receive 75% of the planned doses of SRA141 due to intolerability or toxicity.

Dose-limiting toxicities are considered for the purposes of dose escalation decisions; however, should cumulative toxicity become apparent this is taken into consideration when determining the next dose level in escalation or the RP2D.

Dose Expansion Stage

A Dose Expansion Stage is also conducted. Approximately 30 subjects with metastatic CRC whose tumors are not of known high microsatellite instability (MSI-H) status are enrolled into a single expansion cohort to further characterize the safety profile and to assess preliminary efficacy. The enrollment for the expansion cohort in some cases are starts prior to the determination of MTD or RP2D if there is evidence of antitumor activity or if the SRA141 plasma concentration reaches the minimum efficacious threshold as based on emerging nonclinical data. SRA141 is administered at the proposed RP2D and schedule based on the results of the Dose Escalation stage of the trial. The RP2D of SRA141 in some cases is equal to or below the MTD. Alternatively, if enrollment is initiated prior to the determination of RP2D, SRA141 is administered initially at the highest dose that has been cleared during the Dose Escalation stage at the time of each subject's enrollment. Once a higher dose level for the same schedule is determined to be safe in an Escalation cohort, the subject in some cases is allowed to escalate to the higher dose level.

Methodology

SRA141 treatment is administered orally once a day on a 5 days on/2 days off schedule in a 28-day cycle in initial cohort(s). Alternative dosing schedules are considered based on emerging safety and tolerability data.

The trial consists of Screening, Treatment, Safety follow-up (SFU) and Long-term follow-up. The Treatment period in some cases continues until one of the pre-specified criteria, including disease progression, unacceptable toxicity, and pregnancy, is met.

Screening and baseline assessments are performed for: demographics, disease history, baseline disease assessments, baseline safety assessments, and pregnancy test for WOCBP subjects. Pretreatment (baseline) samples for PDn and retrospective genomic assessments are collected.

Safety assessments are performed:

- continuous adverse event (AE) evaluations and review of concomitant treatments;
- vital signs weekly at predose and 2 to 3 hours postdose during Cycle 1 and on Day 1 of each subsequent cycle, and at SFU;
- clinical biochemistry weekly during Cycles 1 and 2 and biweekly from Cycle 3, then monthly from Cycle 7 onward, and at SFU;
- hematology weekly during Cycles 1 to 3 and biweekly in subsequent cycles, and at SFU;
- troponin at SFU; urinalysis on Day 1 of each cycle and at SFU;
- echocardiogram on Cycle 2 Day 1 and at SFU;
- electrocardiogram (ECG) (locally-read) on Day 1 of Cycles 1, 2, and every third subsequent cycle, and at SFU;
- central ECG on Cycle 1 Days 1 and 19 (at multiple timepoints postdose); and
- symptoms-directed physical examination as clinically indicated.

In addition, intensive blood pressure monitoring including orthostatic vital signs are performed after the first dose of SRA141 on Cycle 1 Day 1.

Efficacy is assessed:

- tumor assessments by CT/MRI of chest, abdomen, pelvis, and all suspected sites of disease, every 8 weeks after Cycle 1 Day 1 and at SFU except for subjects who discontinue for documented disease progression;
- clinical assessments and serum carcinoembryonic antigen (CEA) level every 4 weeks after Cycle 1 Day 1 and at SFU; and
- survival status Pharmacokiectics are assessed:

- 24-hours of intensive PK sampling on Cycle 1 Days 1 and 19.
- predose sampling on Day 1 of C3, 4, 5, and 8

Pharmacodynamics are assessed. Surrogate tissue (skin punch biopsy) and tumor tissue are collected and analyzed for the PDn biomarker pMCM2. Skin punch samples are collected at Baseline and on Cycle 1 Day 18 or 19 at 4 to 8 hours post dose (i.e., anticipated Cmax of SRA141). A third skin punch biopsy at a later timepoint in Cycle 1 or later cycles, when plasma concentration of SRA141 reaches trough level (Cmin) in some cases are collected from subjects who receive SRA141 dose levels above which measurable biomarker effects have been observed from the 4 to 8 hours post dose biopsy from Day 18 or 19. The timing of the third skin punch biopsy is communicated by the sponsor based on emerging PK and PDn data. Skin biopsy samples are required from all subjects enrolled in the Escalation Dose stage and a minimum of 10 subjects in the Expansion Dose stage. Tumor tissue is required from a minimum of 6 subjects in the Expansion Dose stage at Baseline and on Cycle 1 Day 4 or Day 5, at 4 to 8 hours postdose. Tumor tissues from additional subjects in the Expansion Dose stage and from subjects in the Escalation Dose stage are optional.

Genomics are assessed. Archival or fresh tumor tissue (primary or metastatic) and a blood sample are collected for retrospective genomic analyses at Baseline to explore genomic alterations that are associated with SRA141 treatment response. A blood sample is also collected at SFU.

Inclusion Criteria

Subjects for the clinical trial are selected based on the following criteria:

- Written informed consent prior to any trial specific procedures, sampling and analyses
- Attained the age of 18 years at the time consent is given
- Histologically and/or cytologically confirmed metastatic CRC
- Prior treatment with regimens containing fluorouracil or capecitabine, oxaliplatin, and irinotecan
- Life expectancy of at least 12 weeks
- Hematological and biochemical indices within the ranges shown in Table 5, measured within 1 week prior to the subject receiving their first dose of IMP

TABLE 5

Hematological and biochemical indices for inclusion

| Laboratory Test | Value required |
|---|---|
| Hemoglobin | ≥90 g/L |
| Absolute neutrophil count | ≥1.5 × $10^9$/L |
| Platelet count | ≥120 × $10^9$/L |
| Bilirubin | ≤1.5 × upper limit of normal (ULN) unless due to Gilbert's syndrome in which case up to 3 × ULN is permissible |
| Alanine aminotransferase (ALT), aspartate aminotransferase (AST) and alkaline phosphatase (ALP) | ≤2.5 × ULN For the Expansion stage, up to 5 × ULN is permissible if the increase is due to tumor. |
| Serum creatinine | ≤1.5 × ULN |

TABLE 5-continued

| Hematological and biochemical indices for inclusion | |
|---|---|
| Laboratory Test | Value required |
| or | or |
| Calculated creatinine clearance | ≥60 mL/min using Cockcroft-Gault formula |

World Health Organization (WHO) performance status 0-1

Radiographically measurable disease per RECIST criteria

Archival tumor tissue collected within 18 months prior to the first dose of IMP or approved by sponsor and available for retrospective tumor profiling or accessible tumor and willingness to consent to a biopsy for the collection of tumor tissue For a minimum of 6 subjects enrolled to the Expansion stage, accessible tumor and a willingness to consent to up to 2 tumor biopsies for the collection of tumor tissue for PDn assays Exclusion Criteria Subjects are excluded from the clinical trial based on the following criteria:

Any prior treatment with a Cdc7 inhibitor

Colorectal cancer with known high microsatellite instability, i.e., MSI-H

Have received the following prior or current anticancer therapy:

a. Radiotherapy of any target lesions (lesions used as measurable disease) within 4 weeks prior to the first dose of SRA141 (except for symptom control and where the lesions will not be used as measurable disease)
b. Chemotherapy within 3 weeks prior to the first dose of SRA141
c. Previous immunotherapy within 4 weeks, or 5 half-lives if it is shorter and approved by the sponsor, prior to the first dose of SRA141
d. Nitrosoureas or Mitomycin C within 6 weeks prior to the first dose of SRA141
e. Other IMPs or targeted therapy within 4 weeks, or 5 half-lives if it is shorter and approved by the sponsor, prior to the first dose of SRA141

Concurrent administration of naturopathic medications, herbal supplements, or other alternative therapies which, in the view of the investigator, are known to affect CYP450 enzymes Current non-prescription drug or alcohol dependence that in the view of the investigator is severe enough to affect study compliance or safety Other malignancy within the past 2 years with the exception of adequately treated tumors that are associated with an expected 5-year disease-free survival of approximately 95% or better, unless approved by the sponsor Ongoing toxic manifestations of previous treatments greater than NCI-CTCAE Grade 1. Exceptions to this are alopecia or certain toxicities, which in the opinion of the investigator and the sponsor or sponsor's designee monitor should not exclude the subject New or progressing brain metastases. History of central nervous system metastasis in the past 6 months (expansion cohort only). Subjects with brain metastases that have been radiologically stable over an 8-week period in some cases are included in the escalation cohort Women who are already pregnant or lactating. Women of childbearing potential (WOCBP) unless they have a negative screening (ie, within 7 days prior to first dose) serum or urine pregnancy test and agree to follow the contraceptive requirements effective from the first administration of IMP, throughout the trial and for 6 months afterwards Men with partners of childbearing potential unless they agree to take measures not to father children by following the contraceptive requirements throughout the trial and for 6 months afterwards. Subjects with pregnant or lactating partners must be advised to use condom plus spermicidal gel to prevent exposure of the fetus or neonate throughout the trial and for 6 months after the last dose of SRA141

Major surgery from which the subject has not yet recovered

At high medical risk because of nonmalignant systemic disease including active uncontrolled infection Known to be serologically positive for hepatitis B, hepatitis C or human immunodeficiency virus (HIV), unless controlled with negative viral load and approved by the sponsor Serious cardiac or cardiovascular condition, such as concurrent congestive heart failure, prior history of class III/IV cardiac disease according to the New York Heart Association [NYHA] criteria, left ventricular ejection fraction <45% at baseline, history of cardiac ischemia within the past 6 months, prior history of significant cardiac arrhythmia requiring treatment, prior history of ischemic cerebral vascular disease or symptomatic peripheral vascular disease, unless approved by the sponsor QTcF >450 msec in adult males and >470 msec in adult females Prior bone marrow transplant or extensive radiotherapy to greater than 25% of bone marrow within 8 weeks prior to the first dose of IMP Impairment of gastrointestinal (GI) function or GI disease that in some cases significantly alters the absorption of IMP (eg, ulcerative diseases, uncontrolled nausea, vomiting, diarrhea, or malabsorption syndrome)

Not able to swallow capsules without chewing or crushing

Known allergies, hypersensitivity, or intolerance to SRA141 or its excipients

Is a participant or plans to participate in another interventional clinical trial, whilst taking part in this trial. Participation in an observational trial or interventional clinical trial which does not involve administration of an IMP and which would not place an unacceptable burden on the subject in the opinion of the investigator and sponsor or sponsor's designee would be acceptable Any other condition which in the investigator's or sponsor's opinion would not make the subject a good candidate for the clinical trial.

RECIST Criteria

Assessment of disease response in this study are performed according to the revised RECIST criteria v1.1. RECIST criteria are described in greater detail in Eisenhauer, et al. (New response evaluation criteria in solid tumours: Revised RECIST guideline (version 1.1). *Eur J Cancer* [*Internet*]. 2009), herein incorporated by reference for all it teaches.

At baseline, tumor lesions/lymph nodes are generally categorized measurable or non-measurable as follows:

Measurable

Tumor lesions: are generally accurately measured in at least one dimension (longest diameter in the plane of measurement is to be recorded) with a minimum size of:

10 mm by CT scan (CT scan slice thickness no greater than 5 mm; see Appendix II in Eisenhauer, et al., [Eisenhauer, 2009] on imaging guidance)

10 mm caliper measurement by clinical exam (lesions which cannot be accurately measured with calipers should be recorded as non-measurable)

20 mm by chest X-ray

Malignant lymph nodes: To be considered pathologically enlarged and measurable, a lymph node is generally 15 mm in the short axis when assessed by CT scan (CT scan slice thickness recommended to be no greater than 5 mm). At baseline and in follow-up, only the short axis is generally measured and followed.

Non-Measurable

All other lesions, including small lesions (longest diameter <10 mm or pathological lymph nodes with ≥10 to <15 mm short axis) as well as truly non-measurable lesions. Lesions considered truly non-measurable generally include: leptomeningeal disease, ascites, pleural or pericardial effusion, inflammatory breast disease, lymphangitic involvement of skin or lung, abdominal masses/abdominal organomegaly identified by physical exam that is not measurable by reproducible imaging techniques.

Bone lesions, cystic lesions, and lesions previously treated with local therapy require particular comment:

Bone lesions:

Bone scan, PET scan or plain films are generally not considered adequate imaging techniques to measure bone lesions. However, these techniques can be used to confirm the presence or disappearance of bone lesions.

Lytic bone lesions or mixed lytic-blastic lesions, with identifiable soft tissue components, that can be evaluated by cross sectional imaging techniques such as CT or MRI are generally considered as measurable lesions if the soft tissue component meets the definition of measurability described above.

Blastic bone lesions are generally non-measurable.

Cystic lesions:

Lesions that meet the criteria for radiographically defined simple cysts are generally not considered as malignant lesions (neither measurable nor non-measurable) since they are, by definition, simple cysts.

'Cystic lesions' thought to represent cystic metastases are generally considered as measurable lesions, if they meet the definition of measurability described above. However, if non-cystic lesions are present in the same subject, these are preferred for selection as target lesions.

Lesions with prior local treatment:

Tumor lesions situated in a previously irradiated area, or in an area subjected to other loco-regional therapy, are usually not considered measurable unless there is demonstrated progression in the lesion. Study protocols generally detail the conditions under which such lesions are generally considered measurable.

Method of Assessment

All measurements are generally recorded in metric notation, using calipers if clinically assessed. All baseline evaluations are generally performed as close as possible to the treatment start and never more than 4 weeks before the beginning of the treatment.

The same method of assessment and the same technique are generally used to characterize each identified and reported lesion at baseline and during follow-up. Imaging based evaluation are generally always done rather than clinical examination unless the lesion(s) being followed cannot be imaged but are assessable by clinical exam.

Clinical lesions are generally considered measurable when they are superficial and ≥10 mm diameter as assessed using calipers (e.g. skin nodules). For the case of skin lesions, documentation by color photography including a ruler to estimate the size of the lesion is suggested. As noted above, when lesions can be evaluated by both clinical exam and imaging, imaging evaluation is generally undertaken since it is more objective and in some cases is also reviewed at the end of the study.

Chest CT is generally preferred over chest X-ray, particularly when progression is an important endpoint, since CT is more sensitive than X-ray, particularly in identifying new lesions. However, in some cases, lesions on chest X-ray are considered measurable if they are clearly defined and surrounded by aerated lung CT is generally the best currently available and reproducible method to measure lesions selected for response assessment. This guideline has defined measurability of lesions on CT scan based on the assumption that CT slice thickness is 5 mm or less. When CT scans have slice thickness greater than 5 mm, the minimum size for a measurable lesion is twice the slice thickness. MRI is also acceptable in certain situations (e.g. for body scans). More details concerning the use of both CT and MRI for assessment of objective tumor response evaluation are provided in the publication from Eisenhauer et al.

Ultrasound is generally not useful in assessment of lesion size and is generally not used as a method of measurement. Ultrasound examinations in general cannot be reproduced in their entirety for independent review at a later date and, because they are operator dependent, it generally cannot be guaranteed that the same technique and measurements will be taken from one assessment to the next (described in greater detail in Eisenhauer, et al. (2009). If new lesions are identified by ultrasound in the course of the study, confirmation by CT or MRI is generally advised. If there is concern about radiation exposure at CT, MRI in some cases is used instead of CT in selected instances.

The utilization of endoscopy and laparoscopy techniques for objective tumor evaluation is generally not advised. However, they are in general useful to confirm complete pathological response when biopsies are obtained or to determine relapse in trials where recurrence following complete response or surgical resection is an endpoint.

Tumor markers alone are generally not used to assess objective tumor response. If markers are initially above the upper normal limit, however, they are generally normalized for a subject to be considered in complete response.

Cytology and histology are generally used to differentiate between PR and CR in rare cases if required by protocol (for example, residual lesions in tumor types such as germ cell tumors, where known residual benign tumors can remain). When effusions are known to be a potential adverse effect of treatment (e.g. with certain taxane compounds or angiogenesis inhibitors), the cytological confirmation of the neoplastic origin of any effusion that appears or worsens during treatment are generally considered if the measurable tumor has met criteria for response or stable disease in order to differentiate between response (or stable disease) and progressive disease.

Tumor Response Evaluation

To assess objective response or future progression, the overall tumor burden at baseline is generally estimated and used as a comparator for subsequent measurements.

Measurable disease is generally defined by the presence of at least one measurable lesion.

When more than one measurable lesion is present at baseline all lesions up to a maximum of five lesions total (and a maximum of two lesions per organ) representative of all involved organs are generally identified as target lesions and are recorded and measured at baseline (this means in instances where subjects have only one or two organ sites involved a maximum of two and four lesions respectively are recorded). Target lesions are generally selected on the basis of their size (lesions with the longest diameter) and are generally representative of all involved organs, but in addition are generally those that lend themselves to reproducible repeated measurements. In some cases, the largest lesion does not lend itself to reproducible measurement in which circumstance the next largest lesion which can be measured reproducibly is generally selected, as exemplified in FIG. 3 Eisenhauer, et al. (2009).

Lymph nodes merit special mention since they are normal anatomical structures which in some cases are visible by imaging even if not involved by tumor. Pathological nodes which are defined as measurable and in some cases are identified as target lesions in general meets the criterion of a short axis of ≥15 mm by CT scan. Only the short axis of these nodes generally contributes to the baseline sum. The short axis of the node is generally the diameter normally used by radiologists to judge if a node is involved by solid tumor. Nodal size is normally reported as two dimensions in the plane in which the image is obtained (for CT scan this is almost always the axial plane; for MRI the plane of acquisition in some cases are axial, sagital or coronal). The smaller of these measures is the short axis. For example, an abdominal node which is reported as being 20 mm×30 mm has a short axis of 20 mm and qualifies as a malignant, measurable node. In this example, 20 mm should be recorded as the node measurement. All other pathological nodes (those with short axis 10 mm but <15 mm) are generally considered non-target lesions. Nodes that have a short axis <10 mm are generally considered non-pathological and are generally not recorded or followed.

A sum of the diameters (longest for non-nodal lesions, short axis for nodal lesions) for all target lesions is generally calculated and reported as the baseline sum diameters. If lymph nodes are to be included in the sum, then as noted above, only the short axis is added into the sum. The baseline sum diameters are generally used as reference to further characterize any objective tumor regression in the measurable dimension of the disease.

All other lesions (or sites of disease) including pathological lymph nodes are generally identified as non-target lesions and are generally recorded at baseline. Measurements are generally not required and these lesions are generally followed as 'present', 'absent', or in rare cases 'unequivocal progression' (more details to follow). In addition, it is possible to record multiple non-target lesions involving the same organ as a single item on the case record form (e.g. 'multiple enlarged pelvic lymph nodes' or 'multiple liver metastases').

Response Criteria

Complete Response (CR): Disappearance of all target lesions. Any pathological lymph nodes (whether target or non-target) are reduced in short axis to <10 mm.

Partial Response (PR): At least a 30% decrease in the sum of diameters of target lesions, taking as reference the baseline sum diameters.

Progressive Disease (PD): At least a 20% increase in the sum of diameters of target lesions, taking as reference the smallest sum (this includes the baseline sum if that is the smallest on study). In addition to the relative increase of 20%, the sum generally demonstrates an absolute increase of at least 5 mm. (Note: the appearance of one or more new lesions is generally also considered progression).

Stable Disease (SD): Neither sufficient shrinkage to qualify for PR nor sufficient increase to qualify for PD, taking as reference the smallest sum diameters.

Lymph nodes identified as target lesions generally record the actual short axis measurement (measured in the same anatomical plane as the baseline examination), generally even if the nodes regress to below 10 mm. This means that when lymph nodes are included as target lesions, the 'sum' of lesions in some cases are not be zero even if complete response criteria are met, since a normal lymph node is generally defined as having a short axis of <10 mm. Case report forms or other data collection methods in some cases are therefore designed to have target nodal lesions recorded in a separate section where, in order to qualify for CR, each node generally achieves a short axis <10 mm. For PR, SD and PD, the actual short axis measurement of the nodes is preferably included in the sum of target lesions.

While on study, all lesions (nodal and non-nodal) recorded at baseline generally record their actual measurements at each subsequent evaluation, even when very small (e.g. 2 mm). However, sometimes lesions or lymph nodes which are recorded as target lesions at baseline become so faint on CT scan that the radiologist in some cases does not feel comfortable assigning an exact measure and in some cases report them as being 'too small to measure'. When this occurs it is in general important that a value is recorded on the case report form. If it is the opinion of the radiologist that the lesion has likely disappeared, the measurement is generally recorded as 0 mm. If the lesion is believed to be present and is faintly seen but too small to measure, a default value of 5 mm is generally assigned. (Note: It is in general less likely that this rule is used for lymph nodes since they usually have a definable size when normal and are frequently surrounded by fat such as in the retroperitoneum; however, if a lymph node is believed to be present and is faintly seen but too small to measure, a default value of 5 mm is generally assigned in this circumstance as well). This default value is derived from the 5 mm CT slice thickness (but generally is not changed with varying CT slice thickness). The measurement of these lesions is potentially non-reproducible, therefore providing this default value generally prevents false responses or progressions based upon measurement error. To reiterate, however, if the radiologist is able to provide an actual measure, that is generally recorded, even if it is below 5 mm.

When non-nodal lesions 'fragment', the longest diameters of the fragmented portions are generally added together to calculate the target lesion sum. Similarly, as lesions coalesce, a plane between them are generally maintained that would aid in obtaining maximal diameter measurements of each individual lesion. If the lesions have truly coalesced such that they are no longer separable, the vector of the longest diameter in this instance generally is the maximal longest diameter for the 'coalesced lesion'.

While some non-target lesions in some cases are actually measurable, they generally are not measured and instead are generally assessed only qualitatively at the time points specified in the protocol.

Complete Response (CR): Disappearance of all non-target lesions and normalization of tumor marker level. All lymph nodes are non-pathological in size (<10 mm short axis).

Non-CR/Non-PD: Persistence of one or more non-target lesion(s) and/or maintenance of tumor marker level above the normal limits.

Progressive Disease (PD): Unequivocal progression (see comments below) of existing non-target lesions. (Note: the appearance of one or more new lesions is also considered progression).

When the subject also has measurable disease, to achieve 'unequivocal progression' on the basis of the non-target disease, there generally is an overall level of substantial worsening in non-target disease such that, even in presence of SD or PR in target disease, the overall tumor burden has increased sufficiently to merit discontinuation of therapy. A modest 'increase' in the size of one or more non-target lesions is usually not sufficient to quality for unequivocal progression status. The designation of overall progression solely on the basis of change in non-target disease in the face of SD or PR of target disease is generally therefore extremely rare.

A subject having only non-measurable disease arises in some Phase III trials when it is not a criterion of study entry to have measurable disease. The same general concepts apply here as noted above, however, in this instance there is no measurable disease assessment to factor into the interpretation of an increase in non-measurable disease burden. Because worsening in non-target disease is generally not easily quantified (by definition: if all lesions are truly non-measurable) a useful test that can generally be applied when assessing subjects for unequivocal progression is to consider if the increase in overall disease burden based on the change in non-measurable disease is comparable in magnitude to the increase that would be required to declare PD for measurable disease: i.e. an increase in tumor burden representing an additional 73% increase in 'volume' (which is equivalent to a 20% increase diameter in a measurable lesion). Examples include an increase in a pleural effusion from 'trace' to 'large', an increase in lymphangitic disease from localized to widespread, or in some cases are described in protocols as 'sufficient to require a change in therapy'. If 'unequivocal progression' is seen, the subject is generally considered to have had overall PD at that point. While it would be ideal to have objective criteria to apply to non-measurable disease, the very nature of that disease makes it generally very difficult to do so; therefore the increase generally is substantial.

The appearance of new malignant lesions generally denotes disease progression; therefore, some comments on detection of new lesions are generally important. There are generally no specific criteria for the identification of new radiographic lesions; however, the finding of a new lesion generally is unequivocal: i.e., generally not attributable to differences in scanning technique, change in imaging modality or findings thought to represent something other than tumor (for example, some 'new' bone lesions in some cases are simply healing or flare of pre-existing lesions). This is particularly important when the subject's baseline lesions show partial or complete response. For example, necrosis of a liver lesion is frequently reported on a CT scan report as a 'new' cystic lesion, which it generally is not.

A lesion identified on a follow-up study in an anatomical location that was not scanned at baseline is generally considered a new lesion and generally indicates disease progression. An example of this is the subject who has visceral disease at baseline and while on study has a CT or MRI brain ordered which reveals metastases. The subject's brain metastases are generally considered to be evidence of PD even if he/she did not have brain imaging at baseline.

If a new lesion is equivocal, for example because of its small size, continued therapy and follow-up evaluation generally clarifies if it represents truly new disease. If repeat scans confirm there is definitely a new lesion, then progression is generally declared using the date of the initial scan.

While FDG-PET response assessments need additional study, it is sometimes reasonable to incorporate the use of FDG-PET scanning to complement CT scanning in assessment of progression (particularly possible 'new' disease). New lesions on the basis of FDG-PET imaging are generally identified according to the following algorithm:

a. Negative FDG-PET at baseline, with a positive* FDG-PET at follow-up is generally a sign of PD based on a new lesion. * A 'positive' FDG-PET scan lesion generally means one which is FDG avid with an uptake greater than twice that of the surrounding tissue on the attenuation corrected image.
b. No FDG-PET at baseline and a positive FDG-PET at follow-up:
   - If the positive FDG-PET at follow-up corresponds to a new site of disease confirmed by CT, this is generally PD.
   - If the positive FDG-PET at follow-up is not confirmed as a new site of disease on CT, additional follow-up CT scans are generally performed to determine if there is truly progression occurring at that site (if so, the date of PD will be the date of the initial abnormal FDG-PET scan). A 'positive' FDG-PET scan lesion generally means one which is FDG avid with an uptake greater than twice that of the surrounding tissue on the attenuation corrected image.
   - If the positive FDG-PET at follow-up corresponds to a pre-existing site of disease on CT that is not progressing on the basis of the anatomic images, this is generally not PD.

Evaluation of Best Overall Response

The best overall response is generally the best response recorded from the start of the study treatment until the end of treatment. Should a response not be documented until after the end of therapy in this trial, post-treatment assessments generally are considered in the determination of best overall response as long as no alternative anti-cancer therapy has been given. The subject's best overall response assignment generally depends on the findings of both target and non-target disease and generally also takes into consideration the appearance of new lesions.

It is generally assumed that at each protocol-specified time point, a response assessment occurs. Table 6 provides a summary of the overall response status calculation at each time point for subjects who have measurable disease at baseline.

When subjects have non-measurable (therefore non-target) disease only, Table 7 is generally used.

When no imaging/measurement is done at all at a particular time point, the subject is generally not evaluable (NE) at that time point. If only a subset of lesion measurements are made at an assessment, usually the case is generally also considered NE at that time point, unless a convincing argument is made that the contribution of the individual missing lesion(s) does not change the assigned time point response. This would be most likely to happen in the case of PD. For example, if a subject had a baseline sum of 50 mm with three measured lesions and at follow-up only two lesions were assessed, but those gave a sum of 80 mm, the subject has generally achieved PD status, regardless of the contribution of the missing lesion.

The best overall response is generally determined once all the data for the subject is known.

Best response determination in trials where confirmation of complete or partial response is generally not required: Best response in these trials is generally defined as the best response across all time points (for example, a subject who has SD at first assessment, PR at second assessment, and PD on last assessment has a best overall response of PR). When SD is believed to be best response, it in general also meets the protocol specified minimum time from baseline. If the minimum time is not met when SD is otherwise the best time point response, the subject's best response generally depends on the subsequent assessments. For example, a subject who has SD at first assessment, PD at second and does not meet minimum duration for SD, will have a best response of PD. The same subject lost to follow-up after the first SD assessment is generally considered inevaluable.

When nodal disease is included in the sum of target lesions and the nodes decrease to 'normal' size (<10 mm), in some cases they still have a measurement reported on scans. This measurement is generally recorded even though the nodes are normal in order not to overstate progression should it be based on increase in size of the nodes. As noted earlier, this means that subjects with CR in some cases do not have a total sum of 'zero' on the case report form (CRY).

Subjects with a global deterioration of health status requiring discontinuation of treatment without objective evidence of disease progression at that time generally are reported as 'symptomatic deterioration.' Every effort is generally made to document objective progression even after discontinuation of treatment. Symptomatic deterioration is generally not a descriptor of an objective response: it is a reason for stopping study therapy. The objective response status of such subjects is generally determined by evaluation of target and non-target disease as shown in Tables 6 to 7.

Conditions that define 'EP, early death and inevaluability' are study specific and are generally clearly described in each protocol (depending on treatment duration, treatment periodicity).

In some circumstances it is difficult to distinguish residual disease from normal tissue. When the evaluation of complete response depends upon this determination, it is generally recommended that the residual lesion be investigated (fine needle aspirate/biopsy) before assigning a status of complete response. In some cases, FDG-PET is used to upgrade a response to a CR in a manner similar to a biopsy in cases where a residual radiographic abnormality is thought to represent fibrosis or scarring.

For equivocal findings of progression (e.g. very small and uncertain new lesions; cystic changes or necrosis in existing lesions), treatment in some cases continues until the next scheduled assessment. If at the next scheduled assessment, progression is confirmed, the date of progression generally is the earlier date when progression was suspected.

TABLE 6

Time point response: subjects with target (+/−non-target) disease

| Target lesions | Non-target lesions | New lesions | Overall response |
|---|---|---|---|
| CR | CR | No | CR |
| CR | Non-CR/non-PD | No | PR |
| CR | Not evaluated | No | PR |
| PR | Non-PD or not all evaluated | No | PR |

TABLE 6-continued

Time point response: subjects with target (+/−non-target) disease

| Target lesions | Non-target lesions | New lesions | Overall response |
|---|---|---|---|
| SD | Non-PD or not all evaluated | No | SD |
| Not all evaluated | Non-PD | No | NE |
| PD | Any | Yes or No | PD |
| Any | PD | Yes or No | PD |
| Any | Any | Yes | PD |

CR = complete response, PR = partial response, SD = stable disease, PD = progressive disease, and NE = not evaluable.

CR=complete response, PR=partial response, SD=stable disease, PD=progressive disease, and NE=not evaluable.

TABLE 7

Time point response: subjects with non-target disease only

| Non-target lesions | New lesions | Overall response |
|---|---|---|
| CR | No | CR |
| Non-CR/non-PD | No | Non-CR/non-PD(a) NE |
| Not all evaluated | No | PD |
| Unequivocal PD | Yes or No | PD |
| Any | Yes | PD |

CR = complete response, PD = progressive disease, and NE = not evaluable.

(a)'Non-CR/non-PD' is preferred over 'stable disease' for non-target disease since SD is increasingly used as endpoint for assessment of efficacy in some trials so to assign this category when no lesions can be measured is not advised.

Duration of Response

The duration of overall response is generally measured from the time measurement criteria are first met for CR/PR (whichever is first recorded) until the first date that recurrent or progressive disease is recorded on study).

The duration of overall complete response is generally measured from the time measurement criteria are first met for CR until the first date that recurrent disease is objectively documented.

Stable disease is generally measured from the start of the treatment (in randomized trials, from date of randomization) until the criteria for progression are met, taking as reference the smallest sum on study (if the baseline sum is the smallest, this is the reference for calculation of PD).

Example 23: SRA141 CIN Cancers Clinical Trial

Clinical trials are conducted as described above in Example 22 to confirm the efficacy of SRA141 monotherapies in the treatment of patients with cancer with high rates of chromosome instability.

Example 24: Alternative SRA141 Dosing Regimens

Alternative schedules are investigated once sufficient clinical safety and tolerability, PK and activity biomarker data become available. Consideration in some cases is given to alternative dosing schedules at any time during the trial, following discussion between the sponsor and investigators. The need for an alternative schedule in some cases is indicated by the emerging safety and tolerability data, PK and/or PDn data. Alternative schedules in some cases includes, but are not limited to, the following examples: 7 days on/7 days off, 14 days on/14 days off, twice daily dosing, or other variations. Alternative dosing schedule cohorts in some cases commence in parallel to or instead of the continuous schedule cohorts.

The initial starting dose for an alternative dosing schedule will depend on the safety, tolerability and PK results from the previous cohorts. If an alternative schedule is to be tested after an MTD has been identified with a previous schedule, the starting total weekly dose for the new schedule will not exceed the total weekly dose at the MTD for the previous schedule. If an MTD has not been identified with the previous schedule, a dose escalation step in some cases occurs; however, the dose escalation generally does not exceed 50% based on the total weekly dose.

Example 25: Immunohistochemistry Assessment of SRA141 Treatment in Rat MV-4-11 Xenograft Model of Biphenotypic B Myelomonocytic Leukemia Rats bearing subcutaneous biphenotypic B myelomonocytic leukemia MV-4-11 tumors were treated with SRA141 at 75 mg/kg or vehicle, BID, or with SRA141 at 100 mg/kg, QD, for 5 days. Tumors were collected from the animals 12 hours after administration of the last dose. Formalin fixed paraffin-embedded tumor and/or skin were assessed by immunohistochemistry for total MCM2, phosphorylated MCM2 at Serine 40 (pMCM2-S40) and phosphorylated MCM2 at Serine 53 (pMCM2-S53), phosphorylated MCM2 at Serine 41 (pMCM2-S41), and phosphorylated-Histone H2A.X at Serine 139 effects at steady-state.

Figure 24A:
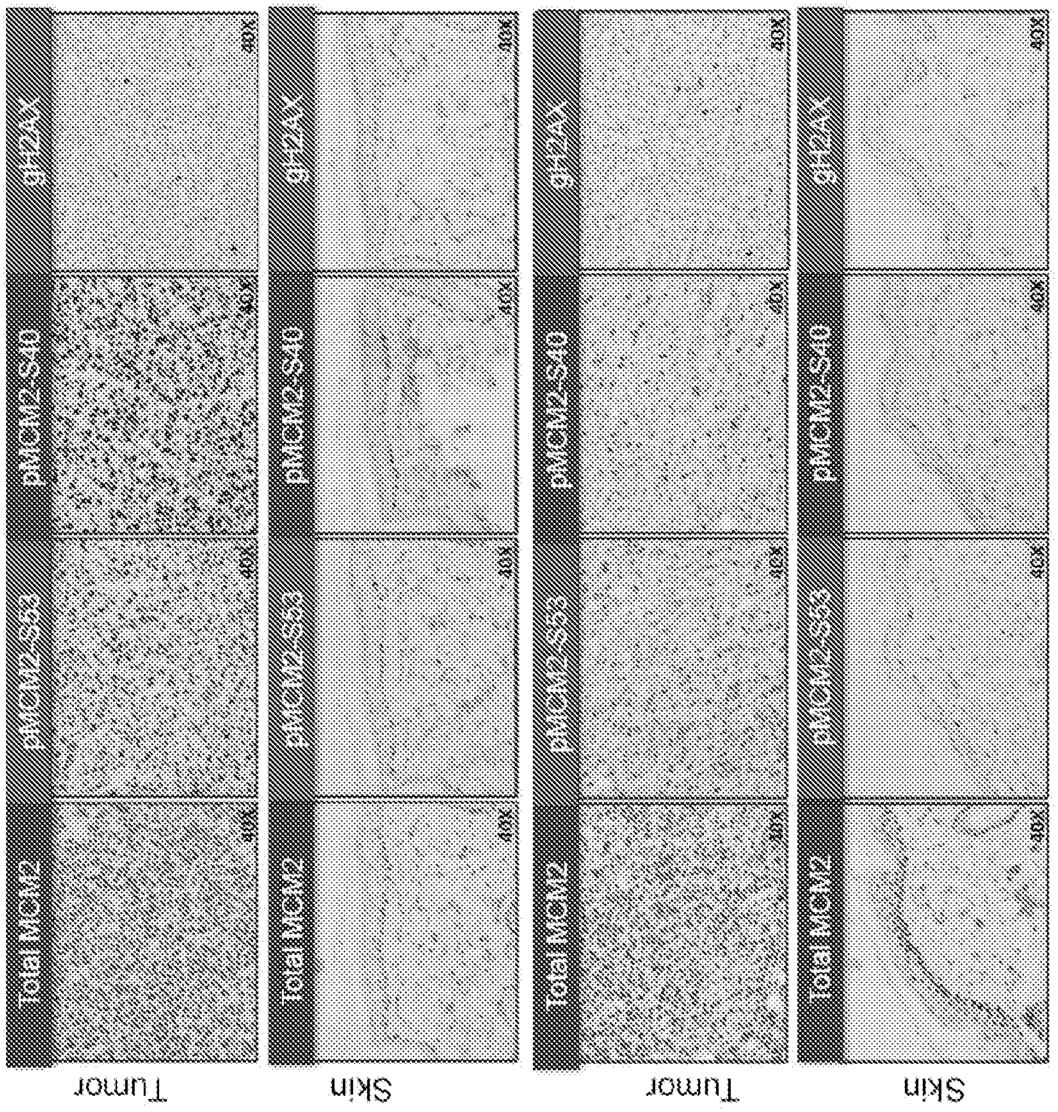
FIG. 24A shows immunohistochemistry assessments of total MCM2, phosphorylated MCM2, and gH2AX in tumor and surrogate tissue from a rat xenograft model of leukemia treated with and without SRA141.
Figure 24B:
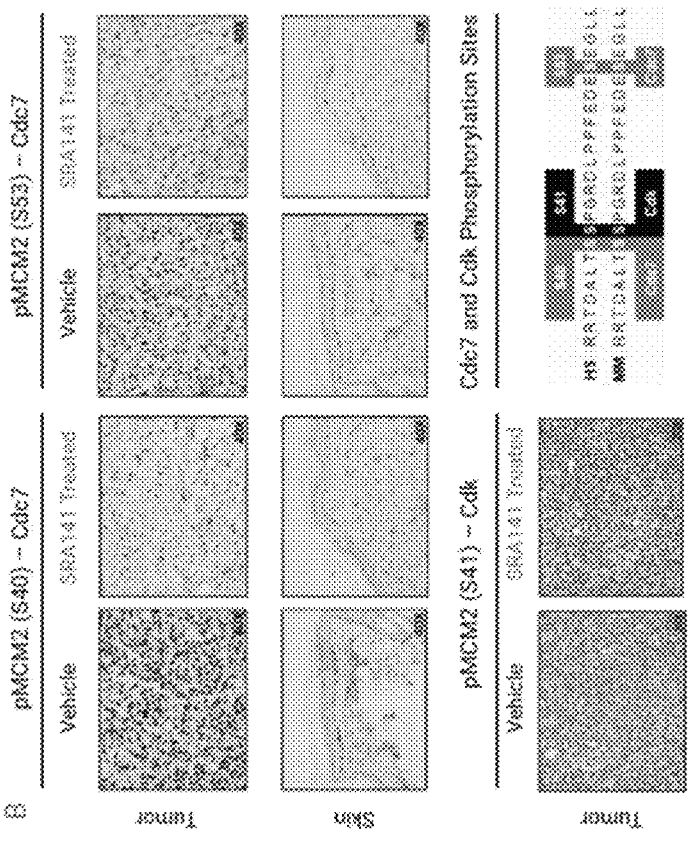
FIG. 24B shows immunohistochemistry assessments of phosphorylated MCM2 in tumor and surrogate tissue from a rat xenograft model of leukemia. The amino acid sequences of HS and MM are the same and correspond to SEQ ID NO:1.
Figure 24C:
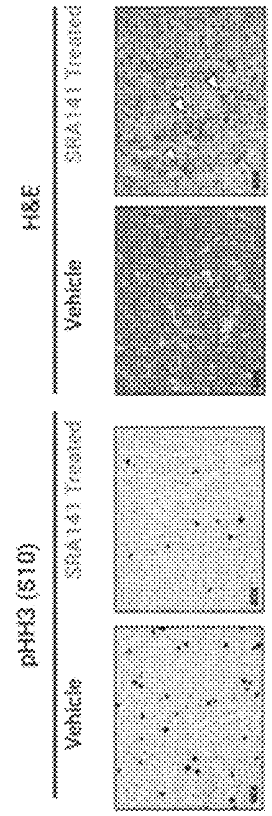
FIG. 24C shows immunohistochemistry and H&E assessments of tumor from a rat xenograft model of leukemia treated with SRA141 and vehicle.

As shown in FIG. 24A and FIG. 24B, substantial decreases in pMCM2 at S40 and S53 in tumor correlated with changes in skin tissue, suggesting skin biopsies may be utilized to demonstrate on-target activity of SRA141. As expected, no effects of pMCM2-S41 were seen following SRA141 treatment, as S41 is phosphorylated by Cdk, not Cdc7. The data thus further demonstrates that SRA141 has specificity for Cdc7 inhibition. Tumors were also analyzed by immunohistochemistry for pHH3, a marker of mitotic cells, or stained with hematoxylin and eosin (H&E). Results shown in FIG. 24C demonstrate that after 5 days of dosing, tumors treated with SRA141 resulted in fewer mitotic cells and an increased presence of apoptotic cells (see white arrowheads in FIG. 24C) compared to vehicle, suggesting the presence of anti-tumor activity in the SRA141-treated MV-4-11 tumors.

Evaluation of Xenograft Tumor

Tumor cells in xenograft tumors (but not stroma or surrounding rat tissue) were scored. Scoring is performed semi-quantitatively with the main components to scoring tumor cells for total MCM2, pMCM2-S53, pMCM2-S40, and gH2AX reactivity as percentages at differential intensities and H-Scores. Percentage and intensity measures are estimated by a scientist in the same relative region of tumor (one 40×-field from the bottom edge) within each xenograft sample.

The H-Score approach used to evaluate the xenograft tissues requires recording the percentage of tumor cells with nuclear staining at a corresponding differential intensity on a four-point semi-quantitative scale (0, 1+, 2+, 3+). On this scale: 0=null, negative or non-specific staining, 1+=low or weak staining, 2+=medium or moderate staining, and 3+=high or strong staining.

The H-Score is calculated by summing the percentage of cells with intensity of expression (brown staining) multiplied by their corresponding differential intensity on a four-point semi-quantitative scale (0, 1+, 2+, 3+). Thus, scores range from 0 to 300.

$$H\text{-Score}=[(\% \text{ at } <1)\times 0]+[(\% \text{ at } 1+)\times 1]+[(\% \text{ at } 2+)\times 2]+[(\% \text{ at } 3+)\times 3]$$

Evaluation of Rat Skin

Epithelial cells of the epidermis in rat skin samples were scored jointly by two scientists. Scoring was performed quantitatively with the main component to scoring epidermal cells for total MCM2, pMCM2-S53, pMCM2-S40, and gH2AX reactivity as counts of positive cells. For each skin sample, four evenly distributed regions were marked for review. The regions were aligned to the same approximate position in each skin sample. For pMCM2-S53 and pMCM2-S40, the number of positive cells in a 10× field at the four representative regions was counted. For gH2Ax, the number of positive cells in a 20× field at the four representative regions was counted. Cells were counted if staining was readily observed at 10× or 20×, regardless of intensity. Cells were only counted within the flat epidermis and not in regions of invagination in order to consistently capture the same total area.

The number of positive skin cells counted across the regions analyzed for each skin sample were averaged for each biomarker. The average number of positive skin cells for pMCM2-S53 and pMCM2-S40 were then represented as a percentage relative to the average number of positive skin cells for total MCM2. The average number of positive skin cells for gH2AX was multiplied by 2 to account for its assessment at 20× versus 10× (normalized) and was then also represented as a percentage relative to the average for total MCM2.

Skin cell counts were performed by recording the number of positive cells (at any intensity) counted by two independent scientists in multiple regions of skin (two regions for total MCM2, four regions for pMCM2 and gH2AX) that are in the same approximate location for each sample. The number of positive cells recorded at each skin region for each biomarker were averaged for each sample. The average cell counts for pMCM2-S53, pMCM2-540, and gH2AX (normalized for magnification) were compared as percentages of total MCM2. Cell counts were performed at 20× for gH2AX and 10× for all other markers.

Avg. Count (pMCM2,gH2AX)=[region 1 pos cells]+[region 2 pos cells]+[region 3 pos cells]+[region 4 pos cells]/4

Avg. Count (total MCM2)=[region 1 pos cells]+[region 4 pos cells]/2

Percentage of Total (pMCM2)=[average count pMCM2]/[average count total MCM2]×100

Percentage of Total (gH2AX)=[average count gH2AX×2 (normalized)]/[average count total MCM2]×100

Figure 25B:
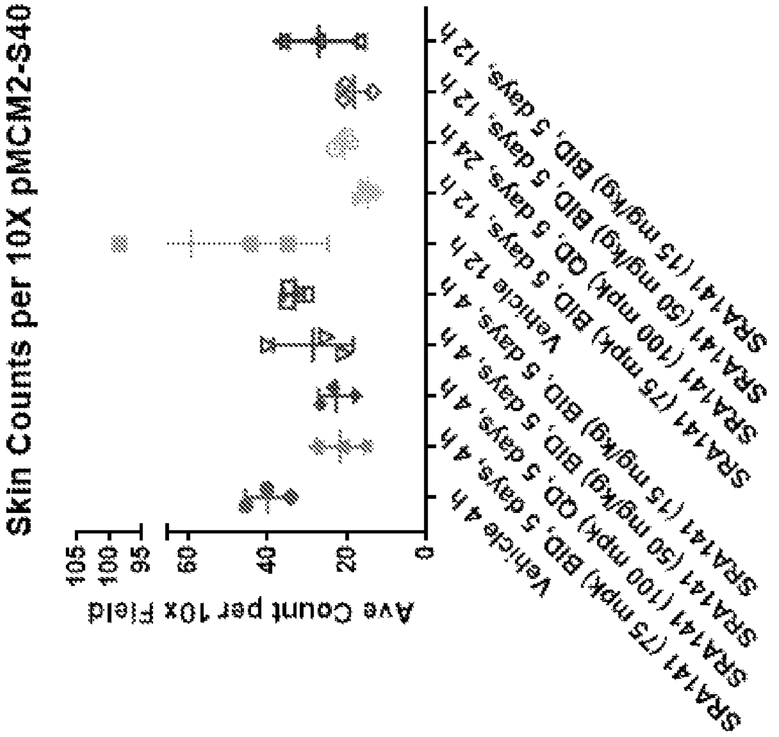
FIG. 25B shows results of evaluation of pMCM2-S40 expression in skin samples from rat xenografts following treatment with SRA141 at various dosages.
Figure 25A:
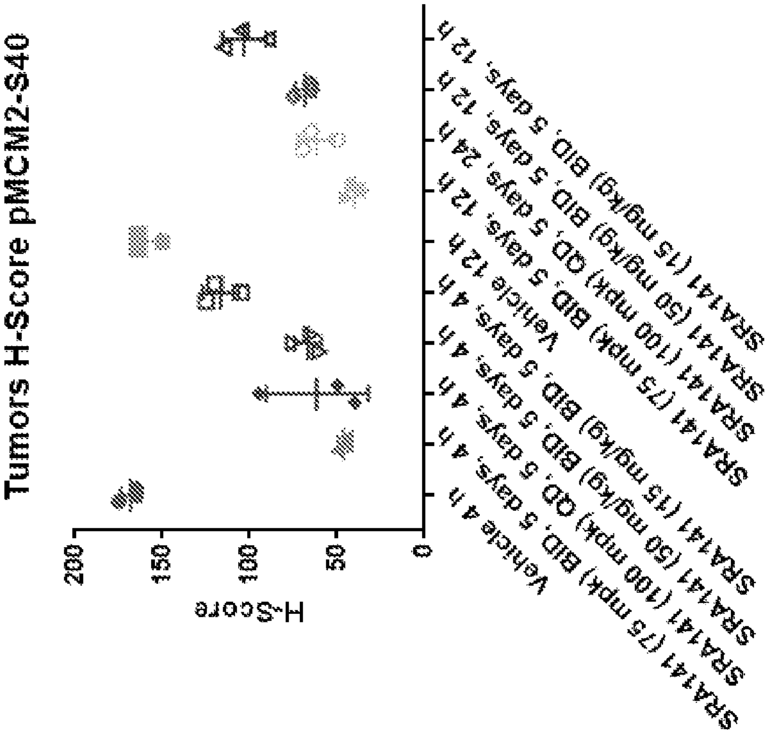
FIG. 25A shows results of evaluation of pMCM2-S40 expression in xenograft tumors following treatment with SRA141 at various dosages.

Results shown in FIG. 25A and FIG. 25B demonstrate a dose-dependent decrease in pMCM2-S40 in both tumor and skin in the rat MV-4-11 xenograft model.

Example 26: Immunohistochemistry Assessment of Human Tumor and Skin

Formalin fixed paraffin-embedded human tumor and human normal skin samples were assessed by immunohistochemistry for total MCM2, pMCM2-S53, pMCM2-S40, and gH2AX.

Evaluation of Human Tumor

Tumor cells in human metastatic colon cancer samples (but not stroma or surrounding non-neoplastic tissue components) were scored. H-Scores were calculated as previously described (Example 25).

Evaluation of Human Skin

Epithelial cells of the epidermis in human skin samples were scored jointly by two scientists. Scoring was performed quantitatively with the main component to scoring epidermal cells for total MCM2, pMCM2-S53, pMCM2-S40, and gH2AX reactivity as counts of positive cells. For each skin sample, two evenly distributed regions were marked for review. The regions were aligned to the same approximate position in each skin sample and assessed at 10× for MCM2, and pMCM2. For gH2AX, the number of positive cells in a 20× filed at the two regions was counted. Cells were counted if staining was readily observed at 10× or 20×, regardless of intensity. Cells were only counted within the flat epidermis and not in regions of invagination in order to consistently capture the same total area.

The number of positive skin cells counted across the regions analyzed for each skin sample were averaged for each biomarker. The average number of positive skin cells for pMCM2-S53 and pMCM2-S40 were then represented as a percentage relative to the average number of positive skin cells for total MCM2. The average number of positive skin cells for gH2AX was multiplied by 2 to account for its assessment at 20× versus 10× (normalized) and was then also represented as a percentage relative to the average for total MCM2.

Skin cell counts were performed as described in Example 25.

Avg. Count (total MCM2, pMCM2, gH2AX)=[region 1 pos cells]+[region 2 pos cells]/2

Percentage of Total (pMCM2)=[average count pMCM2]/[average count total MCM2]×100

Percentage of Total (gH2AX)=[average count gH2AX×2 (normalized)]/[average count total MCM2]×100

Figure 26:
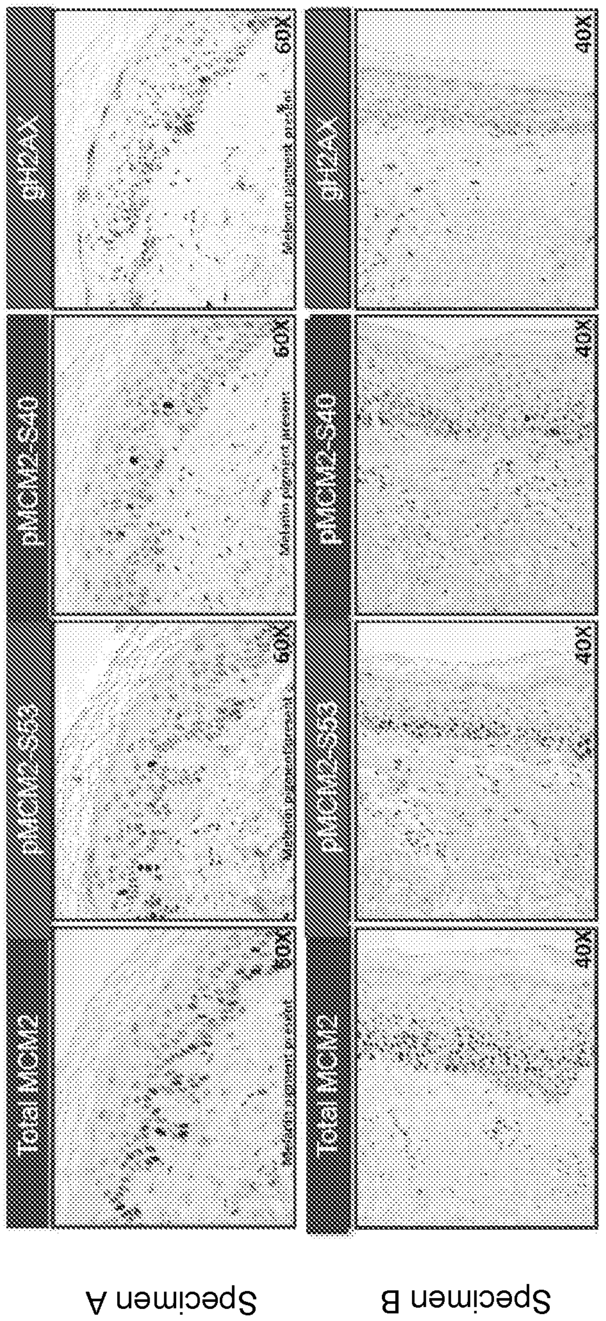
FIG. 26 shows results of evaluation of total MCM2, pMCM2-S53, pMCM2-S40, and gH2AX in normal human skin.

Immunohistochemistry assessment of normal human tissue demonstrates that baseline levels of pMCM-S40 are measurable and at comparable levels to rat skin samples following treatment with vehicle (FIG. 26). Human skin thus appears to be a reasonable surrogate tissue to assess SRA141 on-target pharmacodynamics.

Example 27: SRA141 Combination with Additional Anti-Neoplastic Agents in Various Cancer Cell Lines Combination activity of SRA141 with nine targeted anti-neoplastic agents was assessed in solid tumor cell lines (Colo-205, SW620, A375 (V600E melanoma)), as well as hematologic cancer cell lines (KG-1, MOLM-13, MV411). Cell viability was evaluated using the CTG and CTBlue assays previously described (Example 3). Assays were performed in 96 well plates using Staurosporine as an internal control. Cells were incubated with a single agent (Phase I) or combination of SRA141 and a second agent (Phase II) for 72 hours.

In Phase I, the 20% inhibition concentration (IC20) and 50% inhibition concentration (IC50) were determined for each of the following nine agents in all six cell lines: ABT-199, the ATM kinase inhibitor KU-60019, the Aurora B kinase inhibitor Barasertib, the MEK inhibitor Trametinib, the PI3K pathway inhibitor Copanlisib, the Retinoid pathway inhibitors Bexarotene and Tretinoin, the Threonine Tyrosine Kinase (TTK) inhibitor CFI-402257, and the epidermal growth factor inhibitor Erlotinib.

In Phase II, assays were repeated in the presence of each agent at a fixed concentration (IC20 and IC50 for each agent) and SRA141 in combination, where the assay was performed over a range of concentrations of SRA141. Combination Index (CI) values were calculated using the Bliss Independence model (see, e.g., Foucquier and Guedj, *Pharmacol. Res. Perspect.* 2015 3(3), herein incorporated by reference in its entirety). CI values less than 1 (CI<1) indicate that the combination effect is greater than expected additive effect.

Figure 27A:
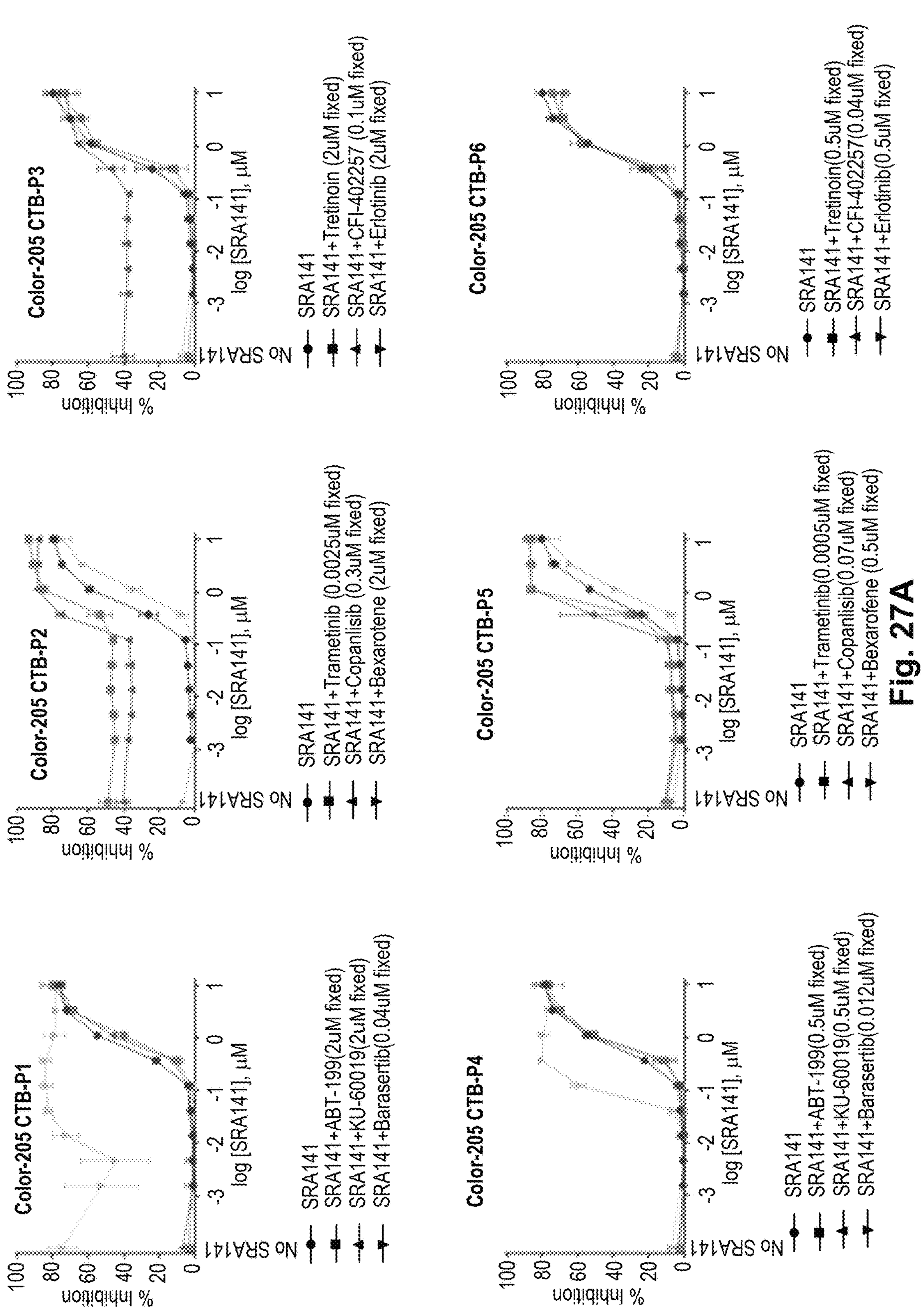
FIG. 27 shows results of cell viability assays performed with SRA141 in combination with various additional anti-neoplastic agents in Colo-205 cells (FIG. 27A, FIG. 27G), SW620 cells (FIG. 27B), A375 cells (FIG. 27C), KG-1 cells (FIG. 27D), MOLM-13 cells (FIG. 27E, FIG. 27H), and MV411 cells (FIG. 27F).
Figure 27B:
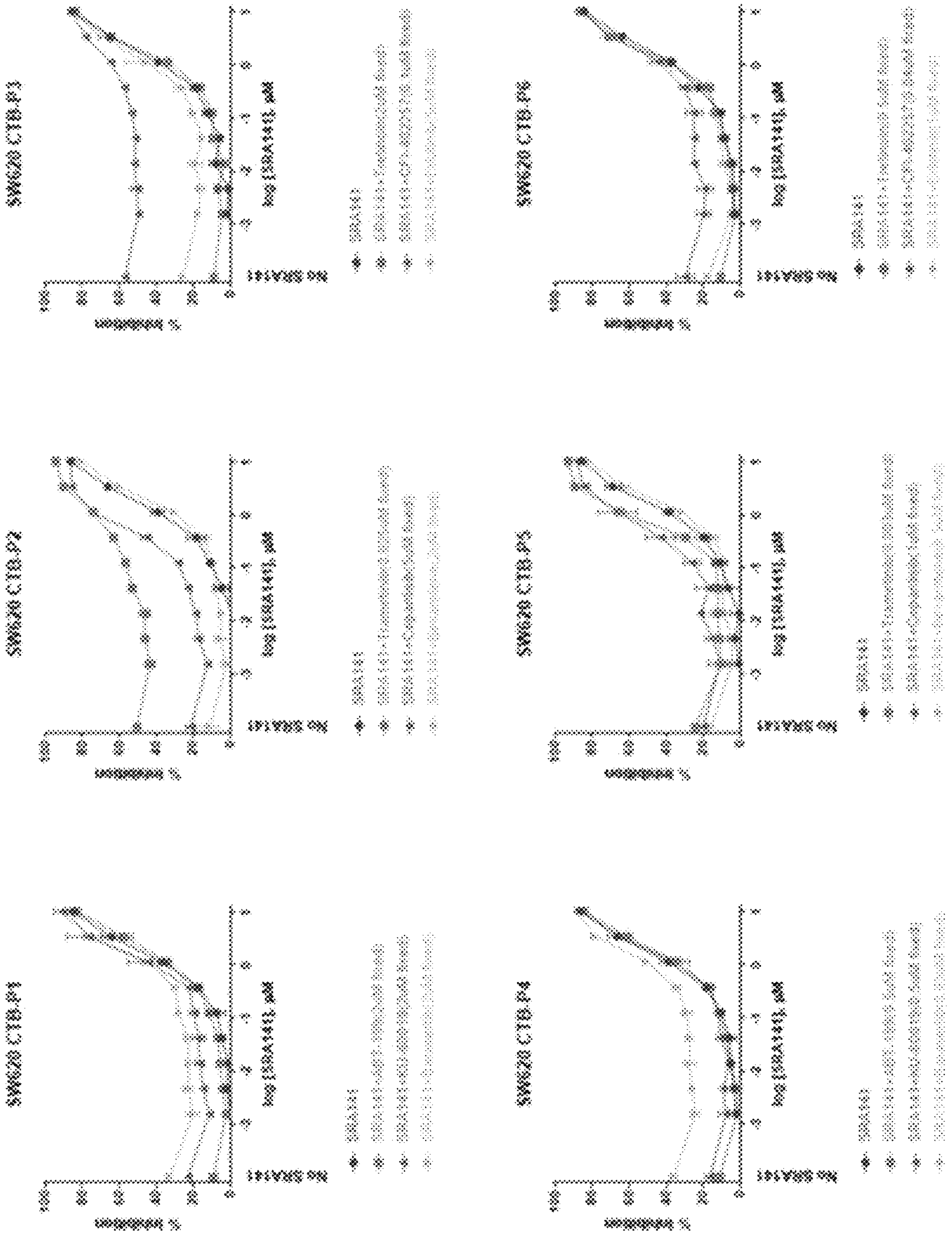
Figure 27C:
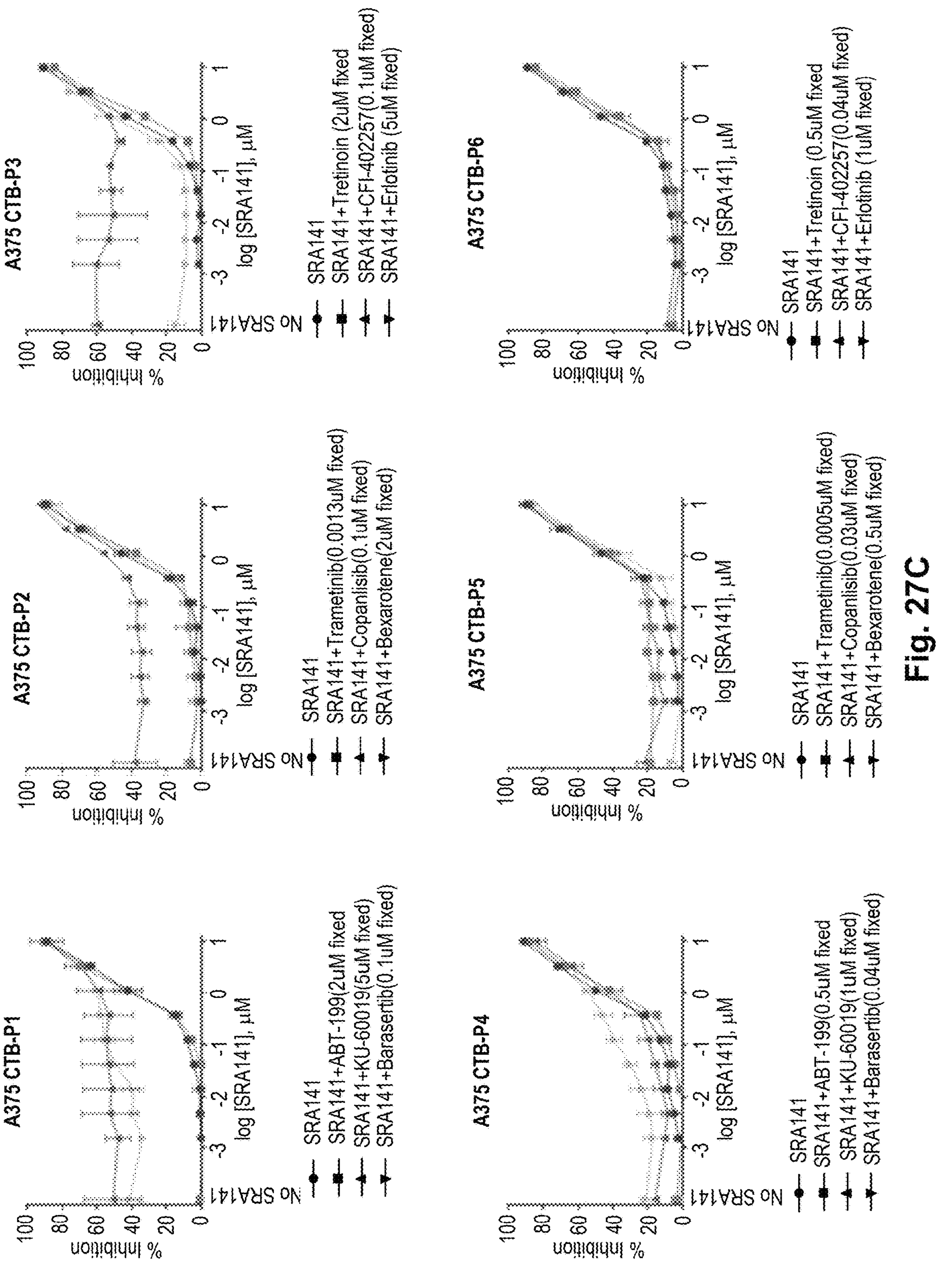
Figure 27D:
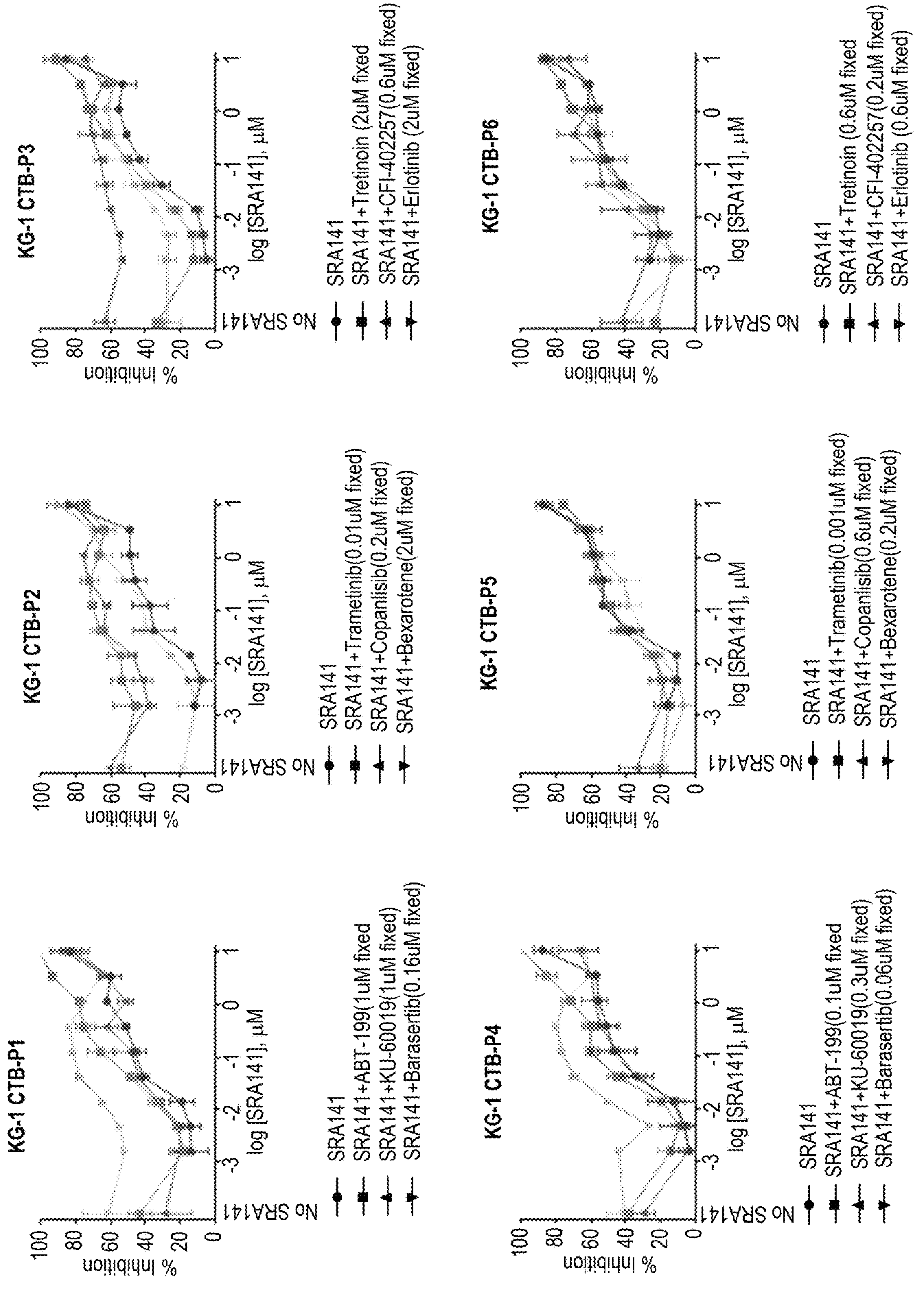
Figure 27E:
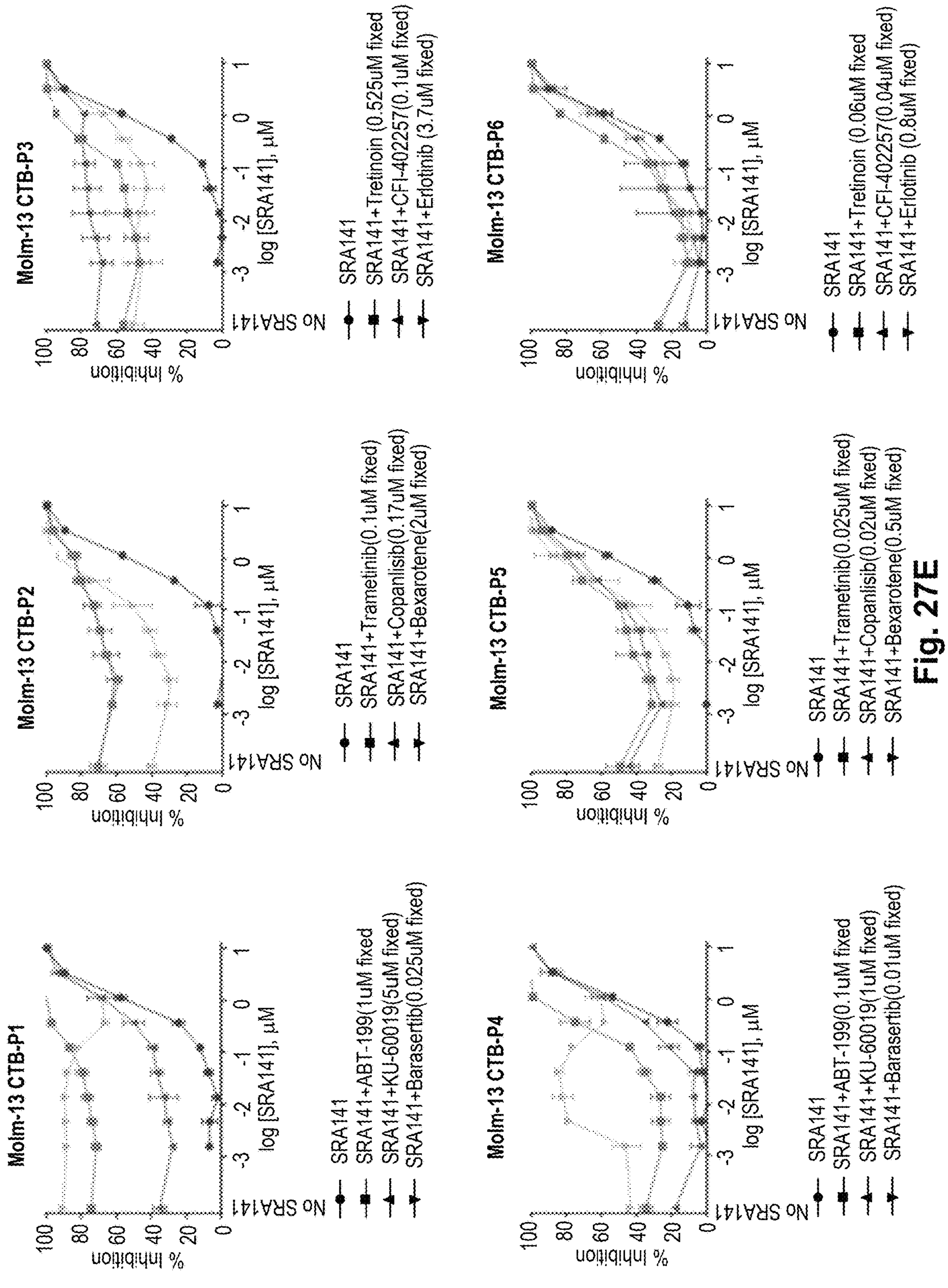
Figure 27F:
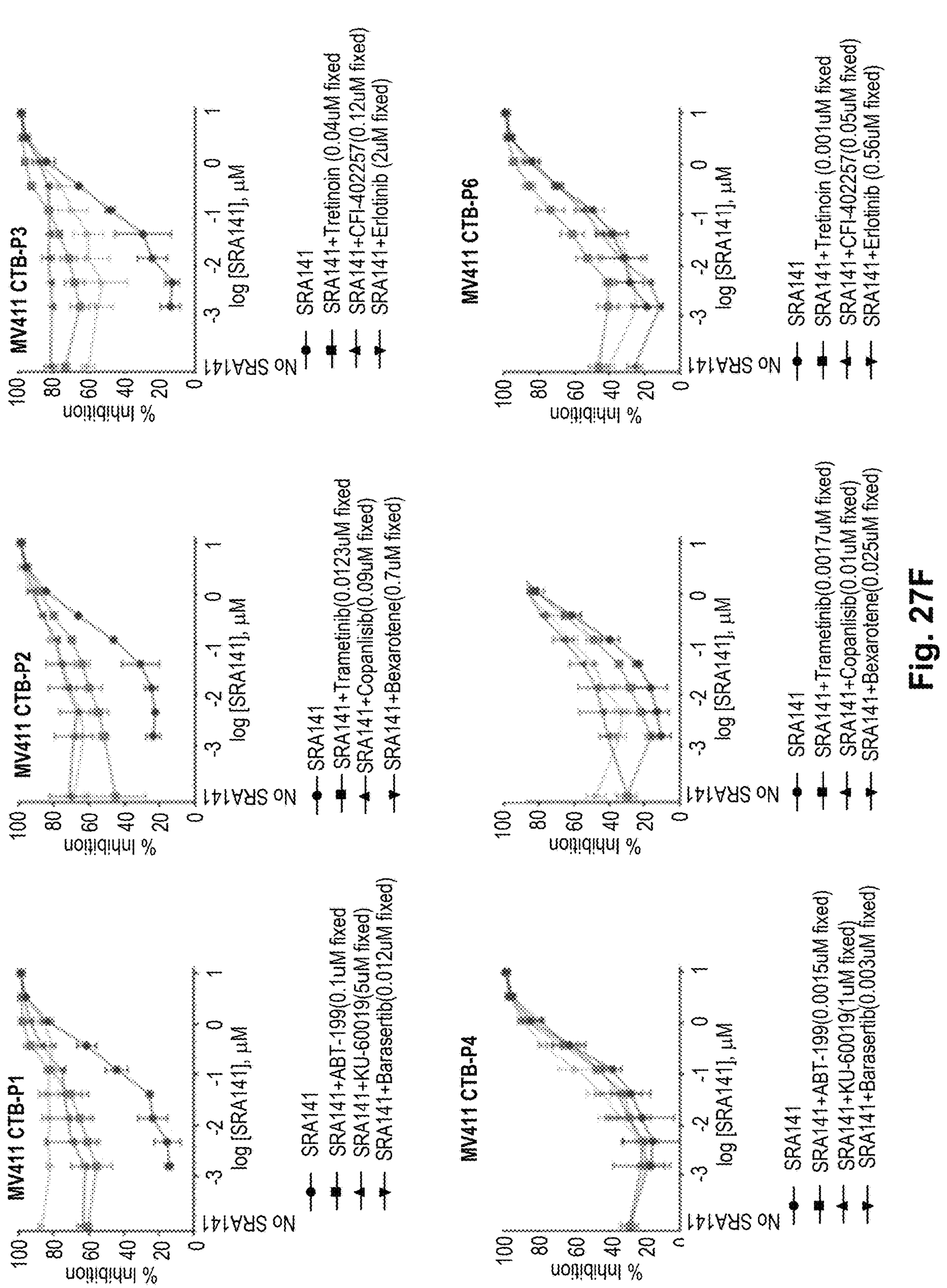
Figure 27H:
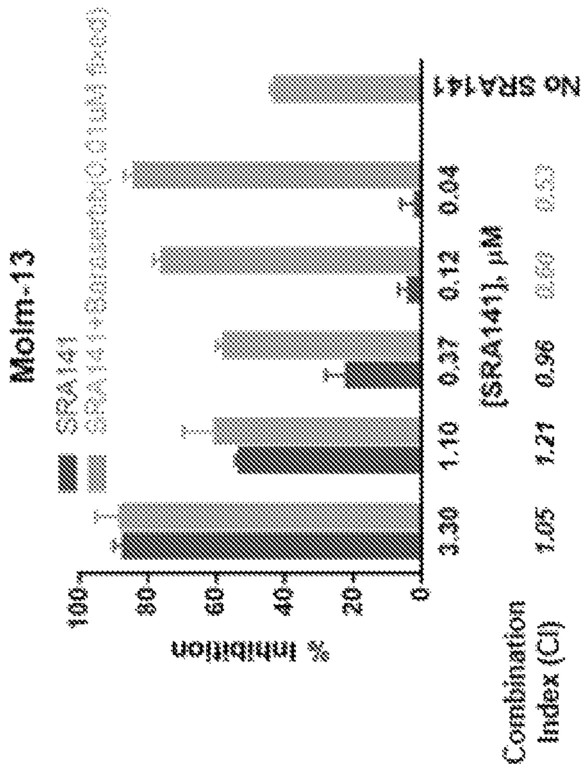
Figure 27G:
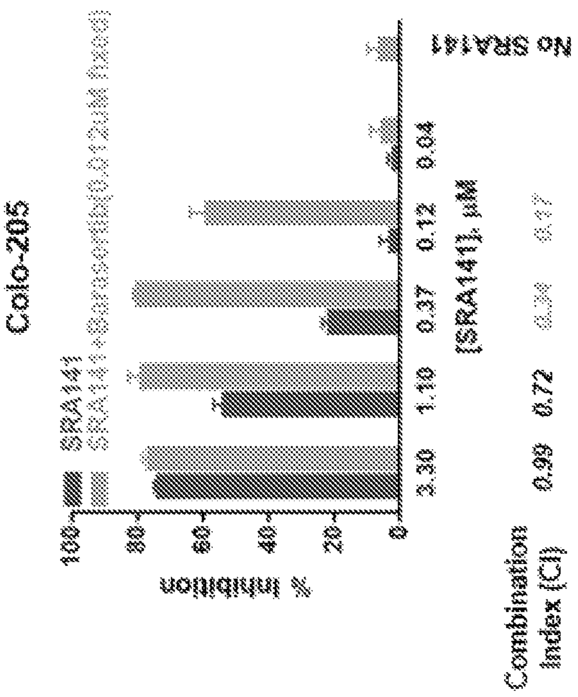

Results of combination treatments in Colo-205 cells (FIG. 27A and FIG. 27G) demonstrate that SRA141 and Barasertib act synergistically, particularly in the presence of 0.012 μM Barasertib. In contrast, the combination of SRA141 and Bexarotene appear to have an antagonistic effect. Trametinib and Copanlisib appear to have a slight additive effect with SRA141 in Colo-205 cells.

Results of combination treatments in SW620 cells (FIG. 27B) show that Barasertib, Trametinib, and Copanlisib all have slight additive effects on SRA141. Results of combination treatments in A375 (FIG. 27C) and KG-1 (FIG. 27D) cells show that Barasertib, but not Trametinib or Copanlisib have slight additive effects with SRA141.

Results of combination treatments in MOLM-13 cells (FIG. 27E) demonstrate that ABT-199 and SRA141 act synergistically, particularly in the presence of 0.1 μM ABT-199. In addition, Barasertib (FIG. 27H), Trametinib, Copanlisib, Bexarotene, and Tretinoin all demonstrate slight additive effects with SRA141 in MOLM-13 cells.

Results of combination treatments in MV411 cells (FIG. 27F) show that Barasertib, Copanlisib and Tretinoin all have slight additive effects with SRA141.

Example 28: SRA141 Synergizes with Inhibition of Anti-Apoptotic Genes

Figure 28B:
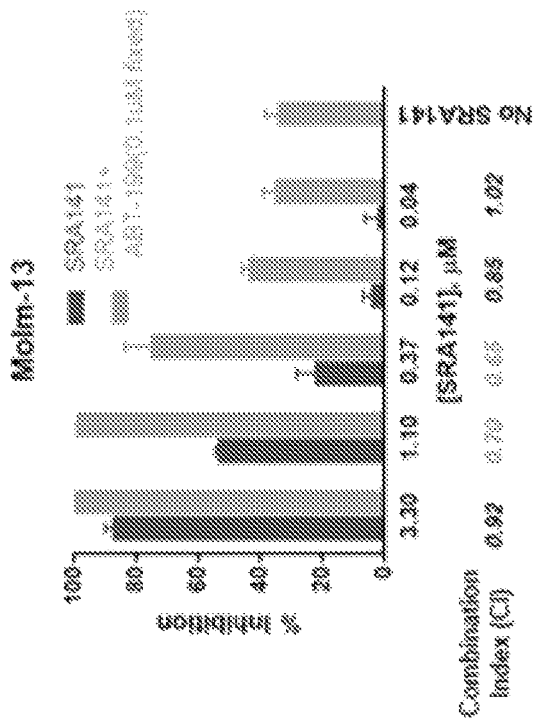
FIG. 28 shows results of treatment with SRA141 in cells following inhibition of anti-apoptotic genes by RNAi knockdown (FIG. 28A) or treatment with ABT-199 (FIG. 28B).
Figure 28A:
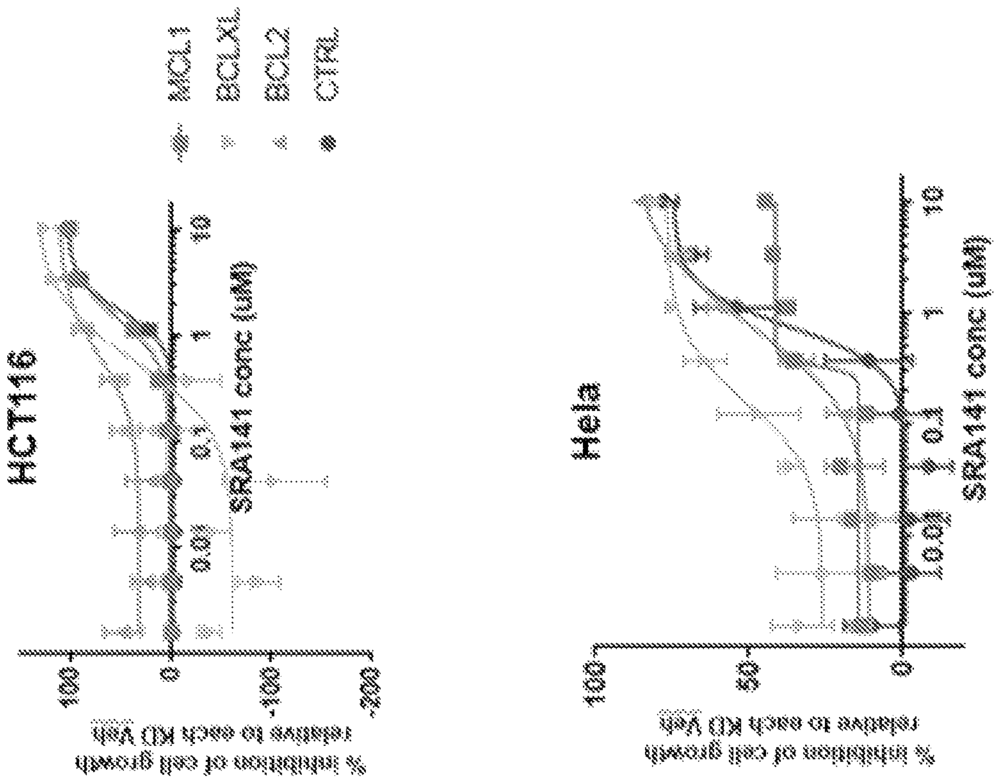

Anti-apoptotic genes BCL-XL, BCL-2, and MCL-1 were inhibited in HCT116 and Hela cells using RNAi knockdown. Cells were plated in 96-well plates at 2000 cells/well and were transfected with an RNAi/Lipofectamine RNAimax solution at a final concentration of 10 nM. Transfected cells were treated with SRA141 at a range of doses for 72 hours. Cell viability of treated cells transfected with RNAi against CTRL (non-toxic control RNAi), BCL-2, BCL-XL, or MCL-1 was measured using CTBlue assays as previously described (Example 3). Data shown in FIG. 28A demonstrate that anti-apoptotic genes inhibited by RNAi synergize with SRA141.

The anti-apoptotic gene BCL-2 was inhibited in Molm-13 cells by treatment with 0.1 μM ABT-199 as previously described (see Examples 6 and 24). Cells were treated with 0.1 μM ABT-199 and SRA141 for 72 hours at SRA141 concentrations of 0.04 μM to 3.30 μM. Synergy with BCL-2 inhibition and SRA141 was demonstrated at the following concentrations of SRA141: 0.12 μM, 0.37 μM, 1.10 μM and 3.30 μM (FIG. 28B) as indicated by Combination Index values less than 1 (see Example 24)

Example 29: Clinical Trial Evaluation of Cdc7 Inhibitor

To further confirm the efficacy of a Cdc7 inhibitor for the treatment of cancer in human patients, a clinical trial is performed. Suitable patients include patients diagnosed with cancer (e.g., breast cancer, colon cancer, lung cancer; blood cancers such as leukemia, lymphoma, myeloma, acute myeloid leukemia (AML) and chronic myelogenous leukemia (CML), melanoma, uterine cancer, thyroid cancer, chronic eosinophilic leukemia, diffuse large B-cell lymphoma (DLBCL), bladder cancer, cervical cancer, colorectal cancer (CRC), gastric cancer, endometrial cancer, hepatocellular cancer, non-small cell lung cancer, ovarian cancer, prostate cancer, pancreatic cancer, brain cancer, sarcoma, small cell lung cancer, neuroblastoma and head and neck cancer). Patients are orally administered the Cdc7 inhibitor, SRA-141. The maximum effective dosage is confirmed starting with optimal dosages converted from animal studies described above. Determination of human equivalent dosages from animal (i.e., rat and/or mouse) studies is performed using techniques known to those of ordinary skill in the art (Nair, A. and Jacob, S. J. Basic Clin. Pharm; March 2016 7(2): 27-31). Dosages of SRA-141 can be 100-5,000 mg; 100-1,000 mg; 1,000-2,000 mg; 2,000-3,000 mg; 3,000-4,000 mg; 4,000-5,000 mg; 1,500-2,500 mg; 500-1,000 mg; 1,000-1,500 mg; 1,500-2,000 mg; 2,000 mg-2,500 mg; 2,500-3,000 mg; 3,000-3,500 mg; 3,500-4,000 mg; 4,000-4,500 mg or 4,500-5,000 mg. SRA-141 can be administered daily, twice daily, thrice daily, every other day, weekly, monthly, daily dosing for 1-7 days followed by 1-28 days of non-dosing, 1-28 days of daily dosing followed by 1-28 days of non-dosing. Patients are monitored for disease progression.

Example 30: Clinical Trial Evaluation of Cdc7 Inhibitor in Combination with Additional Anti-Neoplastic Agent(s)

To further confirm the efficacy of a Cdc7 inhibitor in combination with an inhibitor of the mTOR pathway, an inhibitor of DNA polymerase, and inhibitor of receptor tyrosine kinases, and inhibitor of the MAPK pathway, a regulator of the retinoid pathway, a regulator of apoptosis, or a PARP inhibitor in human patients, a clinical trial is performed. Suitable patients include patients diagnosed with cancer (e.g., breast cancer, colon cancer, lung cancer; blood cancers such as leukemia, lymphoma, myeloma, acute myeloid leukemia (AML) and chronic myelogenous leukemia (CML), melanoma, uterine cancer, thyroid cancer, chronic eosinophilic leukemia, diffuse large B-cell lymphoma (DLBCL), bladder cancer, cervical cancer, colorectal cancer (CRC), gastric cancer, endometrial cancer, hepatocellular cancer, non-small cell lung cancer, ovarian cancer, prostate cancer, pancreatic cancer, brain cancer, sarcoma, small cell lung cancer, neuroblastoma and head and neck cancer). Patients are orally administered the Cdc7 inhibitor, SRA-141. Patients are concurrently administered an inhibitor of the mTOR pathway, an inhibitor of DNA polymerase, and inhibitor of receptor tyrosine kinases, and inhibitor of the MAPK pathway, a regulator of the retinoid pathway, a regulator of apoptosis, a PARP inhibitor, or an antifolate antimetabolite in human patients. Maximum effective dosages to be administered are determined using techniques that are known to those of ordinary skill of the art. Patients are monitored for disease progression.

REFERENCES CITED

T. E. Creighton, *Proteins: Structures and Molecular Properties* (W.H. Freeman and Company, 1993)

A. L. Lehninger, *Biochemistry* (Worth Publishers, Inc., current addition)

Sambrook, et al., *Molecular Cloning: A Laboratory Manual* (2nd Edition, 1989)

*Methods In Enzymology* (S. Colowick and N. Kaplan eds., Academic Press, Inc.)

*Remington's Pharmaceutical Sciences,* 18th Edition (Easton, Pennsylvania: Mack Publishing Company, 1990)

Carey and Sundberg *Advanced Organic Chemistry* $3^{rd}$ *Ed.* (Plenum Press) Vols A and B (1992)

U.S. Pat. No. 5,145,684

U.S. Pat. No. 4,107,288

Monga S P, Wadleigh R, Sharma A, et al. Intratumoral therapy of cisplatin/epinephrine injectable gel for palliation in patients with obstructive esophageal cancer. Am. J. Clin. Oncol. 2000; 23(4):386-392

Mary M. Tomayko C., Patrick Reynolds, 1989. Determination of subcutaneous tumor size in athymic (nude) mice. Cancer Chemotherapy and Pharmacology, Volume 24, Issue 3, pp 148-154

E Richtig, G Langmann, K Müllner, G Richtig and J Smolle, 2004. Calculated tumour volume as a prognostic parameter for survival in choroidal melanomas. Eye (2004) 18, 619-623

Jensen et al. BMC Medical Imaging 2008. 8:16

Tomayko et al. Cancer Chemotherapy and Pharmacology September 1989, Volume 24, Issue 3, pp 148-154

Faustino-Rocha et al. Lab Anim (NY). 2013 June; 42(6): 217-24

Bonte D, Lindvall C, Liu H, et al. Cdc7-Dbf4 kinase overexpression in multiple cancers and tumor cell lines is correlated with p53 inactivation. Neoplasia. 2008; September; 10(9):920-31.

Cadigan K M. Wnt signaling: complexity at the surface. J Cell Sci [Internet]. 2006; 119(3):395-402. Available from: http://jcs.biologists.org/cgi/doi/10.1242/jcs.02826

Cheng A N, Jiang S S, Fan C C, et al. Increased Cdc7 expression is a marker of oral squamous cell carcinoma and overexpression of Cdc7 contributes to the resistance to DNA-damaging agents. Cancer Lett [Internet]. 2013; 337(2):218-25. Available from: http://dx.doi.org/10.1016/j.canlet.2013.05.008

Cremolini C, Schirripa M, Antoniotti C, et al. First-line chemotherapy for mCRC-a review and evidence-based algorithm. Nat Rev Clin Oncol [Internet]. 2015; 12(10): 607-19. Available from: http://dx.doi.org/10.1038/nrclinonc.2015.129

Dienstmann R, Vermeulen L, Guinney J, et al. Consensus molecular subtypes and the evolution of precision medicine in colorectal cancer. Nat Rev Cancer [Internet]. 2017 [cited 2017 Mar. 3]; 17. Available from: http://www.nature.com.proxy.lib.umich.edu/nrc/journal/v17/n2/pdf/nrc.2016.126.pdf Ferlay J, Soerjomataram I, Ervik M, Dikshit R, Eser S, Mathers C, Rebelo M, Parkin D M, Forman D, Bray, F. GLOBOCAN 2012 v1.0, Cancer Incidence and Mortality Worldwide: IARC CancerBase No. 11 [Internet]. Lyon, France: International Agency for Research on Cancer; 2013. Available from: http://globocan.iarc.fr, accessed on 14 May 2018.

Fodde R, Kuipers J, Rosenberg C, et al. Mutations in the APC tumour suppressor gene cause chromosomal instability. Nat Cell Biol [Internet]. 2001; 3(4):433-8. Available from: http://eutils.ncbi.nlm.nih.gov/entrez/eutils/elink.fcgi?dbfrom=pubmed&id=11283620&ret mode=ref&cmd=prlinks%5Cnpapers2://publication/doi/10.1038/35070129

Gregory G P, Hogg S J, Kats L M, et al. CDK9 inhibition by dinaciclib potently suppresses Mcl-1 to induce durable apoptotic responses in aggressive MYC-driven B-cell lymphoma in vivo. Leukemia. 2015; 29:1437-1441.

Guinney J, Dienstmann R, Wang X, et al. The consensus molecular subtypes of colorectal cancer. Nat Med [Internet]. 2016 Oct. 12 [cited 2017 Mar. 17]; 21(11):1350-6. Available from: http://www.nature.com/doifinder/10.1038/nm.3967

Hailey J R, Nold J B, Brown R H, et al. Biliary Proliferation Lesions in the Sprague-Dawley Rat Adverse/Non-adverse. Toxicologic Pathology. 2013; 42(5):844-854

Hou Y, Wang H-Q, Ba Y. High expression of cell division cycle 7 protein correlates with poor prognosis in patients with diffuse large B-cell lymphoma. Med Oncol [Internet]. 2012; 29(5):3498-503. Available from: http://link.springer.com/10.1007/s12032-012-0223-y Howlader N, Noone A M, Krapcho M, Miller D, Bishop K, Kosary C L, Yu M, Ruhl J, Tatalovich Z, Mariotto A, Lewis D R, Chen H S, Feuer E J, Cronin K A (eds). SEER Cancer Statistics Review, 1975-2014, National Cancer Institute. Bethesda, MD, http://seer.cancer.gov/csr/1975_2014/, based on November 2016 SEER data submission, posted to the SEER web site, April 2017

Therkildsen C, Bergmann T K, Henrichsen-Schnack T, Ladelund S, Nilbert M. The predictive value of KRAS, NRAS, BRAF, PIK3CA and PTEN for anti-EGFR treatment in metastatic colorectal cancer: A systematic review and meta-analysis. Acta Oncol (Madr). 2014; 53(7):852-64.

Xiang S Y, Lilly E. A selective CDC7 inhibitor (LY3177833) impacts chromosome dynamics and has robust and durable activity in PDX tumor models. AACR Annual Meeting 2016. Late breaking abstract.

Zehir A, Benayed R, Shah R H, et al. Mutational landscape of metastatic cancer revealed from prospective clinical sequencing of 10,000 patients. Nat Med [Internet]. 2017; 23(6). Available from: http://www.nature.com/doifinder/10.1038/nm.4333

SEQUENCE LISTING

```
<160> NUMBER OF SEQ ID NOS: 1

<210> SEQ ID NO 1
<211> LENGTH: 25
<212> TYPE: PRT
<213> ORGANISM: Homo sapiends

<400> SEQUENCE: 1

Arg Arg Thr Asp Ala Leu Thr Ser Ser Pro Gly Arg Asp Leu Pro Pro
1               5                   10                  15

Phe Glu Asp Glu Ser Glu Gly Leu Leu
            20                  25
```

Huggett M T, Tudzarova S, Proctor I, et al. Cdc7 is a potent anti-cancer target in pancreatic cancer due to abrogation of the DNA origin activation checkpoint. Oncotarget [Internet]. 2016 April; 7(14):18495-507. Available from: http://www.oncotarget.com/abstract/7611

ICH Harmonised Tripartite Guideline: Nonclinical Evaluation For Anticancer Pharmaceuticals S9. International Conference on Harmonisation of Technical Requirements for Registration of Pharmaceuticals for Human Use. 2009.

Iwai K, Gotou M, Yamanaka K, Ohashi A. Phospho-proteomics analysis to determine the signaling pathways affected by a novel CDC7-selective inhibitor TAK-931. AACR Annual Meeting 2018. Abstract 2312.

Larasati, & Duncker, B. P. (2016). Mechanisms Governing DDK Regulation of the Initiation of DNA Replication. Genes, 8(1), 3. https://doi.org/10.3390/genes8010003

Montagnoli A, Tenca P, Sola F, et al. Cdc7 Inhibition Reveals a p53-Dependent Replication Checkpoint That Is Defective in Cancer Cells. Cancer Res. 2004; 64(19): 7110-6.

Rodriguez-Acebes S, Proctor I, Loddo M, et al. Targeting DNA replication before it starts: Cdc7 as a therapeutic target in p53-mutant breast cancers. Am J Pathol [Internet]. 2010 October; 177(4):2034-45. Available from: http://www.ncbi.nlm.nih.gov/pubmed/20724597

Schukken K M, Foijer F. CIN and Aneuploidy: Different Concepts, Different Consequences. BioEssays. 2018; 40(1):1-9.

Swords R, Mahalingam D, O'Dwyer M, et al. Cdc7 kinase—A new target for drug development. Eur J Cancer [Internet]. 2010 January; 46(1):33-40. Available from: http://dx.doi.org/10.1016/j.ejca.2009.09.020

What is claimed is:

1. A method of treating a cancer, the method comprising:

administering to a human subject with the cancer a therapeutically effective amount of a compound of formula (I-D) or a pharmaceutically acceptable salt thereof:

(I-D)

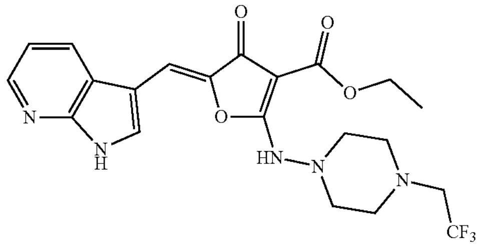

wherein the therapeutically effective amount is 100, 160, or 200 mg/day, and half of the therapeutically effective amount is administered twice a day (BID), and wherein the cancer is acute myeloid leukemia, bladder cancer, colon cancer, cecum cancer, renal cancer, head-and-neck cancer, melanoma, gastric cancer, colorectal cancer, hematologic cancer, breast cancer, or cervical cancer.

2. The method of claim 1, wherein the subject is identified as having one or more of the inclusion criteria disclosed in the table below:

| Laboratory Test | Value required |
| --- | --- |
| Hemoglobin | ≥90 g/L |
| Absolute neutrophil count | ≥1.5 × $10^9$/L |
| Platelet count | ≥120 × $10^9$/L |
| Bilirubin | ≤1.5 × upper limit of normal (ULN) unless due to Gilbert's syndrome in which case up to 3 × ULN is permissible |
| Alanine aminotransferase (ALT), aspartate aminotransferase (AST) and alkaline phosphatase (ALP) | ≤2.5 × ULN For the Expansion stage, up to 5 × ULN is permissible if the increase is due to tumor. |
| Serum creatinine or Calculated creatinine clearance | ≤1.5 × ULN or ≥60 mL/min using Cockcroft-Gault formula. |

3. The method of claim 1, wherein the subject has not previously had Cdc7 inhibitor therapy.

4. The method of claim 1, wherein either (i) the compound is administered for at least 5 consecutive days; or (ii) the compound is administered following a dosing schedule selected from the group consisting of: 5 days of dosing followed by 2 days of non-dosing each week; 1 week of daily dosing followed by 1, 2, or 3 weeks of non-dosing; 2 or 3 weeks of daily dosing followed by 1, or 2 weeks of non-dosing; and dosing on days 2 and 3 of a weekly cycle.

5. The method of claim 1, wherein the hematologic cancer is selected from the group consisting of: acute myeloid leukemia (AML), chronic myelogenous leukemia (CML), chronic eosinophilic leukemia, and diffuse large B-cell lymphoma (DLBCL).

6. The method of claim 5, wherein the cancer is diffuse large B-cell lymphoma (DLBCL).

7. The method of claim 1, wherein the cancer is not categorized as having a high microsatellite instability (MSI-H) status, or wherein the cancer is categorized as having a microsatellite stability stable (MSS) status.

8. The method of claim 1, wherein a tumor associated with the cancer comprises a phenotype selected from the group consisting of: chromosome instability (CIN), a spindle checkpoint assembly defect, a mitosis defect, a G1/S checkpoint defect, and combinations thereof.

9. The method of claim 1, wherein a tumor associated with the cancer comprises a Wnt signaling pathway mutation; wherein the Wnt signaling pathway mutation is selected from the group consisting of: an Adenomatous polyposis coli (APC) gene mutation, a FAT1 mutation, a FAT4 mutation, and combinations thereof.

10. The method of claim 1, wherein the method results in at least one of:

a plasma $C_{max}$ greater than 600 ng/mL of the compound in the subject after administration;

an $AUC_{last}$ greater than 5800 ng-h/mL of the compound in the subject after administration; and an intra-tumoral concentration of greater than 500 ng/mL of the compound in the subject after administration.

11. The method of claim 1, wherein the method results in growth inhibition of a tumor or lesion associated with the cancer; wherein the tumor or lesion growth is inhibited by at least 10% relative to an untreated tumor.

12. The method of claim 1, wherein the method results in a regression of a tumor associated with the cancer.

13. The method of claim 1, wherein the method further comprises administering to the subject a second therapeutically effective amount of one or more additional treatments, wherein the additional treatments are selected from the group consisting of trametinib, rapamycin, bexarotene, tretinoin, ABT-199, copanlisib, BMB673, KU-60019, barasertib, CF1-402257, erlotinib, gemcitabine, and radiation.

14. The method of claim 13, wherein the compound and the one or more additional treatments in combination demonstrate synergistic effects.

15. The method of claim 1, wherein the compound is administered orally.

16. The method of claim 1, wherein the hematologic cancer is AML.

17. The method of claim 1, wherein the subject is administered a bis-hydrochloride salt of the compound of formula (I-D).

18. The method of claim 1, wherein the therapeutically effective amount of the compound is 100 mg/day, and half of the therapeutically effective amount is administered twice a day (BID).

19. The method of claim 1, wherein the therapeutically effective amount of the compound is 160 mg/day, and half of the therapeutically effective amount is administered twice a day (BID).

20. The method of claim 1, wherein the therapeutically effective amount of the compound is 200 mg/day, and half of the therapeutically effective amount is administered twice a day (BID).

* * * * *